(12) United States Patent
Wu et al.

(10) Patent No.: US 9,266,961 B2
(45) Date of Patent: Feb. 23, 2016

(54) ANTI-PCSK9 ANTIBODIES, FORMULATIONS, DOSING, AND METHODS OF USE

(71) Applicant: Genentech, Inc., South San Francisco, CA (US)

(72) Inventors: Yan Wu, Foster City, CA (US); Cecilia Pui Chi Chiu, South San Francisco, CA (US); Daniel K. Kirchhofer, Los Altos, CA (US); Andrew Peterson, South San Francisco, CA (US); Ganesh A. Kolumam, South San Francisco, CA (US); Monica Kong Beltran, South San Francisco, CA (US); Paul Moran, South San Francisco, CA (US); Wei Li, South San Francisco, CA (US); Xanthe M. Lam, South San Francisco, CA (US); Lin Luis, South San Francisco, CA (US); Ada Hui, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/918,755

(22) Filed: Jun. 14, 2013

(65) Prior Publication Data

US 2013/0344085 A1 Dec. 26, 2013

Related U.S. Application Data

(60) Provisional application No. 61/786,280, filed on Mar. 14, 2013, provisional application No. 61/660,605, filed on Jun. 15, 2012.

(51) Int. Cl.
*C07K 16/40* (2006.01)
*A61K 39/395* (2006.01)
*A61K 39/00* (2006.01)

(52) U.S. Cl.
CPC ............ *C07K 16/40* (2013.01); *A61K 39/39591* (2013.01); *A61K 2039/505* (2013.01); *C07K 2317/34* (2013.01); *C07K 2317/55* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,444,874 A | 4/1984 | Silverman et al. |
| 4,676,980 A | 6/1987 | Segal et al. |
| 4,737,456 A | 4/1988 | Weng et al. |
| 4,816,567 A | 3/1989 | Cabilly et al. |
| 5,208,020 A | 5/1993 | Chari et al. |
| 5,260,440 A | 11/1993 | Hirai et al. |
| 5,273,995 A | 12/1993 | Roth |
| 5,416,064 A | 5/1995 | Chari et al. |
| 5,500,362 A | 3/1996 | Robinson et al. |
| 5,571,894 A | 11/1996 | Wels et al. |
| 5,587,458 A | 12/1996 | King et al. |
| 5,591,828 A | 1/1997 | Bosslet et al. |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,750,373 A | 5/1998 | Garrard et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,877,296 A | 3/1999 | Hamann et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,602,684 B1 | 8/2003 | Umana et al. |

(Continued)

FOREIGN PATENT DOCUMENTS

| | | |
|---|---|---|
| EP | 0 033 538 A2 | 8/1881 |
| EP | 0 033 538 A3 | 8/1881 |
| EP | 0 033 538 B1 | 8/1881 |
| EP | 0 404 097 B1 | 12/1990 |
| EP | 0 409 281 A1 | 1/1991 |

(Continued)

OTHER PUBLICATIONS

Almagro et al., "Humanization of antibodies" *Front Biosci* 13:1619-1633, (Jan. 1, 2008).

(Continued)

*Primary Examiner* — Brian J Gangle
*Assistant Examiner* — Andrea McCollum
(74) *Attorney, Agent, or Firm* — Morrison & Foerster LLP

(57) ABSTRACT

The invention provides anti-PCSK9 antibodies, formulations, dosing regimens, and methods of using the same.

42 Claims, 39 Drawing Sheets

(56) References Cited

U.S. PATENT DOCUMENTS

| | | | |
|---|---|---|---|
| 6,630,579 | B2 | 10/2003 | Chari et al. |
| 6,737,056 | B1 | 5/2004 | Presta |
| 6,982,321 | B2 | 1/2006 | Winter |
| 7,041,870 | B2 | 5/2006 | Tomizuka et al. |
| 7,087,409 | B2 | 8/2006 | Barbas, III et al. |
| 7,125,978 | B1 | 10/2006 | Vezina et al. |
| 7,189,826 | B2 | 3/2007 | Rodman |
| 7,300,754 | B2 | 11/2007 | Abi Fadel et al. |
| 7,332,581 | B2 | 2/2008 | Presta |
| 7,368,531 | B2 | 5/2008 | Rosen et al. |
| 7,371,826 | B2 | 5/2008 | Presta |
| 7,498,298 | B2 | 3/2009 | Doronina et al. |
| 7,504,256 | B1 | 3/2009 | Ogawa et al. |
| 7,521,541 | B2 | 4/2009 | Eigenbrot et al. |
| 7,527,791 | B2 | 5/2009 | Adams et al. |
| 7,572,618 | B2 | 8/2009 | Mintier et al. |
| 7,846,706 | B2 | 12/2010 | Mintier et al. |
| 7,928,189 | B2 | 4/2011 | Mayne et al. |
| 8,062,640 | B2 | 11/2011 | Sleeman et al. |
| 8,080,243 | B2 | 12/2011 | Liang et al. |
| 8,088,571 | B2 | 1/2012 | Seidah et al. |
| 8,168,762 | B2 | 5/2012 | Jackson et al. |
| 8,187,833 | B2 | 5/2012 | Seidah et al. |
| 8,188,233 | B2 | 5/2012 | Condra et al. |
| 8,188,234 | B2 | 5/2012 | Condra et al. |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0079574 | A1 | 4/2005 | Bond |
| 2005/0114934 | A1 | 5/2005 | Hedges |
| 2005/0119455 | A1 | 6/2005 | Fuh et al. |
| 2005/0123546 | A1 | 6/2005 | Umana et al. |
| 2005/0260186 | A1 | 11/2005 | Bookbinder et al. |
| 2005/0266000 | A1 | 12/2005 | Bond et al. |
| 2006/0025576 | A1 | 2/2006 | Miller et al. |
| 2006/0104968 | A1 | 5/2006 | Bookbinder et al. |
| 2007/0061900 | A1 | 3/2007 | Murphy et al. |
| 2007/0117126 | A1 | 5/2007 | Sidhu et al. |
| 2007/0134759 | A1 | 6/2007 | Nishiya et al. |
| 2007/0160598 | A1 | 7/2007 | Dennis et al. |
| 2007/0166305 | A1 | 7/2007 | Hanai et al. |
| 2007/0237764 | A1 | 10/2007 | Birtalan et al. |
| 2007/0292936 | A1 | 12/2007 | Barthelemy et al. |
| 2008/0069820 | A1 | 3/2008 | Fuh et al. |
| 2008/0241884 | A1 | 10/2008 | Shitara et al. |
| 2009/0002360 | A1 | 1/2009 | Chen et al. |
| 2009/0130691 | A1 | 5/2009 | Seidah et al. |
| 2009/0326202 | A1 | 12/2009 | Jackson et al. |
| 2010/0041102 | A1 | 2/2010 | Sitlani et al. |
| 2010/0092997 | A1 | 4/2010 | Nakamura et al. |
| 2010/0166768 | A1 | 7/2010 | Sleeman et al. |
| 2010/0233177 | A1 | 9/2010 | Yowe et al. |
| 2011/0003315 | A1 | 1/2011 | Seidah et al. |
| 2011/0033465 | A1 | 2/2011 | Hedrick et al. |
| 2011/0230392 | A1 | 9/2011 | Chiang et al. |
| 2012/0016009 | A1 | 1/2012 | Fitzgerald et al. |
| 2012/0076799 | A1 | 3/2012 | Sparrow et al. |
| 2012/0076964 | A1 | 3/2012 | Mitadera et al. |
| 2012/0082679 | A1 | 4/2012 | Sparrow et al. |
| 2012/0082680 | A1 | 4/2012 | Sitlani et al. |
| 2012/0195910 | A1 | 8/2012 | Wu et al. |

FOREIGN PATENT DOCUMENTS

| | | | |
|---|---|---|---|
| EP | 0 409 281 | B1 | 1/1991 |
| EP | 0 521 471 | A1 | 1/1993 |
| EP | 0 521 471 | B1 | 1/1993 |
| EP | 0 425 235 | B1 | 9/1996 |
| EP | 1 067 182 | A2 | 1/2001 |
| EP | 1 067 182 | A3 | 1/2001 |
| EP | 1 067 182 | A8 | 1/2001 |
| EP | 1 331 266 | A1 | 7/2003 |
| EP | 1 498 491 | A1 | 1/2005 |
| EP | 1 502 603 | A1 | 2/2005 |
| EP | 1 688 439 | A1 | 8/2006 |
| EP | 1 705 251 | A1 | 9/2006 |
| JP | 2005-130764 | A | 5/2005 |
| WO | WO-93/01161 | A1 | 1/1993 |
| WO | WO-93/08829 | A1 | 5/1993 |
| WO | WO-93/11161 | A1 | 6/1993 |
| WO | WO-93/16185 | A2 | 8/1993 |
| WO | WO-94/11026 | A2 | 5/1994 |
| WO | WO-94/11026 | A3 | 5/1994 |
| WO | WO-94/29351 | A2 | 12/1994 |
| WO | WO-94/29351 | A3 | 12/1994 |
| WO | WO-97/30087 | A1 | 8/1997 |
| WO | WO-98/58964 | A1 | 12/1998 |
| WO | WO-99/22764 | A1 | 5/1999 |
| WO | WO-99/51642 | A1 | 10/1999 |
| WO | WO-00/61739 | A1 | 10/2000 |
| WO | WO-01/29246 | A1 | 4/2001 |
| WO | WO-01/57081 | A2 | 8/2001 |
| WO | WO-01/57081 | A3 | 8/2001 |
| WO | WO-01/98468 | A2 | 12/2001 |
| WO | WO-01/98468 | A3 | 12/2001 |
| WO | WO-02/14358 | A2 | 2/2002 |
| WO | WO-02/14358 | A3 | 2/2002 |
| WO | WO-02/31140 | A1 | 4/2002 |
| WO | WO-02/46383 | A2 | 6/2002 |
| WO | WO-02/46383 | A3 | 6/2002 |
| WO | WO-03/011878 | A2 | 2/2003 |
| WO | WO-03/011878 | A3 | 2/2003 |
| WO | WO-03/084570 | A1 | 10/2003 |
| WO | WO-03/085107 | A1 | 10/2003 |
| WO | WO-03/085119 | A1 | 10/2003 |
| WO | WO-2004/056312 | A2 | 7/2004 |
| WO | WO-2004/056312 | A3 | 7/2004 |
| WO | WO-2004/097047 | A1 | 11/2004 |
| WO | WO-2005/035586 | A1 | 4/2005 |
| WO | WO-2005/035778 | A1 | 4/2005 |
| WO | WO-2005/053742 | A1 | 6/2005 |
| WO | WO-2005/100402 | A1 | 10/2005 |
| WO | WO-2006/029879 | A2 | 3/2006 |
| WO | WO-2006/029879 | A3 | 3/2006 |
| WO | WO-2006/044908 | A2 | 4/2006 |
| WO | WO-2006/044908 | A3 | 4/2006 |
| WO | WO-2007/030937 | A2 | 3/2007 |
| WO | WO-2007/030937 | A3 | 3/2007 |
| WO | WO-2007/128121 | A1 | 11/2007 |
| WO | WO-2008/057457 | A2 | 5/2008 |
| WO | WO-2008/057457 | A3 | 5/2008 |
| WO | WO-2008/057458 | A2 | 5/2008 |
| WO | WO-2008/057458 | A3 | 5/2008 |
| WO | WO-2008/063382 | A2 | 5/2008 |
| WO | WO-2008/063382 | A3 | 5/2008 |
| WO | WO-2008/066776 | A2 | 6/2008 |
| WO | WO-2008/066776 | A3 | 6/2008 |
| WO | WO-2008/077546 | A1 | 7/2008 |
| WO | WO-2008/105797 | A2 | 9/2008 |
| WO | WO-2008/105797 | A3 | 9/2008 |
| WO | WO-2008/109871 | A2 | 9/2008 |
| WO | WO-2008/109871 | A3 | 9/2008 |
| WO | WO-2008/125623 | A2 | 10/2008 |
| WO | WO-2008/125623 | A3 | 10/2008 |
| WO | WO-2008/133647 | A2 | 11/2008 |
| WO | WO-2008/133647 | A3 | 11/2008 |
| WO | WO-2009/026558 | A1 | 2/2009 |
| WO | WO-2009/055783 | A2 | 4/2009 |
| WO | WO-2009/055783 | A3 | 4/2009 |
| WO | WO-2009/089004 | A1 | 7/2009 |
| WO | WO-2009/100297 | A1 | 8/2009 |
| WO | WO-2009/100318 | A1 | 8/2009 |
| WO | WO-2010/029513 | A2 | 3/2010 |
| WO | WO-2010/029513 | A3 | 3/2010 |
| WO | WO-2010/077854 | A1 | 7/2010 |
| WO | WO-2010/077854 | A8 | 7/2010 |
| WO | WO-2011/053759 | A1 | 5/2011 |
| WO | WO-2011/053783 | A2 | 5/2011 |

(56) References Cited

FOREIGN PATENT DOCUMENTS

| | | |
|---|---|---|
| WO | WO-2011/053783 A3 | 5/2011 |
| WO | WO-2011/072263 A1 | 6/2011 |
| WO | WO-2011/111007 A2 | 9/2011 |
| WO | WO-2011/111007 A3 | 9/2011 |
| WO | WO-2012/054438 A1 | 4/2012 |
| WO | WO-2012/088313 A1 | 6/2012 |
| WO | WO-2012/101251 A1 | 8/2012 |
| WO | WO-2012/101252 A2 | 8/2012 |
| WO | WO-2012/101252 A3 | 8/2012 |
| WO | WO-2012/101253 A1 | 8/2012 |
| WO | WO-2012/146776 A1 | 11/2012 |
| WO | WO-2012/154999 A1 | 11/2012 |
| WO | WO-2012/168491 A1 | 12/2012 |
| WO | WO-2012/170607 A2 | 12/2012 |
| WO | WO-2012/170607 A3 | 12/2012 |

OTHER PUBLICATIONS

Baca et al., "Antibody humanization using monovalent phage display" *J Biol Chem* 272(16):10678-10684 (1997).

Boerner et al., "Production of antigen-specific human monoclonal antibodies from in vitro-primed human splenocytes" *J Immunol* 147(1):86-95, (Jul. 1, 1991).

Brennan et al., "Preparation of Biospecific Antibodies by Chemical Recombination of Monoclonal Immunoglobulin G1 Fragments" *Science* 229(4708):81-83, (Jul. 5, 1985).

Brodeur et al. *Monoclonal Antibody Production Techniques and Applications*, Chapter 4, "Mouse-human myeloma partners for the production of heterohybridomas," Lawrence B. Schook ed., New York:Marcel Dekker, Inc., pp. 51-63, (1987).

Brüeggemann et al., "Comparison of the effector functions of human immunoglobulins using a matched set of chimeric antibodies" *J. Exp. Med.* 166:1351-1361, (Nov. 1, 1987).

Carter et al., "Humanization of an anti-p185$^{HER2}$ antibody for human cancer therapy" *Proc. Natl. Acad. Sci. USA* 89:4285-4289, (May 1992).

Chan et al. "A proprotein convertase subtilisin/kexin type 9 neutralizing antibody reduces serum cholesterol in mice an dnonhuman primates," *Proc. Natl. Acad. Sci. USA* 106(24):9820-9825, (Jun. 16, 2009).

Chaparro-Riggers et al. "Increasing serum half-life and extending cholesterol loweing in Vivo by engineering antibody with pH-sensitive binding to PCSK9," *Journal of Biological Chemistry* 287(14):11090-11097, (Mar. 30, 2012).

Chari et al., "Immunoconjugates containing novel maytansinoids: Promising anticancer drugs" *Cancer Res* 52:127-131, (Jan. 1, 1992).

Charlton, *Methods in Molecular Biology* "14 Expression and Isolation of Recombinant Antibody Fragments in *E.coli*" B.K.C. Lo, edition, Totowa, NJ,:Humana Press, vol. 248:245-54, (2004).

Chen et al., "Selection and analysis of an optimized anti-VEGF antibody: Crystal structure of an affinity-matured Fab in complex with antigen" *J Mol Biol* 293:865-881, (1999).

Cheung et al., "Epitope-specific antibody response to the surface antigen of duck hepatitis B virus in infected ducks" *Virology* 176(2):546-552, (1990).

Chothia and Lesk, "Canonical structures for the hypervariable regions of immunoglobulins" *J Mol Biol* 196(4):901-917, (1987).

Chowdhury, "Engineering hot spots for affinity enhancement of antibodies" *Methods Molec Biol* 207:179-196, (2008).

Clackson et al., "Making antibody fragments using phage display libraries" *Nature* 352(6336):624-628, (Aug. 15, 1991).

Clynes et al., "Fc receptors are required in passive and active immunity to melanoma" *Proc. Natl. Acad. Sci. USA* 95(2):652-656, (Jan. 1998).

Cragg et al., "Complement-mediated lysis by anti-CD20 mAb correlates with segregation into liqid rifts," *Blood* 101(3):1045-1052, (Feb. 1, 2003).

Cragg et al., "Antibody specificity controls in vivo effector mechanisms of anti-CD20 reagents" *Blood* 103(7):2738-2743, (Apr. 1, 2004).

Cunningham and Wells, "High-resolution epitope mapping of hGH-receptor interactions by alanine-scanning mutagenesis" *Science* 244:1081-1085, (Jun. 2, 1989).

Dall'Acqua et al., "Antibody humanization by framework shuffling" *Methods* 36:43-60, (2005).

Dubowchik et al., "Doxorubicin immunoconjugates containing bivalent, lysosomally-cleavable dipeptide linkages" *Bioorg Med Chem Lett* 12:1529-1532 (2002).

Duncan and Winter, "The Binding Site for Clq on IgG" *Nature* 332:738-740, (Apr. 21, 1988).

Eigenbrot et al., "X-Ray structures of the antigen-binding domains from three variants of humanized anti-p185$^{HER2}$ antibody 4D5 and comparison With molecular modeling" *J Mol Biol* 229:969-995, (1993).

Fellouse et al., "Synthetic antibodies from a four-amino-acid code: A dominant role for tyrosine in antigen recognition" *Proc. Natl. Acad. Sci. USA* 101(34):12467-12472, (Aug. 24, 2004).

Flatman et al., "Process analytics for purification of monoclonal antibodies" *J Chromatogr* 848:79-87, (2007).

Gallop et al., "Applications of combinatorial technologies to drug discovery. 1. background and peptide combinatorial libraries" *J Med Chem* 37(9):1233-1251, (1994).

Gazzano-Santoro et al., "A non-radioactive complement-dependent cytotoxicity assay for anti-CD20 monoclonal antibody" *J Immunol Methods* 202:163-171, (1997).

Gerngross, "Advances in the production of human therapeutic proteins in yeasts and filamentous fungi" *Nat Biotech* 22(11):1409-1414, (Nov. 2004).

Graham et al., "Characteristics of a human cell line transformed by DNA from human adenovirus type 5" *J Gen Virol* 36(1):59-72, (Jul. 1977).

Griffiths et al., "Human anti-self antibodies with high specificity from phage display libraries" *EMBO J* 12(2):725-734, (1993).

Gruber et al., "Efficient tumor cell lysis mediated by a bispecific single chain antibody expressed in *Escherichia coli*" *J Immunol* 152:5368-5374, (1994).

Guyer et al., "Immunoglobulin binding by mouse intestinal epithelial cell receptors" *J Immunol* 117(2):587-593, (Aug. 1976).

Hampton et al., "The self-inhibited structure of full-length PCSK9 at 1.9 A reveals structural homology with resistin within the C-terminal domain" *Proc. Natl. Acad. Sci. USA* 104(37):14604-14609, (Sep. 11, 2007).

Hellstrom et al., "Strong antitumor activities of IgG3 antibodies to a human melanoma-associated ganglioside" *Proc. Natl. Acad. Sci. USA* 82:1499-1502, (Mar. 1985).

Hellstrom et al., "Antitumor effects of L6, an IgG2a antibody that reacts with most human carcinomas" *Proc. Natl. Acad. Sci. USA* 83:7059-7063, (Sep. 1986).

Hinman et al., "Preparation and characterization of monoclonal antibody conjugates of the calicheamicins: A novel and potent family of antitumor antibiotics" *Cancer Res* 53:336-3342, (1993).

Hollinger et al., ""Diabodies": Small Bivalent and Bispecific Antibody Fragments" *Proc. Natl. Acad. Sci. USA* 90:6444-6448, (Jul. 1993).

Holm et al., "Functional mapping and single chain construction of the anti-cytokeratin 8 monoclonal antibody TS1," *Molecular Immunology* 44:1075-1084, (2007).

Hoogenboom et al., "Overview of antibody phage-display technology and its applications" *Methods Mol Biol* 178:1-37, ( 2002).

Hoogenboom and Winter, "By-passing immunisation human antibodies from synthetic repertoires of germline $V_H$ gene segments rearranged in vitro" *J. Mol. Biol.* 227:381-388, (1992).

Hudson et al., "Engineered antibodies" Nature Medicine 9(1):129-134, (Jan. 2003).

Idusogie et al. "Mapping of the C1q Binding Site on Rituxan, a Chimeric Antibody with A human IgG1 Fc," *J. Immunol.* 164:4178-4184, (2000).

Jeffrey et al., "Dipeptide-based highly potent doxorubicin antibody conjugates" *Bioorganic Med Chem Letters* 16:358-362, (2006).

Kam et al., "Carbon nanotubes as multifunctional biological transporters and near-infrared agents for selective cancer cell destruction" *Proc. Natl. Acad. Sci. USA* 102(33):11600-11605, (Aug. 2005).

(56) References Cited

OTHER PUBLICATIONS

Kanda et al., "Comparison of cell lines for stable production of fucose-negative antibodies with enhanced ADCC" *Biotechnol Bioeng* 94(4):680-688, (Jul. 5, 2006).

Kashmiri et al., "SDR grafting—a new approach to antibody humanization" *Methods* 36:25-34, (2005).

Kim et al., "Localization of the site of the murine IgG1 molecule that is involved in binding to the murine intestinal Fc receptor" *Eur J Immunol* 24(10):2429-2434, (Oct. 1994).

Kindt et al. *Kuby Immunology* "Antigens and Antibodies Chapter 4" 6th ed edition, N.Y.:W.H. Freeman and Co,:p. 91, (2007).

King et al., "Monoclonal antibody conjugates of doxorubicin prepared with branched peptide linkers: Inhibition of aggregation by methoxytriethyleneglycol chains" *J Med Chem* 45:4336-4343, (2002).

Kirkland et al., "Analysis of the fine specificity and cross-reactivity of monoclonal anti-lipid A antibodies" *J. Immunol.* 137(11):3614-3619, (Dec. 1, 1986).

Klimka et al., "Human anti-CD30 recombinant antibodies by guided phage antibody selection using cell panning" *BR J Cancer* 83(2):252-260, (2000).

Kostelny et al., "Formation of a bispecific antibody by the use of leucine zippers" *J Immunol.* 148:1547-1553, (Mar. 1, 1992).

Kozbor et al., "A Human Hybrid Myeloma for Production of Human Monoclonal Antibodies" *J Immunol* 133(6):3001-3005, (Dec. 1, 1984).

Kratz et al., "Prodrugs of anthracyclines in cancer chemotherapy" *Curr Med Chem* 13:477-523, (2006).

Lagace et al. "Secreted PCSK9 decrease the number of LDL receptors in hepatopcytes an din livers of parabiotic mice," *J. of Clin. Investigation* 116(11):2995-3005, (2006).

Lee et al., "Bivalent antibody phage display mimics natural immunoglobulin" *J Immunol Methods* 284(1-2):119-132, (2004).

Lee et al., "High-affinity human antibodies from phage-displayed synthetic Fab libraries with a single framework scaffold" *J Mol Biol* 340(5):1073-1093, (2004).

Li et al., "Optimization of humanized IgGs in glycoengineered *Pichia pastoris*" *Nat Biotechnol* 24(2):210-215, (Feb. 2006).

Li et al., "Human antibodies for immunotherapy development generated via a human B cell hybridoma technology" *Proc. Natl. Acad. Sci. USA* 103(10):3557-62, (Mar. 2006).

Liang et al. et al., "Function Blocking Antibodies to Neuropilin-1 Generated from a Designed Human Synthetic Antibody Phage Library" *J Mol Biol* 366:815-829, (2007).

Liang et al. "Proprotein convertase substilisin/kexin type 9 antagonism reduces low density lipoprotein cholesterol in statin-treated hypercholesterolemic nonhuman primates," *The Journal of Pharmacology and Experimental Therapeutics* 340:228-236, (2012).

Lode et al., "Targeted therapy with a novel enediyene antibiotic calicheamicin V11 effectively suppresses growth and dissemination of liver metastases in a syngeneic model of murine neuroblastoma" *Cancer Res* 58:2925-2928, (1998).

Lonberg, "Human antibodies from transgenic animals" *Nat Biotechnol* 23(9):1117-1125, (Sep. 2005).

Lonberg, "Fully human antibodies from transgenic mouse and phage display platforms" *Current Opin Immunol* 20:450-459, (2008).

Lopez et al. "Inhibition of PCSK9 as a Novel Strategy for the Treatment of hypercholesterolemia," *Drug News & Perspectives* 21(6):323-330, (2008).

Marks et al., "By-passing immunization, Human antibodies from V-gene libraries displayed on phage" *J. Mol. Biol.* 222:581-597 (1991).

Marks and Bradbury, *Methods Mol Biol, Antibody Engineering* "Selection of human antibodies from phage display libraries" Benny K. C. Lo,Humana Press, vol. 248:161-176, (2004).

Mather, "Establishment and characterization of two distinct mouse testicular epithelial cell lines" *Biol Reprod* 23:243-252, (1980).

Mather et al., "Culture of testicular cells in hormone-supplemented serum-free medium" *Ann NY Acad Sci* 383:44-68, (1982).

McCafferty et al., "Phage Antibodies: Filamentous Phage Displaying Antibody Variable Domains" *Nature* 348:552-554 (Dec. 1990).

Milstein and Cuello, "Hybrid hybridomas and their use in immunohistochemistry" *Nature* 305:537-540, (Oct. 6, 1983).

Moldenhauer et al., "Identity of HML-1 antigen on intestinal intraepithelial T cells and of B-ly7 antigen on hairy cell leukaemia" *Scand. J. Immunol.* 32(2):77-82, (Aug. 1990).

Morel et al., "Monoclonal antibodies to bovine serum albumin: affinity and specificity determinations" *Molec. Immunol.* 25:7-15, (Jan. 1988).

Morrison et al., "Chimeric human antibody molecules: Mouse antigen-binding domains with human constant region domains" *Proc. Natl. Acad. Sci. USA* 81:6851-6855, (Nov. 1984).

Nagy et al., "Stability of cytotoxic luteinizing hormone-releasing hormone conjugate (AN-152) containing doxorubicin 14-O-hemiglutarate in mouse and human serum in vitro: implications for the design of preclinical studies" *Proc. Natl. Acad. Sci. USA* 97(2):829-34, (Jan. 18, 2000).

Ni et al. "A proprotein convertase subtilisin-like/kexin type 9 (PCSK9) c-terminal domain antibody antigen-bidning fragment inhibits PCSK9 internalization and restores low density lipoprotein uptake," *The Journal of Biological Chemistry* 285(17):12882-12891, (Apr. 23, 2010).

Ni et al. "A PCSK9-binding antibody that structurally mimics the EGF(A) domain of LDL-receptor reduces LDL cholesterol in vivo," *Journal of Lipid Research* 52:78-86, (2011).

Ni, "Research progress and future perspectives in antibodomics and antibodomic drugs" *Xiandai Mianyixue* (Abstract only) 26(4):265-268, (2006).

Okazaki et al., "Fucose depletion from human IgG1 oligosaccharide enhances binding enthalpy and association rate between IgG1 and FcγRIIIa" *J Molec Biol* 336:1239-1249, (2004).

Osbourn et al., "From rodent reagents to human therapeutics using antibody guided selection" *Methods* 36:61-68, (2005).

Padlan, "A possible procedure for reducing the immunogenicity of antibody variable domains while preserving their ligand-binding properties" *Mol Immunol* 28(4/4):489-498, (1991).

Peterson et al., "PCSK9 Function and Physiology" *J. Lipid Res.* 49(7):1595-1599, (2008).

Petkova et al., "Enhanced half-life of genetically engineered human IgG1 antibodies in a humanized FcRn mouse model: potential application in humorally mediated autoimmune disease" *Int Immunol* 18(12):1759-69, (Dec. 2006).

Pluckthun. *The Pharmacology of Monoclonal Antibodies: Handbook of Pharmacology* "Antibodies from *Escherichia coli*" (Chapter 11), Rosenberg and Moore, eds., Berlin:Springer-Verlag, vol. 113:269-315, (1994).

Portolano et al., "Lack of promiscuity in autoantigen-specific H and L chain combinations as revealed by human H and L chain Roulette" *J Immunol* 150(3):880-887, (Feb. 1993).

Presta et al., "Humanization of an Antibody Directed Against IgE" *J Immunol* 151(5):2623-2632, (Sep. 1, 1993).

Presta et al., "Humanization of an Anti-Vascular Endothelial Growth Factor Monoclonal Antibody for the Therapy of Solid Tumors and Other Disorders" *Cancer Res* 57(20):4593-4599, (Oct. 15, 1997).

Queen et al., "A humanized antibody that binds to the interleukin 2 receptor" *Proc. Natl. Acad. Sci. USA* 86(24):10029-10033, (Dec. 1989).

Ravetch and Kinet, "Fc receptors" *Ann Rev Immunol* 9:457-492, (1991).

Riechmann et al., "Reshaping human antibodies for therapy" *Nature* 332:323-327, (Mar. 1988).

Ripka et al., "Two chinese hamster ovary glycosylation mutants affected in the conversion of GDP-mannose to GDP-fucose" *Arch Biochem Biophys* 249(2):533-545, (Sep. 1986).

Rosok et al., "A combinatorial library strategy for the rapid humanization of anticarcinoma BR96 Fab" *J Biol Chem* 271(37):22611-22618, (Sep. 13, 1996).

Shields et al. et al., "High resolution mapping of the binding site on human IgG1 for Fc gamma RI, Fc gamma RII, Fc gamma RIII, and FcRn and design of IgG1 variants with improved binding to the Fc gamma R" *J Biol Chem* 276(9):6591-6604, (Mar. 2, 2001).

(56) References Cited

OTHER PUBLICATIONS

Sidhu et al., "Phage-displayed antibody libraries of synthetic heavy chain complementarity determining regions" *J Mol Biol* 338(2):299-310, (2004).
Sims et al., "A Humanized CD18 Antibody Can Block Function Without Cell Destruction" *J Immunol* 151(4):2296-2308, (Aug. 15, 1993).
Stahli et al., "Distinction of epitopes by monoclonal antibodies" *Methods Enzymol.* 92:242-253, (1983).
Stein et al. "Effect of a monoclonal antibody to PCSK9 on LDL cholesterol," *The New England Journal of Medicine* 366(12):1108-1118, (Mar. 22, 2012).
Stein et al. "Effect of a monoclonal antibody to PCSK9, REGN727/SAR236553, to reduce low-density lipoprotein cholesterol in patients with heterozygous familial hypercholesterolaemia on stable statin dose with or without ezetimibe therapy: a phase 2 randomised controlled trial," *The Lancet* 380:29-36, (Jul. 2, 2012).
Torgov et al., "Generation of an intensely potent anthracycline by a monoclonal antibody-β-galactosidase conjugate" *Bioconjugate Chemistry* 16:717-721, (2005).
Traunecker et al., "Bispecific Single Chain Molecules (Janusins) Target Cytotoxic Lymphocytes on HIV Infected Cells" *EMBO J* 10(12):3655-3659, (1991).
Tutt et al., "Trispecific F(ab')$_3$ derivatives that use cooperative signaling via the TCR/CD3 complex and CD2 to activate and redirect resting cytotoxic T cells" *J Immunol* 147(1):60-69, (Jul. 1991).
Urlaub et al., "Isolation of chinese hamster cell mutants deficient in dihydrofolate reductase activity" *Proc. Natl. Acad. Sci. USA* 77(7):4216-4220, (Jul. 1980).
Van Dijk and Van De Winkel, "Human antibodies as next generation therapeutics" *Curr Opin Chem Biol* 5(4):368-74, (Aug. 2001).
Vitetta et al., "Redesigning Nature's Poisons to Create Anti-Tumor Reagents" *Science* 238(4830):1098-1104, (Nov. 20, 1987).
Vollmers and Brandlein, "Death by stress: natural IgM-induced apoptosis" *Methods Find Exp Clin Pharmacol* 27(3):185-191, (2005).
Vollmers and Brandlein, "The 'early birds': Natural IgM antibodies and immune surveillance" *Histol Histopathol* 20:927-937, (2005).
Wang et al. "Antibody structure, instability, and formulation," *Journal of Pharmaceutical Sciences* 96(1):1-26, (2007).
Winter et al., "Making antibodies by phage display technology" *Annu Rev Immunol* 12:433-455, (1994).
Wright et al., "Effect of glycosylation on antibody function: implications for genetic engineering" *Trends Biotechnol.* 15(1):26-32, (1997).
Yamane-Ohnuki et al., "Establishment of FUT8 knockout Chinese hamster ovary cells: an ideal host cell line for producing completely defucosylated antibodies with enhanced antibody-dependent cellular cytotoxicity" *Biotechnol Bioeng* 87(5):614-622, (Sep. 2004).
Yazaki et al., "Expression of recombinant antibodies in mammalian cell lines" *Methods Molec Biol* 248:255-268, (2004).
Zhang et al. "An anti-PCSK9 antibody reduces LDL-cholesterol on top of a statin and suppresses hepatocyte SREBP-regulated genes," *International Journal of Biological Sciences* 8(3):310-327, (2012).
International Search Report mailed Oct. 1, 2013, for PCT Application No. PCT/US2013/046032, filed on Jun. 13, 2013, 11 pages.
Written Opinion mailed Oct. 1, 2013, for PCT Application No. PCT/US2013/046032, filed on Jun. 13, 2013, 6 pages.

Alborn et al. "Serum proprotein convertase subtilisin kexin type 9 is correlated dirtey with serum LDL cholesterol," *Clinical Chemistry* 53(10):1814-1819, (2007).
McNutt et al. "Catalytic activity is not required for secreted PCSK9 to reduce low density lipoprotein receptors in HepG2 cells," *Journal of Biological Chemistry* 282(29):20799-20803.
Qian et al. "Secreted PCSK9 downregultes low denisty lipoprotein receptor through receptor-medicated endocytosis," *Journal of Lipid Research* 48:1488-1498.
Maxwell et al. "Adenoviral-mediated expression of Pcsk9 in mice results in low-denity lipoprotein receptor knockout phenotype," *Proc. Natl. Acad. Sci. USA* 101(18):7100-7105, (May 4, 2004).
LaLanne et al. "Wild-type PCSK9 Inhibits LDL Clearance but does not affect apoB-containing lipoprotein production in mouse and cultured cells," *Journal of Lipid Research* 46:1312-1319, (2005).
Rashid et al. "Decreased plasma cholesterol and hypersensitivity to statins in mice lacking *Pcsk9*," *Proc. Natl. Acad. Sci. USA* 102(15):5374-5379, (Apr. 12, 2005).
Grozdanov et al. "Expression and localization of PCSK9 in rat hepatic cells," *Biochem. Cell Biol.* 84:80-92, (2006).
Costet et al. "Hepatic PCSK9 expression is regulated by nutritional status via insulin and sterol regulatory element-binding protein 1c," *The Journal of Biological Chemistry* 281(10):6211-6218, (Mar. 10, 2006).
Lambert et al. "Fasting Induces hyperlipidemia in mice overexpressing proprotein convertase subtilisin kexin type 9: Lack of Modulation of very-low-density lipoprotein hepatic output by the low-density lipoprotein receptor," *Endocinology* 147(10):4985-4995.
Zhao et al. "Molecular charcterization of loss-of-funciton mutations in PCSK9 and identification of a compund heterozygote," The American Journal of Human Genetics 79:514-523, (Sep. 2006).
Benjannet et al. "the Proprotein converstase (PC) PCSK9 is inactivated by furin and/or PC5/6A. Functional consequences of natural mutations and post-translational modifications," *The Journal of Biological Chemistry* 281(41):30561-30572, (Oct. 13, 2006).
Poirier et al. "Implication of the proprotein convertase NARC-1/ 'PCSK9 in the development of the nervous system," *Journal of Neurochemistry* 98:838-850, (2006).
Kwon et al. "Molecular basis for LDL receptor recongnition by PCSK9," *Proc. Natl. Acad. Sci. USA* 105(6):1820-1825.
Imgenex. "Peptide-affinity purified polyclonal anibody to pCSK9 (aa164-175)," last visited on Mar. 4, 2014, located at <http://.imgenex.com/antibody_details.php?catalog=IMG-31098&id-=&dmode-CT>, 1page.
Cayman Chemical Catalog. "PCSK9 polyclonal antibody, Cayman Chemical Item No. 10240, Proprotein Convertase subtilisin Kexin 9; NARC-1," located at <http://www.caymanchem.com/app/template/product.vm/catalog/10240, last visited on Mar. 3, 2014, 1 page.
R&DSystems. "Human Proprotein Convertase 9/pCSK9 Mab (Clone 410420), Catalog No. MAB38881," located at <http://www.rndsystems.com/Products/MAB38881, last visited on Mar. 3, 2014, 1 page.
R&DSystems. "Human Proprotein Convertase 9/PCSK9 Mab (Clone 4999111), Catalog No. MAB38882," located at <http://www.rndsystems.com/Products/MAB38882, last visited on Mar. 3, 2014, 1 page.
R&DSystems. "Human Proprotein Convertase 9/PCSK9 Affinity Purified Pab, Catalog No. AF3888," located at <http://www.rndsystems.com/Products/AF3888, last visited on Mar. 3, 2014, 1 page.
Duff et al., "Antibody-mediated disruption of the interaction between PCSK9 and the low-density lipoprotein receptor," *Biochem. J.* 419(3):577-584, (May 1, 2009).

| | Ka (1/Ms) | Kd (1/s) | KD (nM) |
|---|---|---|---|
| YW508.20.04b | 7.47E+04 | 5.65E-05 | 0.757 |
| YW508.20.06 | 1.04E+05 | 6.51E-05 | 0.628 |
| YW508.20.28b | 5.98E+04 | 2.09E-05 | 0.349 |
| YW508.20.33b | 5.26E+04 | 2.15E-05 | 0.408 |
| YW508.20.84 | 7.46E+04 | 3.59E-05 | 0.481 |

FIGURE 3B

| | Ka (1/Ms) | Kd (1/s) | KD (nM) |
|---|---|---|---|
| YW508.20.04b | 2.70E+05 | 3.17E-05 | 0.117 |
| YW508.20.06 | 2.50E+05 | 5.02E-05 | 0.201 |
| YW508.20.28b | 1.52E+05 | 4.90E-05 | 0.323 |
| YW508.20.33b | 1.57E+05 | 1.94E-06 | 0.0123 |
| YW508.20.84 | 1.92E+05 | 2.59E-05 | 0.135 |

FIGURE 3C

| YW508.20.33b | Ka (1/Ms) | Kd (1/s) | KD (pM) |
|---|---|---|---|
| Cyno | 2.62E+04 | 1.63E-06 | 62.4 |
| Rat | 6.81E+04 | 1.24E-06 | 18.2 |

FIGURE 3D

| | Ka (1/Ms) | Kd (1/s) | KD (nM) |
|---|---|---|---|
| YW508.20.33b | 8.35E+03 | 3.42E-05 | 4.09 |

ANTI-PCSK9 ANTIBODIES, FORMULATIONS, DOSING, AND METHODS OF USE

CROSS-REFERENCE TO RELATED PATENT APPLICATIONS

This application claims the priority benefit of U.S. provisional application Ser. Nos. 61/660,605, filed Jun. 15, 2012, and 61/786,280, filed Mar. 14, 2013, which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392014500SEQLIST.txt, date recorded: Jun. 13, 2013, size: 39 KB).

FIELD OF THE INVENTION

The present invention relates to anti-PCSK9 antibodies, antibody formulations, dosing regimens, and methods of using the same.

BACKGROUND OF THE INVENTION

Proprotein convertase subtilisin/kexin type 9 (PCSK9) is a member of the mammalian subtilisin family of proprotein convertases. PCSK9 plays a critical role in cholesterol metabolism by controlling the levels of low density lipoprotein (LDL) particles that circulate in the bloodstream. Elevated levels of PCSK9 have been shown to reduce LDL-receptor levels in the liver, resulting in high levels of LDL-cholesterol in the plasma and increased susceptibility to coronary artery disease. (Peterson et al., *J Lipid Res.* 49(7):1595-9 (2008)). Therefore, it would be highly advantageous to produce a therapeutic-based antagonist of PCSK9 that inhibits or antagonizes the activity of PCSK9 and the corresponding role PCSK9 plays in various therapeutic conditions.

SUMMARY OF THE INVENTION

The invention is in part based on a variety of antibodies to PCSK9. PCSK9 presents as an important and advantageous therapeutic target, and the invention provides antibodies as therapeutic and diagnostic agents for use in targeting pathological conditions associated with expression and/or activity of PCSK9. Accordingly, the invention provides methods, compositions, kits and articles of manufacture related to PCSK9.

In certain embodiments, an antibody or an antibody fragment that binds to PCSK9 or a fragment thereof is provided, wherein the antibody comprises a variable domain comprising at least one, two, three, four, five or six hypervariable region (HVR) sequences selected from the group consisting of:
  (i) HVR-H1 comprising GFTFX$_1$X$_2$X$_3$X$_4$IH (SEQ ID NO: 28), wherein X$_1$ is S or T; X$_2$ is G, R or S; X$_3$ is H, T or Y; X$_4$ is A or T;
  (ii) HVR-H2 comprising RISPANGNTNYADSVKG (SEQ ID NO:4);
  (iii) HVR-H3 comprising WIGSRELYIMDY (SEQ ID NO:5);
  (iv) HVR-L1 comprising RASQDVSX$_1$AVA (SEQ ID NO:29), wherein X$_1$ is S or T;
  (v) HVR-L2 comprising SASX$_1$LYS (SEQ ID NO:30), wherein X$_1$ is F or S; and
  (vi) HVR-L3 comprising QQSYX$_1$X$_2$X$_3$X$_4$T (SEQ ID NO:31) or QQAYX$_1$X$_2$X$_3$X$_4$T (SEQ ID NO:37), wherein X$_1$ is P, R or T; X$_2$ is A, I, S or T; X$_3$ is L, P or Q; X$_4$ is A, H, P or S.

In certain embodiments, an antibody or an antibody fragment that binds to PCSK9 or a fragment thereof is provided, wherein the antibody comprises a variable domain comprising the following six HVR sequences:
  (i) HVR-H1 comprising GFTFX$_1$X$_2$X$_3$X$_4$IH (SEQ ID NO:28), wherein X$_1$ is S or T; X$_2$ is G, or S; X$_3$ is H, T or Y; X$_4$ is A or T;
  (ii) HVR-H2 comprising RISPANGNTNYADSVKG (SEQ ID NO:4);
  (iii) HVR-H3 comprising WIGSRELYIMDY (SEQ ID NO:5);
  (iv) HVR-L1 comprising RASQDVSX$_1$AVA (SEQ ID NO:29), wherein X$_1$ is S or T;
  (v) HVR-L2 comprising SASX$_1$LYS (SEQ ID NO:30), wherein X$_1$ is F or S; and
  (vi) HVR-L3 comprising QQSYX$_1$X$_2$X$_3$X$_4$T (SEQ ID NO:31) or QQAYX$_1$X$_2$X$_3$X$_4$T (SEQ ID NO:37), wherein X$_1$ is P, R or T; X$_2$ is A, I, S or T; X$_3$ is L, P or Q; X$_4$ is A, H, P or S.

In certain embodiments, an antibody or an antibody fragment that binds to PCSK9 or a fragment thereof is provided, wherein the antibody comprises a variable domain comprising at least one, two, three, four, five or six hypervariable region (HVR) sequences selected from the group consisting of:
  (i) HVR-H1 comprising GFTFX$_1$X$_2$X$_3$X$_4$IX$_5$ (SEQ ID NO: 45), wherein X$_1$ is S or T; X$_2$ is G, R or S; X$_3$ is H, T or Y; X$_4$ is A or T; X$_5$ is H or N;
  (ii) HVR-H2 comprising RISPANGNTNYADSVKG (SEQ ID NO:4);
  (iii) HVR-H3 comprising WIGSRELYIMDY (SEQ ID NO:5);
  (iv) HVR-L1 comprising RASQDVSX$_1$AVA (SEQ ID NO:29), wherein X$_1$ is S or T;
  (v) HVR-L2 comprising SASX$_1$LYS (SEQ ID NO:30), wherein X$_1$ is F or S; and
  (vi) HVR-L3 comprising QQSYX$_1$X$_2$X$_3$X$_4$T (SEQ ID NO:31) or QQAYX$_1$X$_2$X$_3$X$_4$T (SEQ ID NO:37), wherein X$_1$ is P, R or T; X$_2$ is A, I, S or T; X$_3$ is L, P or Q; X$_4$ is A, H, P or S.

In certain embodiments, an antibody or an antibody fragment that binds to PCSK9 or a fragment thereof is provided, wherein the antibody comprises a variable domain comprising the following six HVR sequences:
  (i) HVR-H1 comprising GFTFX$_1$X$_2$X$_3$X$_4$IX$_5$ (SEQ ID NO: 45), wherein X$_1$ is S or T; X$_2$ is G, R or S; X$_3$ is H, T or Y; X$_4$ is A or T; X$_5$ is H or N;
  (ii) HVR-H2 comprising RISPANGNTNYADSVKG (SEQ ID NO:4);
  (iii) HVR-H3 comprising WIGSRELYIMDY (SEQ ID NO:5);
  (iv) HVR-L1 comprising RASQDVSX$_1$AVA (SEQ ID NO:29), wherein X$_1$ is S or T;
  (v) HVR-L2 comprising SASX$_1$LYS (SEQ ID NO:30), wherein X$_1$ is F or S; and
  (vi) HVR-L3 comprising QQSYX$_1$X$_2$X$_3$X$_4$T (SEQ ID NO:31) or QQAYX$_1$X$_2$X$_3$X$_4$T (SEQ ID NO:37), wherein X$_1$ is P, R or T; X$_2$ is A, I, S or T; X$_3$ is L, P or Q; X$_4$ is A, H, P or S.

In certain embodiments, an antibody or an antibody fragment that binds to PCSK9 or a fragment thereof is provided, wherein the antibody comprises a variable domain comprising at least one, two, three, four, five or six hypervariable region (HVR) sequences selected from the group consisting of:
- (i) HVR-H1 comprising GFTFX$_1$X$_2$X$_3$X$_4$IX$_5$ (SEQ ID NO: 45), wherein X$_1$ is S or T; X$_2$ is G, R or S; X$_3$ is H, T or Y; X$_4$ is A or T; X$_5$ is H or N;
- (ii) HVR-H2 comprising RISPANGNTNYADSVKG (SEQ ID NO:4);
- (iii) HVR-H3 comprising WIGSRELYIMDY (SEQ ID NO:5);
- (iv) HVR-L1 comprising RASQDVSTAVA (SEQ ID NO:7);
- (v) HVR-L2 comprising SASFLYS (SEQ ID NO:8); and
- (vi) HVR-L3 comprising QQSYX$_1$X$_2$X$_3$X$_4$T (SEQ ID NO:31) or QQAYX$_1$X$_2$X$_3$X$_4$T (SEQ ID NO:37), wherein X$_1$ is P, R or T; X$_2$ is A, I, S or T; X$_3$ is L, P or Q; X$_4$ is A, H, P or S.

In certain embodiments, an antibody or an antibody fragment that binds to PCSK9 or a fragment thereof is provided, wherein the antibody comprises a variable domain comprising the following six HVR sequences:
- (i) HVR-H1 comprising GFTFX$_1$X$_2$X$_3$X$_4$IX$_5$ (SEQ ID NO: 45), wherein X$_1$ is S or T; X$_2$ is G, R or S; X$_3$ is H, T or Y; X$_4$ is A or T; X$_5$ is H or N;
- (ii) HVR-H2 comprising RISPANGNTNYADSVKG (SEQ ID NO:4);
- (iii) HVR-H3 comprising WIGSRELYIMDY (SEQ ID NO:5);
- (iv) HVR-L1 comprising RASQDVSTAVA (SEQ ID NO:7);
- (v) HVR-L2 comprising SASFLYS (SEQ ID NO:8); and
- (vi) HVR-L3 comprising QQSYX$_1$X$_2$X$_3$X$_4$T (SEQ ID NO:31) or QQAYX$_1$X$_2$X$_3$X$_4$T (SEQ ID NO:37), wherein X$_1$ is P, R or T; X$_2$ is A, I, S or T; X$_3$ is L, P or Q; X$_4$ is A, H, P or S.

In certain embodiments, an antibody or an antibody fragment that binds to PCSK9 or a fragment thereof is provided, wherein the antibody comprises (a) HVR-H1 comprising the amino acid sequence of SEQ ID NO:1, SEQ ID NO:2, SEQ ID NO:3, or SEQ ID NO:42, (b) HVR-H2 comprising the amino acid sequence of SEQ ID NO:4, and (c) HVR-H3 comprising the amino acid sequence of SEQ ID NO:5. In certain embodiments, the antibody further comprises (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33.

In certain embodiments, an antibody or an antibody fragment that binds to PCSK9 or a fragment thereof is provided, wherein the antibody comprises (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO: 9, SEQ ID NO:10, SEQ ID NO:11, SEQ ID NO:12, SEQ ID NO:13, SEQ ID NO:14, or SEQ ID NO:33. In certain embodiments, the antibody further comprises (a) HVR-H1 comprising the amino acid sequence of SEQ ID NO:1, SEQ ID NO:2, SEQ ID NO:3, or SEQ ID NO:42, (b) HVR-H2 comprising the amino acid sequence of SEQ ID NO:4, and (c) HVR-H3 comprising the amino acid sequence of SEQ ID NO:5.

In one embodiment, an antibody or an antibody fragment that binds to PCSK9 or a fragment thereof is provided, wherein the antibody comprises:
- (1) an HVR-H1 comprising the amino acid sequence of SEQ ID NO:1;
- (2) an HVR-H2 comprising the amino acid sequence of SEQ ID NO:4;
- (3) an HVR-H3 comprising the amino acid sequence of SEQ ID NO:5;
- (4) an HVR-L1 comprising the amino acid sequence of SEQ ID NO:6;
- (5) an HVR-L2 comprising the amino acid sequence of SEQ ID NO:26; and
- (6) an HVR-L3 comprising the amino acid sequence of SEQ ID NO:9.

In one embodiment, an antibody or an antibody fragment that binds to PCSK9 or a fragment thereof is provided, wherein the antibody comprises:
- (1) an HVR-H1 comprising the amino acid sequence of SEQ ID NO:1;
- (2) an HVR-H2 comprising the amino acid sequence of SEQ ID NO:4;
- (3) an HVR-H3 comprising the amino acid sequence of SEQ ID NO:5;
- (4) an HVR-L1 comprising the amino acid sequence of SEQ ID NO:7;
- (5) an HVR-L2 comprising the amino acid sequence of SEQ ID NO:8; and
- (6) an HVR-L3 comprising the amino acid sequence of SEQ ID NO:9.

In one embodiment, an antibody or an antibody fragment that binds to PCSK9 or a fragment thereof is provided, wherein the antibody comprises:
- (1) an HVR-H1 comprising the amino acid sequence of SEQ ID NO:1;
- (2) an HVR-H2 comprising the amino acid sequence of SEQ ID NO:4;
- (3) an HVR-H3 comprising the amino acid sequence of SEQ ID NO:5;
- (4) an HVR-L1 comprising the amino acid sequence of SEQ ID NO:7;
- (5) an HVR-L2 comprising the amino acid sequence of SEQ ID NO:8; and
- (6) an HVR-L3 comprising the amino acid sequence of SEQ ID NO:10.

In another embodiment, an antibody or an antibody fragment that binds to PCSK9 or a fragment thereof is provided, wherein the antibody comprises:
- (1) an HVR-H1 comprising the amino acid sequence of SEQ ID NO:1;
- (2) an HVR-H2 comprising the amino acid sequence of SEQ ID NO:4;
- (3) an HVR-H3 comprising the amino acid sequence of SEQ ID NO:5;
- (4) an HVR-L1 comprising the amino acid sequence of SEQ ID NO:7;
- (5) an HVR-L2 comprising the amino acid sequence of SEQ ID NO:8; and
- (6) an HVR-L3 comprising the amino acid sequence of SEQ ID NO:11.

In another embodiment, an antibody or an antibody fragment that binds to PCSK9 or a fragment thereof is provided, wherein the antibody comprises:
- (1) an HVR-H1 comprising the amino acid sequence of SEQ ID NO:2;
- (2) an HVR-H2 comprising the amino acid sequence of SEQ ID NO:4;

(3) an HVR-H3 comprising the amino acid sequence of SEQ ID NO:5;
(4) an HVR-L1 comprising the amino acid sequence of SEQ ID NO:7;
(5) an HVR-L2 comprising the amino acid sequence of SEQ ID NO:8; and
(6) an HVR-L3 comprising the amino acid sequence of SEQ ID NO:12.

In another embodiment, an antibody or an antibody fragment that binds to PCSK9 or a fragment thereof is provided, wherein the antibody comprises:
(1) an HVR-H1 comprising the amino acid sequence of SEQ ID NO:42;
(2) an HVR-H2 comprising the amino acid sequence of SEQ ID NO:4;
(3) an HVR-H3 comprising the amino acid sequence of SEQ ID NO:5;
(4) an HVR-L1 comprising the amino acid sequence of SEQ ID NO:7;
(5) an HVR-L2 comprising the amino acid sequence of SEQ ID NO:8; and
(6) an HVR-L3 comprising the amino acid sequence of SEQ ID NO:12.

In another embodiment, an antibody or an antibody fragment that binds to PCSK9 or a fragment thereof is provided, wherein the antibody comprises:
(1) an HVR-H1 comprising the amino acid sequence of SEQ ID NO:3;
(2) an HVR-H2 comprising the amino acid sequence of SEQ ID NO:4;
(3) an HVR-H3 comprising the amino acid sequence of SEQ ID NO:5;
(4) an HVR-L1 comprising the amino acid sequence of SEQ ID NO:7;
(5) an HVR-L2 comprising the amino acid sequence of SEQ ID NO:8; and
(6) an HVR-L3 comprising the amino acid sequence of SEQ ID NO:13.

In another embodiment, an antibody or an antibody fragment that binds to PCSK9 or a fragment thereof is provided, wherein the antibody comprises:
(1) an HVR-H1 comprising the amino acid sequence of SEQ ID NO:3;
(2) an HVR-H2 comprising the amino acid sequence of SEQ ID NO:4;
(3) an HVR-H3 comprising the amino acid sequence of SEQ ID NO:5;
(4) an HVR-L1 comprising the amino acid sequence of SEQ ID NO:7;
(5) an HVR-L2 comprising the amino acid sequence of SEQ ID NO:8; and
(6) an HVR-L3 comprising the amino acid sequence of SEQ ID NO:33.

In another embodiment, an antibody or an antibody fragment that binds to PCSK9 or a fragment thereof is provided, wherein the antibody comprises:
(1) an HVR-H1 comprising the amino acid sequence of SEQ ID NO:1;
(2) an HVR-H2 comprising the amino acid sequence of SEQ ID NO:4;
(3) an HVR-H3 comprising the amino acid sequence of SEQ ID NO:5;
(4) an HVR-L1 comprising the amino acid sequence of SEQ ID NO:7;
(5) an HVR-L2 comprising the amino acid sequence of SEQ ID NO:8; and
(6) an HVR-L3 comprising the amino acid sequence of SEQ ID NO:14.

In certain embodiments, an antibody or an antibody fragment that binds to PCSK9 or a fragment thereof is provided, wherein the antibody comprises (a) a VH sequence having at least 95% sequence identity to the amino acid sequence of SEQ ID NO:15, SEQ ID NO:16, SEQ ID NO:17, SEQ ID NO:27, or SEQ ID NO:43; or (b) a VL sequence having at least 95% sequence identity to the amino acid sequence of SEQ ID NO: 18, SEQ ID NO:19, SEQ ID NO:20, SEQ ID NO:21, SEQ ID NO:22, SEQ ID NO:23, SEQ ID NO:34, or SEQ ID NO:44.

In certain embodiments, an antibody or an antibody fragment that binds to PCSK9 or a fragment thereof is provided, wherein the antibody comprises a VH sequence of SEQ ID NO:15, SEQ ID NO:16, SEQ ID NO:17, SEQ ID NO:27, or SEQ ID NO:43. In certain embodiments, the antibody further comprises a VL sequence of SEQ ID NO: 18, SEQ ID NO:19, SEQ ID NO:20, SEQ ID NO:21, SEQ ID NO:22, SEQ ID NO:23, SEQ ID NO:34, or SEQ ID NO:44.

In one embodiment, an antibody or an antibody fragment that binds to PCSK9 or a fragment thereof is provided, wherein the antibody comprises a VH sequence of SEQ ID NO:15 and a VL sequence of SEQ ID NO:18. In another embodiment, an antibody or an antibody fragment that binds to PCSK9 or a fragment thereof is provided, wherein the antibody comprises a VH sequence of SEQ ID NO:27 and a VL sequence of SEQ ID NO:44. In another embodiment, an antibody or an antibody fragment that binds to PCSK9 or a fragment thereof is provided, wherein the antibody comprises a VH sequence of SEQ ID NO:15 and a VL sequence of SEQ ID NO:19. In another embodiment, an antibody or an antibody fragment that binds to PCSK9 or a fragment thereof is provided, wherein the antibody comprises a VH sequence of SEQ ID NO:27 and a VL sequence of SEQ ID NO:19. In another embodiment, an antibody or an antibody fragment that binds to PCSK9 or a fragment thereof is provided, wherein the antibody comprises a VH sequence of SEQ ID NO:27 and a VL sequence of SEQ ID NO:20. In another embodiment, an antibody or an antibody fragment that binds to PCSK9 or a fragment thereof is provided, wherein the antibody comprises a VH sequence of SEQ ID NO:16 and a VL sequence of SEQ ID NO:21. In another embodiment, an antibody or an antibody fragment that binds to PCSK9 or a fragment thereof is provided, wherein the antibody comprises a VH sequence of SEQ ID NO:43 and a VL sequence of SEQ ID NO:21. In another embodiment, an antibody or an antibody fragment that binds to PCSK9 or a fragment thereof is provided, wherein the antibody comprises a VH sequence of SEQ ID NO:17 and a VL sequence of SEQ ID NO:22. In another embodiment, an antibody or an antibody fragment that binds to PCSK9 or a fragment thereof is provided, wherein the antibody comprises a VH sequence of SEQ ID NO:27 and a VL sequence of SEQ ID NO:23. In another embodiment, an antibody or an antibody fragment that binds to PCSK9 or a fragment thereof is provided, wherein the antibody comprises a VH sequence of SEQ ID NO:17 and a VL sequence of SEQ ID NO:34.

In certain embodiments, an antibody or an antibody fragment that binds to PCSK9 or a fragment thereof is provided, wherein the antibody binds to an epitope within a fragment of PCSK9. In certain embodiments, an antibody or an antibody fragment that binds to PCSK9 or a fragment thereof is provided, wherein the antibody binds to an epitope within a fragment of PCSK9 comprising amino acids 376 to 379 of human PCSK9 amino acid sequence of SEQ ID NO:24. In certain embodiments, the functional and/or structural epitope of an antibody according to this invention includes residue D238 of human PCSK9. In certain embodiments, the functional and/or structural epitope of an antibody according to this invention includes residue A239 of human PCSK9. In certain embodiments, the functional and/or structural epitope of an antibody according to this invention includes residues D238 and A239 of human PCSK9. In certain embodiments, the functional and/or structural epitope of an antibody according to this invention includes residue E366 of human PCSK9. In certain embodiments, the functional and/or structural epitope of an antibody according to this invention includes residue D367 of human PCSK9. In certain embodiments, the functional and/or structural epitope of an antibody according to this invention includes residues E366 and D367 of human PCSK9. In certain embodiments, the functional and/or structural epitope of an antibody according to this invention includes residue H391 of human PCSK9. In certain embodiments, the functional and/or structural epitope of an antibody according to this invention includes residues E366, D367 and H391 of human PCSK9. According to another embodiment, the functional and/or structural epitope of an antibody according to this invention includes residues A239 and H391 of human PCSK9. In certain embodiments, the functional and/or structural epitope of includes one or more of residues A239, A341, E366, D367 and H391 of human PCSK9. In certain embodiments, the functional and/or structural epitope of includes one or more of residues near A239, A341, E366, D367 and H391 of human PCSK9. In certain embodiments, the functional and/or structural epitope of an antibody according to this invention comprises (i) at least one residue selected from the group consisting of R194 and E195, (ii) at least one residue selected from the group consisting of D238 and A239, (iii) at least one residue selected from the group consisting of A341 and Q342, and (iv) at least one residue selected from the group consisting of E366, D367, I369, S376, T377, C378, F379, S381 and H391, of human PCSK9. In certain embodiments, the functional and/or structural epitope comprises one, two, three, four, five, six, seven, eight, nine, ten, eleven, twelve, thirteen, fourteen or all of the following residues: R194, E195, D238, A239, A341, Q342, E366, D367, I369, S376, T377, C378, F379, S381 and H391 of human PCSK9.

In certain embodiments, the anti-PCSK9 antibody is a monoclonal antibody. In certain embodiments, the anti-PCSK9 antibody is humanized. In certain embodiments, the anti-PCSK9 antibody is a human antibody. In certain embodiments, at least a portion of the framework sequence of the anti-PCSK9 antibody is a human consensus framework sequence. In one embodiment, the antibody is an antibody fragment selected from a Fab, Fab'-SH, Fv, scFv, or (Fab')$_2$ fragment.

In one aspect, a nucleic acid encoding any of the above anti-PCSK9 antibodies is provided. In one embodiment, a vector comprising the nucleic acid is provided. In one embodiment, the vector is an expression vector. In one embodiment, a host cell comprising the vector is provided. In one embodiment, the host cell is eukaryotic. In another embodiment, the host cell is mammalian. In yet another embodiment, the host cell is prokaryotic. In one embodiment, a method of making an anti-PCSK9 antibody is provided, wherein the method comprises culturing the host cell under conditions suitable for expression of the nucleic acid encoding the antibody, and isolating the antibody. In certain embodiment, the method further comprises recovering the anti-PCSK9 antibody from the host cell. In certain embodiments, a composition comprising any of the anti-PCSK9 antibodies described herein is provided. In one embodiment, the composition further comprises a pharmaceutically acceptable carrier.

In one aspect, provided herein is a pharmaceutical composition comprising an anti-PCSK9 antibody at about 100 to about 225 mg/mL, arginine succinate at about 180 to about 220 mM, polysorbate at about 0.01% to about 0.03%, and pH at about 5.2 to about 6.2. In certain embodiments, the anti-PCSK9 antibody or antibody fragment in the composition is at about 150 mg/mL, arginine succinate in the composition is at about 200 mM, and polysorbate 20 in the composition is about 0.02%, and pH at about 5.5. In certain embodiments, the composition is suitable for subcutaneous administration. In certain embodiments, the viscosity of the composition is less than about 10 cP at 25° C. Any anti-PCSK9 antibodies known in the art or described herein may be formulated into the composition.

In one aspect, provided herein is a pharmaceutical composition comprising an anti-PCSK9 antibody at about 150 to about 225 mg/mL, histidine acetate at about 10 to about 30 mM, arginine acetate at about 150 to about 170 mM, polysorbate at about 0.01% to about 0.03%, and pH at about 5.8 to about 6.2. In certain embodiments, the anti-PCSK9 antibody or antibody fragment in the composition is at about 200 mg/mL, histidine acetate in the composition is at about 20 mM, arginine acetate in the composition is at about 160 mM, and polysorbate 20 in the composition is about 0.02%, and pH at about 6.0. In certain embodiments, the composition is suitable for subcutaneous administration. In certain embodiments, the viscosity of the composition is less than about 10 cP at 25° C. Any anti-PCSK9 antibodies known in the art or described herein may be formulated into the composition.

In one aspect, provided herein is a subcutaneous administration device containing an anti-PCSK9 antibody or a composition comprising an anti-PCSK9 antibody described herein. In certain embodiments, the device is for delivering to an individual a flat dose in the range of about 200 to about 1200 mg of the antibody. In certain embodiments, the device is a pre-filled syringe (e.g., 0.5-mL, 1-mL, 1.25-mL, 1.5-mL, 1.75-mL, 2-mL, 2.25-mL, or 2.5-mL syringe). In certain embodiments, the device is a 1-mL pre-filled syringe and the antibody concentration in the pre-filled syringe is about 200 mg/mL. In certain embodiments, the device is a 1.5-mL pre-filled syringe and the antibody concentration in the pre-filled syringe is about 200 mg/mL. In certain embodiments, the device is a 2-mL pre-filled syringe and the antibody concentration in the pre-filled syringe is about 200 mg/mL. In certain embodiments, the device is a 2.25-mL pre-filled syringe and the antibody concentration in the pre-filled syringe is about 200 mg/mL. In certain embodiments, the device is a 2.5-mL pre-filled syringe and the antibody concentration in the pre-filled syringe is about 200 mg/mL.

In one aspect, the invention concerns methods of inhibiting binding of PCSK9 to LDL-receptor (LDLR) in a subject, said method comprising administering to the subject an effective amount of any of the anti-PCSK9 antibodies described herein. In another aspect, the invention concerns methods of reducing a level of cholesterol in a subject, said method comprising administering to the subject an effective amount of any of the anti-PCSK9 antibodies described herein. In one embodiment, the cholesterol is LDL-cholesterol. In another aspect, the invention concerns methods of reducing a level of LDL-cholesterol in a subject, said method comprising administering to the subject an effective amount of any of the anti-PCSK9 antibodies described herein. In certain embodiments, the invention concerns methods of lowering serum LDL-cholesterol level in a subject, said method comprising administering to the subject an effective amount of any one of the anti-PCSK9 antibodies described herein. In another aspect, the invention concerns methods of treating a condition associated with elevated level of LDL-cholesterol in a subject, said method comprising administering to the subject an effective amount of any one of the anti-PCSK9 antibodies described herein.

In one aspect, the invention concerns methods of treating a cholesterol related disorder. An exemplary and non-limiting list of cholesterol related disorders contemplated is provided herein under "Compositions and Methods." In certain embodiments, the cholesterol related disorder is hypercholesterolemia. In certain embodiments, the invention concerns methods of treating hypercholesterolemia comprising administering to the subject an effective amount of any one of the anti-PCSK9 antibodies described herein. In certain embodiments, the invention concerns methods of preventing and/or treating atherosclerosis and/or cardiovascular diseases. In certain embodiments, the invention concerns methods of reducing the risk of recurrent cardiovascular events in an individual comprising administering to the individual an amount effective of any one of the anti-PCSK9 antibodies described herein.

In one aspect, the invention concerns methods for treating any disease or condition which can be improved, ameliorated, inhibited or prevented by removal, inhibition or reduction of PCSK9 activity. In certain embodiments, diseases or disorders that are either treatable or preventable through the use of statins can also be treated using any one of the anti-PCSK9 antibodies described herein. In certain embodiments, disorders or disease that can benefit from the prevention of cholesterol synthesis or increased LDLR expression can also be treated using any one of the anti-PCSK9 antibodies described herein.

In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every two weeks, every month, every two months, or every three months. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every two weeks. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every month. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every two months. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every three months.

In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every two weeks, every month, every two months, or every three months. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every two weeks. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every month. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every two months. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every three months.

In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every 2 weeks, every 4 weeks, every 6 weeks, every 8 weeks, every 10 weeks, or every 12 weeks. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every 2 weeks. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every 4 weeks. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every 6 weeks. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every 8 weeks. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every 10 weeks. In certain embodiments of the methods described herein, the anti-PCSK9 antibody is administered subcutaneously at 200 mg, 220 mg, 380 mg, 400 mg, 600 mg, 760 mg, 800 mg, 1000 mg, 1140 mg, or 1200 mg per dose every 12 weeks.

In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every 2 weeks, every 4 weeks, every 6 weeks, every 8 weeks, every 10 weeks, or every 12 weeks. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every 2 weeks. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every 4 weeks. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every 6 weeks. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every 8 weeks. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every 10 weeks. In certain embodiments of the methods described herein, the anti-PCSK9 antibody is administered subcutaneously at 200-1200 mg, 200-1000 mg, 200-800 mg, 200-600 mg, 200-400 mg, 400-1200 mg, 400-1000 mg, 400-800 mg, 400-600 mg, 600-1200 mg, 600-1000 mg, 600-800 mg, 800-1200 mg, 800-1000 mg, 800-900 mg, 750-850 mg, 750-800 mg, 775-825 mg, 350-450 mg, 375-425 mg, or 375-400 mg per dose every 12 weeks.

In certain embodiments of the methods described herein, the anti-PCSK9 antibody is administered subcutaneously at 600 mg per dose every 8 weeks. In certain embodiments of the methods described herein, the anti-PCSK9 antibody is administered subcutaneously at 800 mg per dose every 8 weeks. In certain embodiments of the methods described herein, the anti-PCSK9 antibody is administered subcutaneously at 800 mg per dose every 10 weeks. In certain embodiments of the methods described herein, the anti-PCSK9 antibody is administered subcutaneously at 800 mg per dose every 12 weeks. In certain embodiments of the methods described herein, the anti-PCSK9 antibody is administered subcutaneously at 760 mg per dose every 8 weeks. In certain embodiments of the methods described herein, the anti-PCSK9 antibody is administered subcutaneously at 760 mg per dose every 10 weeks. In certain embodiments of the methods described herein, the anti-PCSK9 antibody is administered subcutaneously at 760 mg per dose every 12 weeks. In certain embodiments of the methods described herein, the anti-PCSK9 antibody is administered subcutaneously at 400 mg per dose every 4 weeks. In certain embodiments of the methods described herein, the anti-PCSK9 antibody is administered subcutaneously at 400 mg per dose every 8 weeks. In certain embodiments of the methods described herein, the anti-PCSK9 antibody is administered subcutaneously at 400 mg per dose every 12 weeks. In certain embodiments of the methods described herein, the anti-PCSK9 antibody is administered subcutaneously at 380 mg per dose every 4 weeks. In certain embodiments of the methods described herein, the anti-PCSK9 antibody is administered subcutaneously at 380 mg per dose every 8 weeks. In certain embodiments of the methods described herein, the anti-PCSK9 antibody is administered subcutaneously at 380 mg per dose every 12 weeks. In certain embodiments of the methods described herein, the anti-PCSK9 antibody is administered subcutaneously at 220 mg per dose every 2 weeks. In certain embodiments of the methods described herein, the anti-PCSK9 antibody is administered subcutaneously at 220 mg per dose every 4 weeks. In certain embodiments of the methods described herein, the anti-PCSK9 antibody is administered subcutaneously at 220 mg per dose every 8 weeks.

In certain embodiments of the methods described herein, subjects receiving the anti-PCSK9 antibody are monitored for LDL-c levels and if their levels drop below 25 or 15 mg/dL, then their dose is adjusted down to around 50% or 25% of the initial dose by adjusting the dose and/or frequency of administration. In certain embodiments of the methods described herein, a subject is administered an initial dose of 800 mg of anti-PCSK9 antibody every 8 weeks, the LDL-c levels of the subject are monitored and if the subject's LDL-c levels drop below 25 mg/dL, the dose is adjusted to 200 mg of anti-PCSK9 antibody every 8 weeks. In certain embodiments of the methods described herein, a subject is administered an initial dose of 800 mg of anti-PCSK9 antibody every 8 weeks, the LDL-c levels of the subject are monitored and if the subject's LDL-c levels drop below 15 mg/dL, the dose is adjusted to 200 mg of anti-PCSK9 antibody every 8 weeks. In certain embodiments of the methods described herein, a subject is administered an initial dose of 760 mg of anti-PCSK9 antibody every 8 weeks, the LDL-c levels of the subject are monitored and if the subject's LDL-c levels drop below 25 mg/dL, the dose is adjusted to 200 mg of anti-PCSK9 antibody every 8 weeks. In certain embodiments of the methods described herein, a subject is administered an initial dose of 760 mg of anti-PCSK9 antibody every 8 weeks, the LDL-c levels of the subject are monitored and if the subject's LDL-c levels drop below 15 mg/dL, the dose is adjusted to 200 mg of anti-PCSK9 antibody every 8 weeks. In certain embodiments of the methods described herein, a subject is administered an initial dose of 760 mg of anti-PCSK9 antibody every 8 weeks, the LDL-c levels of the subject are monitored and if the subject's LDL-c levels drop below 25 mg/dL, the dose is adjusted to 190 mg of anti-PCSK9 antibody every 8 weeks. In certain embodiments of the methods described herein, a subject is administered an initial dose of 760 mg of anti-PCSK9 antibody every 8 weeks, the LDL-c levels of the subject are monitored and if the subject's LDL-c levels drop below 15 mg/dL, the dose is adjusted to 190 mg of anti-PCSK9 antibody every 8 weeks. In certain embodiments of the methods described herein, a subject is administered an initial dose of 400 mg of anti-PCSK9 antibody every 4 weeks, the LDL-c levels of the subject are monitored and if the subject's LDL-c levels drop below 25 mg/dL, the dose is adjusted to 100 mg of anti-PCSK9 antibody every 4 weeks. In certain embodiments of the methods described herein, a subject is administered an initial dose of 400 mg of anti-PCSK9 antibody every 4 weeks, the LDL-c levels of the subject are monitored and if the subject's LDL-c levels drop below 15 mg/dL, the dose is adjusted to 100 mg of anti-PCSK9 antibody every 4 weeks. In certain embodiments of the methods described herein, a subject is administered an initial dose of 380 mg of anti-PCSK9 antibody every 4 weeks, the LDL-c levels of the subject are monitored and if the subject's LDL-c levels drop below 25 mg/dL, the dose is adjusted to 100 mg of anti-PCSK9 antibody every 4 weeks. In certain embodiments of the methods described herein, a subject is administered an initial dose of 380 mg of anti-PCSK9 antibody every 4 weeks, the LDL-c levels of the subject are monitored and if the subject's LDL-c levels drop below 15 mg/dL, the dose is adjusted to 100 mg of anti-PCSK9 antibody every 4 weeks.

In certain embodiments, any of the foregoing subcutaneous doses are administered using a subcutaneous administration device. In certain embodiments, the device is a pre-filled syringe (e.g., 0.5-mL, 1-mL, 1.25-mL, 1.5-mL, 1.75-mL, 2-mL, 2.25-mL, or 2.5-mL syringe). In certain embodiments, the device is a 1-mL pre-filled syringe and the antibody concentration in the pre-filled syringe is about 200 mg/mL. In certain embodiments, the device is a 1.5-mL pre-filled syringe and the antibody concentration in the pre-filled syringe is about 200 mg/mL. In certain embodiments, the device is a 2-mL pre-filled syringe and the antibody concentration in the pre-filled syringe is about 200 mg/mL. In certain embodiments, the device is a 2.25-mL pre-filled syringe and the antibody concentration in the pre-filled syringe is about 200 mg/mL. In certain embodiments, the device is a 2.5-mL pre-filled syringe and the antibody concentration in the pre-filled syringe is about 200 mg/mL. In certain embodiments, more than one syringe may be used to obtain the full flat dose, e.g., one syringe, two syringes, three syringes, or four syringes. In alternative embodiments, a high volume, single use, subcutaneous infusion device may be used to obtain the full flat dose, e.g., a dose that can administer 3 mL, 4 mL, 5 mL, 6 mL, 7 mL, 8 mL, 9 mL or 10 mL.

In certain embodiments, the dose is 800 mg and it is administered every 8 weeks using two 2.25 mL syringes containing an anti-PCSK9 antibody at 200 mg/mL concentration. In certain embodiments, the dose is 800 mg and it is administered every 8 weeks using three 2.25 mL syringes containing an anti-PCSK9 antibody at 200 mg/mL concentration. In certain embodiments, the dose is 800 mg and it is administered every 10 weeks using two 2.25 mL syringes containing an anti-PCSK9 antibody at 200 mg/mL concentration. In certain embodiments, the dose is 800 mg and it is administered every 10 weeks using three 2.25 mL syringes containing an anti-PCSK9 antibody at 200 mg/mL concentration. In certain embodiments, the dose is 800 mg and it is administered every 12 weeks using two 2.25 mL syringes containing an anti-PCSK9 antibody at 200 mg/mL concentration. In certain embodiments, the dose is 800 mg and it is administered every 12 weeks using three 2.25 mL syringes containing an anti-PCSK9 antibody at 200 mg/mL concentration. In certain embodiments, the dose is 800 mg and it is administered every 8 weeks using a high volume, single use, subcutaneous infusion device containing 4 mL of an anti-PCSK9 antibody at 200 mg/mL.

In certain embodiments, the dose is 760 mg and it is administered every 8 weeks using two 2.25 mL syringes containing an anti-PCSK9 antibody at 200 mg/mL concentration. In certain embodiments, the dose is 760 mg and it is administered every 10 weeks using two 2.25 mL syringes containing an anti-PCSK9 antibody at 200 mg/mL concentration. In certain embodiments, the dose is 760 mg and it is administered every 12 weeks using two 2.25 mL syringes containing an anti-PCSK9 antibody at 200 mg/mL concentration.

In certain embodiments, the dose is 600 mg and it is administered every 8 weeks using two 2.25 mL syringes containing an anti-PCSK9 antibody at 200 mg/mL concentration. In certain embodiments, the dose is 600 mg and it is administered every 12 weeks using two 2.25 mL syringes containing an anti-PCSK9 antibody at 200 mg/mL concentration.

In certain embodiments, the dose is 400 mg and it is administered every 4 weeks using one 2.5 mL syringe containing an anti-PCSK9 antibody at 200 mg/mL concentration. In certain embodiments, the dose is 400 mg and it is administered every 4 weeks using two 2.25 mL syringes containing an anti-PCSK9 antibody at 200 mg/mL concentration. In certain embodiments, the dose is 380 mg and it is administered every 4 weeks using one 2.25 mL syringe containing an anti-PCSK9 antibody at 200 mg/mL concentration.

In certain embodiments, the methods described herein further comprise administering to the subject an effective amount of a second medicament, wherein the anti-PCSK9 antibody is the first medicament. In one embodiment, the second medicament elevates the level of LDLR protein. In another embodiment, the second medicament reduces the level of LDL-cholesterol. In another embodiment, the second medicament comprises a statin. In another embodiment, the statin is selected from the group consisting of atorvastatin, fluvastatin, lovastatin, mevastatin, pitavastatin, pravastatin, rosuvastatin, simvastatin, and any combination thereof. In another embodiment, the second medicament elevates the level of HDL-cholesterol. In certain embodiments, the subject or the individual is human.

In one aspect, the invention concerns a method of detecting PCSK9 protein in a sample suspected of containing the PCSK9 protein, the method comprising (a) contacting the sample with the anti-PCSK9 antibody described herein; and (b) detecting formation of a complex between the anti-PCSK9 antibody and the PCSK9 protein. In one embodiment, the anti-PCSK9 antibody is detectably labeled.

Any embodiment described herein or any combination thereof applies to any and all anti-PCSK9 antibodies, methods and uses of the invention described herein.

BRIEF DESCRIPTION OF THE FIGURES

FIG. 1 shows heavy chain HVR sequences, H1 (SEQ ID NOS 1, 1, 1, 1, 1, 2, 42, 3, 3, 1, respectively, in order of appearance), H2 (all disclosed as SEQ ID NO: 4), and H3 (all disclosed as SEQ ID NO: 5), and light chain HVR sequences, L1 (SEQ ID NOS: 6, 7, 7, 7, 7, 7, 7, 7, 7 and 7, respectively, in order of appearance), L2 (SEQ ID NOS: 26, 8, 8, 8, 8, 8, 8, 8 and 8, respectively, in order of appearance) and L3 (SEQ ID NOS: 9, 9, 10, 10, 11, 12, 12, 13, 33 and 14, respectively, in order of appearance), of anti-PCSK9 antibodies.

FIG. 2A-B show the amino acid sequences of (A) the heavy chain variable domains (SEQ ID NOS: 15, 27, 15, 27, 27, 16, 43, 17, 17 and 27, respectively, in order of appearance) and (B) light chain variable domains (SEQ ID NOS: 18, 44, 19, 19, 20, 21, 21, 22, 34 and 23, respectively, in order of appearance) of anti-PCSK9 antibodies. Positions are numbered according to Kabat and hypervariable regions are boxed.

FIG. 3A-D show dissociation constants of the anti-PCSK9 antibodies (IgG) against (A) human PCSK9, (B) murine PCSK9, (C) cyno PCSK9 and rat PCSK9, and (D) rhesus PCSK9.

DETAILED DESCRIPTION OF EMBODIMENTS OF THE INVENTION

Figure 4:
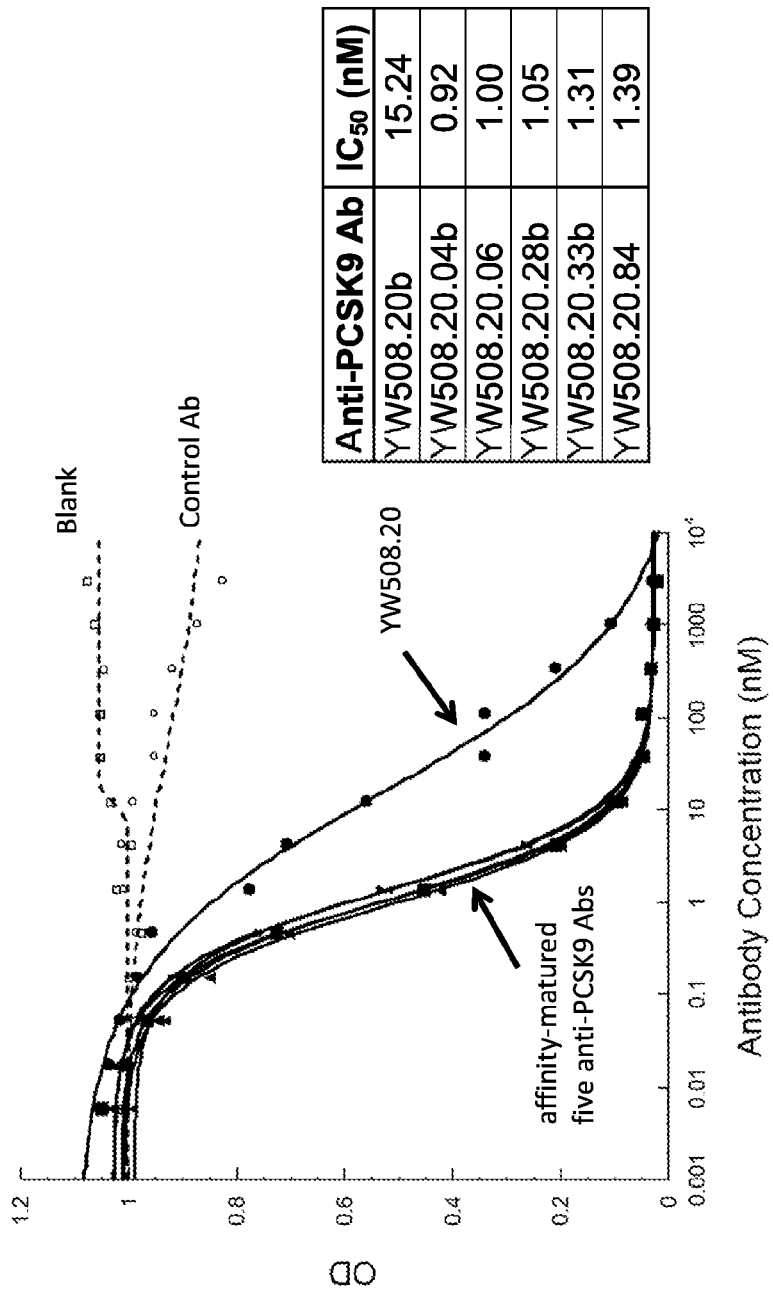
FIG. 4. Anti-PCSK9 antibodies inhibit binding of PCSK9 to LDLR in a competition binding ELISA. Blank (no antibody; open square) and control antibody (open circle) are shown in dashed lines. Anti-PCSK9 antibodies are shown in solid lines. $IC_{50}$ values of anti-PCSK9 antibodies are shown in the table.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G.

R. Taylor eds. (1995)), Harlow and Lane, eds. (1988) ANTI-BODIES, A LABORATORY MANUAL, and ANIMAL CELL CULTURE (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

I. DEFINITIONS

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety.

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

Throughout the present specification and claims, the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human $IgG_1$ EU antibody.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-PCSK9 antibody", "anti-PCSK9", "PCSK9 antibody" or "an antibody that binds to PCSK9" refers to an antibody that is capable of binding PCSK9 with sufficient affinity such that the antibody is useful as a diagnostic and/or therapeutic agent in targeting PCSK9. In one embodiment, the extent of binding of an anti-PCSK9 antibody to an unrelated, non-PCSK9 protein is less than about 10% of the binding of the antibody to PCSK9 as measured, e.g., by a radioimmunoassay (RIA). In certain embodiments, an antibody that binds to PCSK9 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-PCSK9 antibody binds to an epitope of PCSK9 that is conserved among PCSK9 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein. In certain embodiments, the epitope is determined based on the crystal structure of the anti-PCSK9 antibody Fab fragment bound to PCSK9.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The "Fab" fragment contains the heavy- and light-chain variable domains and also contains the constant domain of the light chain and the first constant domain ($CH_1$) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In certain embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypercholesterolemia," as used herein, refers to a condition in which cholesterol levels are elevated above a desired level. In certain embodiments, the LDL-cholesterol level is elevated above the desired level. In certain embodiments, the serum LDL-cholesterol levels are elevated above the desired level.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-PCSK9 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody," as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST®, BLAST-2, ALIGN or MEGALIGN™ (DNASTAR®) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX® UNIX operating system, including digital UNIX® V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "proprotein convertase subtilisin kexin type 9," "PCSK9," or "NARC-1," as used herein, refers to any native PCSK9 from any vertebrate source, including mammals such as primates (e.g. humans) and rodents (e.g., mice and rats), unless otherwise indicated. The term encompasses "full-length," unprocessed PCSK9 as well as any form of PCSK9 that results from processing in the cell or any fragment thereof. The term also encompasses naturally occurring variants of PCSK9, e.g., splice variants or allelic variants.

The term "PCSK9 activity" or "biological activity" of PCSK9, as used herein, includes any biological effect of PCSK9. In certain embodiments, PCSK9 activity includes the ability of PCSK9 to interact or bind to a substrate or receptor. In certain embodiments, the biological activity of PCSK9 is the ability of PCSK9 to bind to a LDL-receptor (LDLR). In certain embodiments, PCSK9 binds to and catalyzes a reaction involving LDLR. In certain embodiments, PCSK9 activity includes the ability of PCSK9 to decrease or reduce the availability of LDLR. In certain embodiments, the biological activity of PCSK9 includes the ability of PCSK9 to increase the amount of LDL in a subject. In certain embodiments, the biological activity of PCSK9 includes the ability of PCSK9 to decrease the amount of LDLR that is available to bind to LDL in a subject. In certain embodiments, the biological activity of PCSK9 includes the ability of PCSK9 to decrease the amount of LDLR that is available to bind to LDL. In certain embodiments, biological activity of PCSK9 includes any biological activity resulting from PCSK9 signaling.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the singular form "a", "an", and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

It is understood that aspect and embodiments of the invention described herein include "comprising," "consisting," and "consisting essentially of" aspects and embodiments.

II. COMPOSITIONS AND METHODS

In one aspect, the invention is based, in part, on experimental and clinical results obtained with anti-PCSK9 antibodies. Results obtained indicate that blocking biological activity of PCSK9 with anti-PCSK9 antibodies leads to a prevention of reduction in LDLR. In addition, the results demonstrate that administration of anti-PCSK9 antibody reduces total LDL-cholesterol level in a subject. Accordingly, PCSK9 antibodies of the invention, as described herein, provide important therapeutic and diagnostic agents for use in targeting pathological conditions associated with PCSK9, e.g., cholesterol related disorders.

In certain embodiments, a "cholesterol related disorder" includes any one or more of the following: hypercholesterolemia, heart disease, metabolic syndrome, diabetes, coronary heart disease, stroke, cardiovascular diseases, Alzheimers disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using an anti-PCSK9 antibody, either alone, or in combination with one or more other agents include the metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apolipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. Anti-PCSK9 antibodies described herein can also be useful in preventing or treating atherosclerotic diseases, such as, for example, coronary heart disease, coronary artery disease, peripheral arterial disease, stroke (ischaemic and hemorrhagic), angina pectoris, or cerebrovascular disease and acute coronary syndrome, myocardial infarction. In certain embodiments, the anti-PCSK9 antibodies described herein are useful in reducing the risk of: nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries. In certain embodiments, the anti-PCSK9 antibodies and methods described herein can be used to reduce the risk of recurrent cardiovascular events.

A. Exemplary Anti-PCSK9 Antibodies

In one aspect, the invention provides isolated antibodies that bind to PCSK9. In certain embodiments, an anti-PCSK9 antibody modulates PCSK9 activity.

In one aspect, the invention provides an anti-PCSK9 antibody comprising at least one, two, three, four, five, or six HVRs selected from (a) HVR-H1 comprising the amino acid sequence of SEQ ID NO:1, SEQ ID NO:2, SEQ ID NO:3, or SEQ ID NO:42; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:6 or SEQ ID NO:7; (e) HVR-L2 comprising the amino acid sequence of SEQ ID NO:8 or SEQ ID NO:26; and (f) HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33.

In one aspect, the invention provides an anti-PCSK9 antibody comprising six HVRs comprising (a) HVR-H1 comprising the amino acid sequence of SEQ ID NO:1, SEQ ID NO:2, SEQ ID NO:3, or SEQ ID NO:42; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:6 or SEQ ID NO:7; (e) HVR-L2 comprising the amino acid sequence of SEQ ID NO:8 or SEQ ID NO:26; and (f) HVR-L3 comprising the amino acid sequence of SEQ ID NO:9, SEQ ID NO:10, SEQ ID NO:11, SEQ ID NO:12, SEQ ID NO:13, SEQ ID NO:14 or SEQ ID NO:33.

In one aspect, the invention provides an antibody comprising at least one, at least two, or all three VH HVR sequences selected from (a) HVR-H1 comprising the amino acid sequence of SEQ ID NO:1, SEQ ID NO:2, SEQ ID NO:3, or SEQ ID NO:42; (b) HVR-H2 comprising the amino acid sequence of SEQ ID NO:4; and (c) HVR-H3 comprising the amino acid sequence of SEQ ID NO:5. In one embodiment, the antibody comprises HVR-H3 comprising the amino acid sequence of SEQ ID NO:5. In another embodiment, the antibody comprises HVR-H3 comprising the amino acid sequence of SEQ ID NO:5 and HVR-L3 comprising the amino acid sequence of SEQ ID NO:9, SEQ ID NO:10, SEQ ID NO:11, SEQ ID NO:12, SEQ ID NO:13, SEQ ID NO:14 or SEQ ID NO:33. In a further embodiment, the antibody comprises HVR-H3 comprising the amino acid sequence of SEQ ID NO:5, HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33, and HVR-H2 comprising the amino acid sequence of SEQ ID NO:4. In a further embodiment, the antibody comprises (a) HVR-H1 comprising the amino acid sequence of SEQ ID NO:1, SEQ ID NO:2, SEQ ID NO:3, or SEQ ID NO:42; (b) HVR-H2 comprising the amino acid sequence of SEQ ID NO:4; and (c) HVR-H3 comprising the amino acid sequence of SEQ ID NO:5.

In another aspect, the invention provides an antibody comprising at least one, at least two, or all three VL HVR sequences selected from (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33. In one embodiment, the antibody comprises (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33.

In another aspect, an antibody of the invention comprises (a) a VH domain comprising at least one, at least two, or all three VH HVR sequences selected from (i) HVR-H1 comprising the amino acid sequence of SEQ ID NO:1, SEQ ID NO:2, SEQ ID NO:3, or SEQ ID NO:42, (ii) HVR-H2 comprising the amino acid sequence of SEQ ID NO:4, and (iii) HVR-H3 comprising an amino acid sequence selected from SEQ ID NO:5; and (b) a VL domain comprising at least one, at least two, or all three VL HVR sequences selected from (i) HVR-L1 comprising the amino acid sequence of SEQ ID NO:6 or SEQ ID NO:7, (ii) HVR-L2 comprising the amino acid sequence of SEQ ID NO:8 or SEQ ID NO:26, and (c) HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33.

In another aspect, the invention provides an antibody comprising (a) HVR-H1 comprising the amino acid sequence of SEQ ID NO:1; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:6; (e) HVR-L2 comprising the amino acid sequence of SEQ ID NO:26; and (f) HVR-L3 comprising an amino acid sequence of SEQ ID NO:9. In another aspect, the invention provides an antibody comprising (a) HVR-H1 comprising the amino acid sequence of SEQ ID NO:1; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:7; (e) HVR-L2 comprising the amino acid sequence of SEQ ID NO:8; and (f) HVR-L3 comprising an amino acid sequence of SEQ ID NO:9. In another aspect, the invention provides an antibody comprising (a) HVR-H1 comprising the amino acid sequence of SEQ ID NO:1; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:7; (e) HVR-L2 comprising the amino acid sequence of SEQ ID NO:8; and (f) HVR-L3 comprising an amino acid sequence of SEQ ID NO:10. In another aspect, the invention provides an antibody comprising (a) HVR-H1 comprising the amino acid sequence of SEQ ID NO:1; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:7; (e) HVR-L2 comprising the amino acid sequence of SEQ ID NO:8; and (f) HVR-L3 comprising an amino acid sequence of SEQ ID NO:11. In another aspect, the invention provides an antibody comprising (a) HVR-H1 comprising the amino acid sequence of SEQ ID NO:2; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:7; (e) HVR-L2 comprising the amino acid sequence of SEQ ID NO:8; and (f) HVR-L3 comprising an amino acid sequence of SEQ ID NO:12. In another aspect, the invention provides an antibody comprising (a) HVR-H1 comprising the amino acid sequence of SEQ ID NO:42; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:7; (e) HVR-L2 comprising the amino acid sequence of SEQ ID NO:8; and (f) HVR-L3 comprising an amino acid sequence of SEQ ID NO:12. In another aspect, the invention provides an antibody comprising (a) HVR-H1 comprising the amino acid sequence of SEQ ID NO:3; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:7; (e) HVR-L2 comprising the amino acid sequence of SEQ ID NO:8; and (f) HVR-L3 comprising an amino acid sequence of SEQ ID NO:13. In another aspect, the invention provides an antibody comprising (a) HVR-H1 comprising the amino acid sequence of SEQ ID NO:1; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:7; (e) HVR-L2 comprising the amino acid sequence of SEQ ID NO:8; and (f) HVR-L3 comprising an amino acid sequence of SEQ ID NO:14. In another aspect, the invention provides an antibody comprising (a) HVR-H1 comprising the amino acid sequence of SEQ ID NO:3; (b) HVR-H2 comprising the amino acid sequence of SEQ ID NO:4; (c) HVR-H3 comprising the amino acid sequence of SEQ ID NO:5; (d) HVR-L1 comprising the amino acid sequence of SEQ ID NO:7; (e) HVR-L2 comprising the amino acid sequence of SEQ ID NO:8; and (f) HVR-L3 comprising an amino acid sequence of SEQ ID NO:33.

In certain embodiments, the anti-PCSK9 antibody is humanized. In one embodiment, an anti-PCSK9 antibody comprises HVRs as in any of the above embodiments, and further comprises an acceptor human framework, e.g., a human immunoglobulin framework or a human consensus framework.

In another aspect, an anti-PCSK9 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:15, SEQ ID NO:16, SEQ ID NO:17, SEQ ID NO:27, or SEQ ID NO:43. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PCSK9 antibody comprising that sequence retains the ability to bind to PCSK9. In certain embodiments, a total of 1 to 10 amino acids have been substituted, inserted and/or deleted in SEQ ID NO:15, SEQ ID NO:16, SEQ NO:17, SEQ ID NO:27, or SEQ ID NO:43. In certain embodiments, substitutions, insertions, or deletions occur in regions outside the HVRs (i.e., in the FRs). Optionally, the anti-PCSK9 antibody comprises the VH sequence in SEQ ID NO:15, SEQ ID NO:16, SEQ ID NO:17, SEQ ID NO:27, or SEQ ID NO:43, including post-translational modifications of that sequence. In a particular embodiment, the VH comprises one, two or three HVRs selected from: (a) HVR-H1 comprising the amino acid sequence of SEQ ID NO:1, SEQ ID NO:2, SEQ ID NO:3, or SEQ ID NO:42, (b) HVR-H2 comprising the amino acid sequence of SEQ ID NO:4, and (c) HVR-H3 comprising the amino acid sequence of SEQ ID NO:5.

In another aspect, an anti-PCSK9 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:18, SEQ ID NO:19, SEQ ID NO:20, SEQ ID NO:21, SEQ ID NO:22, SEQ ID NO:23, SEQ ID NO:34, or SEQ ID NO:44. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PCSK9 antibody comprising that sequence retains the ability to bind to PCSK9. In certain embodiments, a total of 1 to 10 amino acids have been substituted, inserted and/or deleted in SEQ ID NO:18, SEQ ID NO:19, SEQ ID NO:20, SEQ ID NO:21, SEQ ID NO:22, SEQ ID NO:23, SEQ ID NO:34, or SEQ ID NO:44. In certain embodiments, the substitutions, insertions, or deletions occur in regions outside the HVRs (i.e., in the FRs). Optionally, the anti-PCSK9 antibody comprises the VL sequence in SEQ ID NO:18, SEQ ID NO:19, SEQ ID NO:20, SEQ ID NO:21, SEQ ID NO:22, SEQ ID NO:23, SEQ ID NO:34, or SEQ ID NO:44, including post-translational modifications of that sequence. In a particular embodiment, the VL comprises one, two or three HVRs selected from (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33.

In another aspect, an anti-PCSK9 antibody is provided, wherein the antibody comprises a VH as in any of the embodiments provided above, and a VL as in any of the embodiments provided above. In one embodiment, the antibody comprises the VH and VL sequences in SEQ ID NO:15 and SEQ ID NO:18, respectively, including post-translational modifications of those sequences. In one embodiment, the antibody comprises the VH and VL sequences in SEQ ID NO:27 and SEQ ID NO:44, respectively, including post-translational modifications of those sequences. In one embodiment, the antibody comprises the VH and VL sequences in SEQ ID NO:15 and SEQ ID NO:19, respectively, including post-translational modifications of those sequences. In one embodiment, the antibody comprises the VH and VL sequences in SEQ ID NO:27 and SEQ ID NO:19, respectively, including post-translational modifications of those sequences. In one embodiment, the antibody comprises the VH and VL sequences in SEQ ID NO:27 and SEQ ID NO:20, respectively, including post-translational modifications of those sequences. In one embodiment, the antibody comprises the VH and VL sequences in SEQ ID NO:16 and SEQ ID NO:21, respectively, including post-translational modifications of those sequences. In one embodiment, the antibody comprises the VH and VL sequences in SEQ ID NO:43 and SEQ ID NO:21, respectively, including post-translational modifications of those sequences. In one embodiment, the antibody comprises the VH and VL sequences in SEQ ID NO:17 and SEQ ID NO:22, respectively, including post-translational modifications of those sequences. In one embodiment, the antibody comprises the VH and VL sequences in SEQ ID NO:27 and SEQ ID NO:23, respectively, including post-translational modifications of those sequences. In one embodiment, the antibody comprises the VH and VL sequences in SEQ ID NO:17 and SEQ ID NO:34, respectively, including post-translational modifications of those sequences.

In another aspect, an anti-PCSK9 antibody comprises a heavy chain sequence having at least 90%, 91%, 92%, 93%, 94%, 95%, 96%, 97%, 98%, 99%, or 100% sequence identity to the amino acid sequence of SEQ ID NO:35. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PCSK9 antibody comprising that sequence retains the ability to bind to PCSK9. In certain embodiments, a total of 1 to 10 amino acids have been substituted, inserted and/or deleted in SEQ ID NO:35. In certain embodiments, substitutions, insertions, or deletions occur in regions outside the HVRs (i.e., in the FRs). Optionally, the anti-PCSK9 antibody heavy chain comprises the VH sequence in SEQ ID NO:15, SEQ ID NO:16, SEQ ID NO:17, SEQ ID NO:27, or SEQ ID NO:43, including post-translational modifications of that sequence. In a particular embodiment, the heavy chain comprises one, two or three HVRs selected from: (a) HVR-H1 comprising the amino acid sequence of SEQ ID NO:1, SEQ ID NO:2, SEQ ID NO:3, or SEQ ID NO:42, (b) HVR-H2 comprising the amino acid sequence of SEQ ID NO:4, and (c) HVR-H3 comprising the amino acid sequence of SEQ ID NO:5.

In another aspect, an anti-PCSK9 antibody is provided, wherein the antibody comprises a light chain having at least 90%, 91%, 92%, 93%, 94%, 95%, 96%, 97%, 98%, 99%, or 100% sequence identity to the amino acid sequence of SEQ ID NO:36. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PCSK9 antibody comprising that sequence retains the ability to bind to PCSK9. In certain embodiments, a total of 1 to 10 amino acids have been substituted, inserted and/or deleted in SEQ ID NO:36. In certain embodiments, the substitutions, insertions, or deletions occur in regions outside the HVRs (i.e., in the FRs). Optionally, the anti-PCSK9 antibody light chain comprises the VL sequence in SEQ ID NO:18, SEQ ID NO:19, SEQ ID NO:20, SEQ ID NO:21, SEQ ID NO:22, SEQ ID NO:23, SEQ ID NO:34, or SEQ ID NO:44, including post-translational modifications of that sequence. In a particular embodiment, the light chain comprises one, two or three HVRs selected from (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33.

In another aspect, an anti-PCSK9 antibody is provided, wherein the antibody comprises a heavy chain as in any of the embodiments provided above, and a light chain as in any of the embodiments provided above. In one embodiment, the antibody comprises a heavy chain comprising the amino acid sequence of SEQ ID NO:35, and a light chain comprising the amino acid sequence of SEQ ID NO:36. In certain embodiments, SEQ ID NO:35 is truncated by one or two amino acids at the C-terminus, e.g., it does not contain K451, or G450 and K451. In certain embodiments, P449 in SEQ ID NO:35 is amidated.

```
Antibody 508.20.33b heavy chain amino acid sequence
(SEQ ID NO: 35):
EVQLVESGGGLVQPGGSLRLSCAASGFTFSSTAIHWVRQAPGKGLEWVARISPANGNTN

YADSVKGRFTISADTSKNTAYLQMNSLRAEDTAVYYCARWIGSRELYIMDYWGQGTLV

TVSSASTKGPSVFPLAPSSKSTSGGTAALGCLVKDYFPEPVTVSWNSGALTSGVHTFPAV
```

```
-continued
LQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

Antibody 508.20.33b light chain amino acid sequence
(SEQ ID NO: 36):
DIQMTQSPSSLSASVGDRVTITCRASQDVSTAVAWYQQKPGKAPKLLIYSASFLYSGVPS

RFSGSGSGTDFTLTISSLQPEDFATYYCQQAYPALHTFGQGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC
```

In certain embodiments, SEQ ID NO:35 is truncated by one or two amino acids at the C-terminus, e.g., it does not contain K451, or G450 and K451 (e.g., the heavy chain comprises amino acids 1-449 of SEQ ID NO:35 or amino acids 1-450 of SEQ ID NO:35). In certain embodiments, P449 in SEQ ID NO:35 is amidated.

In certain embodiments, functional epitopes can be mapped by combinatorial alanine scanning. In this process, a combinatorial alanine-scanning strategy can be used to identify amino acids in the PCSK9 protein that are necessary for interaction with anti-PCSK9 antibodies. In certain embodiments, the epitope is conformational and crystal structure of anti-PCSK9 antibody Fab fragment bound to PCSK9 may be employed to identify the epitopes. In one aspect, the invention provides an antibody that binds to the same epitope as any of the anti-PCSK9 antibody provided herein. For example, in certain embodiments, an antibody is provided that binds to the same epitope as an anti-PCSK9 antibody comprising a VH sequence of SEQ ID NO:15 and a VL sequence of SEQ ID NO:19. In certain embodiments, an antibody is provided that binds to the same epitope as an anti-PCSK9 antibody comprising a VH sequence of SEQ ID NO:27 and a VL sequence of SEQ ID NO:19. In certain embodiments, an antibody is provided that binds to the same epitope as an anti-PCSK9 antibody comprising a VH sequence of SEQ ID NO:27 and a VL sequence of SEQ ID NO:20. In certain embodiments, an antibody is provided that binds to the same epitope as an anti-PCSK9 antibody comprising a VH sequence of SEQ ID NO:16 and a VL sequence of SEQ ID NO:21. In certain embodiments, an antibody is provided that binds to the same epitope as an anti-PCSK9 antibody comprising a VH sequence of SEQ ID NO:43 and a VL sequence of SEQ ID NO:21. In certain embodiments, an antibody is provided that binds to the same epitope as an anti-PCSK9 antibody comprising a VH sequence of SEQ ID NO:17 and a VL sequence of SEQ ID NO:22. In certain embodiments, an antibody is provided that binds to the same epitope as an anti-PCSK9 antibody comprising a VH sequence of SEQ ID NO:27 and a VL sequence of SEQ ID NO:23. In certain embodiments, an antibody is provided that binds to the same epitope as an anti-PCSK9 antibody comprising a VH sequence of SEQ ID NO:17 and a VL sequence of SEQ ID NO:34.

In one aspect, the invention provides an anti-PCSK9 antibody, or antigen binding fragment thereof, that binds to human PCSK9 competitively with any one of the antibodies described herein. In certain embodiments, competitive binding may be determined using an ELISA assay. For example, in certain embodiments, an antibody is provided that binds to PCSK9 competitively with an anti-PCSK9 antibody comprising a VH sequence of SEQ ID NO:15 and a VL sequence of SEQ ID NO:19. In certain embodiments, an antibody is provided that binds to PCSK9 competitively with an anti-PCSK9 antibody comprising a VH sequence of SEQ ID NO:27 and a VL sequence of SEQ ID NO:19. In certain embodiments, an antibody is provided that binds to PCSK9 competitively with an anti-PCSK9 antibody comprising a VH sequence of SEQ ID NO:27 and a VL sequence of SEQ ID NO:20. In certain embodiments, an antibody is provided that binds to PCSK9 competitively with an anti-PCSK9 antibody comprising a VH sequence of SEQ ID NO:16 and a VL sequence of SEQ ID NO:21. In certain embodiments, an antibody is provided that binds to PCSK9 competitively with an anti-PCSK9 antibody comprising a VH sequence of SEQ ID NO:43 and a VL sequence of SEQ ID NO:21. In certain embodiments, an antibody is provided that binds to PCSK9 competitively with an anti-PCSK9 antibody comprising a VH sequence of SEQ ID NO:17 and a VL sequence of SEQ ID NO:22. In certain embodiments, an antibody is provided that binds to PCSK9 competitively with an anti-PCSK9 antibody comprising a VH sequence of SEQ ID NO:27 and a VL sequence of SEQ ID NO:23. In certain embodiments, an antibody is provided that binds to PCSK9 competitively with an anti-PCSK9 antibody comprising a VH sequence of SEQ ID NO:17 and a VL sequence of SEQ ID NO:34.

In certain embodiments, an antibody is provided that binds to an epitope within a fragment of PCSK9 as described herein. In certain embodiments, an antibody is provided that binds to an epitope within a fragment of PCSK9 comprising amino acids 376 to 379 of human PCSK9 amino acid sequence of SEQ ID NO:24. In certain embodiments, the functional and/or structural epitope of an antibody according to this invention includes residue D238 of human PCSK9. In certain embodiments, the functional and/or structural epitope of an antibody according to this invention includes residue A239 of human PCSK9. In certain embodiments, the functional and/or structural epitope of an antibody according to this invention includes residues D238 and A239 of human PCSK9. In certain embodiments, the functional and/or structural epitope of an antibody according to this invention includes residue E366 of human PCSK9. In certain embodiments, the functional and/or structural epitope of an antibody according to this invention includes residue D367 of human PCSK9. In certain embodiments, the functional and/or structural epitope of an antibody according to this invention includes residues E366 and D367 of human PCSK9. In certain embodiments, the functional and/or structural epitope of an antibody according to this invention includes residue H391 of human PCSK9. In certain embodiments, the functional and/or structural epitope of an antibody according to this invention includes residues E366, D367 and H391 of human PCSK9. According to another embodiment, the functional and/or structural epitope of an antibody according to this invention includes residues A239 and H391 of human PCSK9. In certain embodiments, the functional and/or structural epitope of includes one or more of residues A239, A341, E366, D367 and H391 of human PCSK9. In certain embodiments, the functional and/or structural epitope of includes one or more of residues near A239, A341, E366, D367 and H391 of human PCSK9. In certain embodiments, the functional and/or structural epitope of an antibody according to this invention comprises (i) at least one residue selected from the group consisting of R194 and E195, (ii) at least one residue selected from the group consisting of D238 and A239, (iii) at least one residue selected from the group consisting of A341 and Q342, and (iv) at least one residue selected from the group consisting of E366, D367, I369, S376, T377, C378, F379, S381 and H391, of human PCSK9. In certain embodiments, the functional and/or structural epitope comprises one, two, three, four, five, six, seven, eight, nine, ten, eleven, twelve, thirteen, fourteen or all of the following residues: R194, E195, D238, A239, A341, Q342, E366, D367, I369, S376, T377, C378, F379, S381 and H391 of human PCSK9.

In a further aspect of the invention, an anti-PCSK9 antibody according to any of the above embodiment is a monoclonal antibody, including a chimeric, humanized or human antibody. In one embodiment, an anti-PCSK9 antibody is an antibody fragment, e.g., a Fv, Fab, Fab', scFv, diabody, or F(ab')$_2$ fragment. In another embodiment, the antibody is a full length antibody, e.g., an intact IgG$_1$ antibody or other antibody class or isotype as defined herein.

In a further aspect, an anti-PCSK9 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J Mal. Biol.* 293:86S-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* S7:4S93-4S99 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN®-20) in PBS. When the plates have dried, 150 μl/well of scintillant (MICROSCINT™-20; Packard) is added, and the plates are counted on a TOPCOUNT® gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CMS chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN®-20) surfactant (PBST) at 25° C. at a flow rate of approximately 25 Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J Mal. Biol.* 293:865-881 (1999). If the on-rate exceeds $10^6$ M$^{-1}$s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO® spectrophotometer (Thermo Spectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for PCSK9 and the other is for any other antigen. In certain embodiments, bispecific antibodies may bind to two different epitopes of PCSK9. Bispecific antibodies may also be used to localize cytotoxic agents to cells which express PCSK9. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to PCSK9 as well as another, different antigen (see, e.g., US 2008/0069820).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table A under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE A

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγRIII binding (hence likely lacking ADCC activity), but retains FcRn binding ability. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J Exp. Med.* 166:1351-1361 (1987)). Alternatively, non-radioactive assays methods may be employed (see, for example, ACT 1™ non-radioactive cytotoxicity assay for flow cytometry (CellTechnology, Inc. Mountain View, Calif.; and CYTO-TOX 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Anti-PCSK9 antibodies described herein may be produced using recombinant methods and compositions, e.g., as described in U.S. Pat. No. 4,816,567. In one embodiment, isolated nucleic acid encoding an anti-PCSK9 antibody described herein is provided. Such nucleic acid may encode an amino acid sequence comprising the VL and/or an amino acid sequence comprising the VH of the antibody (e.g., the light and/or heavy chains of the antibody). In certain embodiments, an isolated nucleic acid encoding an anti-PCSK9 heavy chain variable region is provided wherein the nucleic acid comprises a sequence having at least 90%, 91%, 92%, 93%, 94%, 95%, 96%, 97%, 98%, 99%, or 100% sequence identity to the nucleic acid sequence of SEQ ID NO:38 or SEQ ID NO:39. In certain embodiments, an isolated nucleic acid encoding an anti-PCSK9 light chain variable region is provided wherein the nucleic acid comprises a sequence having at least 90%, 91%, 92%, 93%, 94%, 95%, 96%, 97%, 98%, 99%, or 100% sequence identity to the nucleic acid sequence of SEQ ID NO:40 or SEQ ID NO:41. In certain embodiments, an isolated nucleic acid encoding an anti-PCSK9 heavy chain variable region and an anti-PCSK9 light chain variable region is provided, wherein the nucleic acid encoding the heavy chain variable region comprises a sequence having at least 90%, 91%, 92%, 93%, 94%, 95%, 96%, 97%, 98%, 99%, or 100% sequence identity to the nucleic acid sequence of SEQ ID NO:38 or SEQ ID NO:39 and the nucleic acid encoding the light chain variable region comprises a sequence having at least 90%, 91%, 92%, 93%, 94%, 95%, 96%, 97%, 98%, 99%, or 100% sequence identity to the nucleic acid sequence of SEQ ID NO:40 or SEQ ID NO:41. In certain embodiments, an isolated nucleic acid encoding an anti-PCSK9 heavy chain variable region is provided wherein the nucleic acid comprises SEQ ID NO: 38 or 39. In certain embodiments, an isolated nucleic acid encoding an anti-PCSK9 light chain variable region is provided wherein the nucleic acid comprises SEQ ID NO: 40 or 41. In certain embodiments, an isolated nucleic acid encoding an anti-PCSK9 heavy chain variable region and light chain variable region is provided, wherein the nucleic acid encoding the heavy chain comprises SEQ ID NO:38 and the nucleic acid encoding the light chain comprises SEQ ID NO:40. In certain embodiments, an isolated nucleic acid encoding an anti-PCSK9 heavy chain variable region and light chain variable region is provided, wherein the nucleic acid encoding the heavy chain comprises SEQ ID NO:39 and the nucleic acid encoding the light chain comprises SEQ ID NO:41.

```
Antibody 508.20.33b Full Length Heavy Chain Nucleic Acid Sequence
                                                          (SEQ ID NO: 38)
GAA GTTCAGCTGG TGGAGTCTGG CGGTGGCCTG GTGCAGCCAG GGGGCTCACT CCGTTTGTCC

TGTGCAGCTT CTGGCTTCAC CTTCTCTAGT ACTGCTATTC ACTGGGTGCG TCAGGCCCCG GGTAAGGGCC

TGGAATGGGT TGCTAGGATT TCTCCTGCTA ACGGTAATAC TAACTATGCC GATAGCGTCA AGGGCCGTTT

CACTATAAGC GCAGACACAT CCAAAAACAC AGCCTACCTA CAAATGAACA GCTTAAGAGC TGAGGACACT

GCCGTCTATT ATTGTGCTCG TTGGATCGGG TCCCGGGAGC TGTACATTAT GGACTACTGG GGTCAAGGAA

CCCTGGTCAC CGTCTCCTCG GCCTCCACCA AGGGCCCATC GGTCTTCCCC CTGGCACCCT CCTCCAAGAG

CACCTCTGGG GGCACAGCGG CCCTGGGCTG CCTGGTCAAG GACTACTTCC CCGAACCGGT GACGGTGTCG

TGGAACTCAG GCGCCCTGAC CAGCGGCGTG CACACCTTCC CGGCTGTCCT ACAGTCCTCA GGACTCTACT

CCCTCAGCAG CGTGGTGACT GTGCCCTCTA GCAGCTTGGG CACCCAGACC TACATCTGCA ACGTGAATCA

CAAGCCCAGC AACACCAAGG TGGACAAGAA AGTTGAGCCC AAATCTTGTG ACAAAACTCA CACATGCCCA

CCGTGCCCAG CACCTGAACT CCTGGGGGGA CCGTCAGTCT TCCTCTTCCC CCCAAAACCC AAGGACACCC

TCATGATCTC CCGGACCCCT GAGGTCACAT GCGTGGTGGT GGACGTGAGC CACGAAGACC CTGAGGTCAA

GTTCAACTGG TACGTGGACG GCGTGGAGGT GCATAATGCC AAGACAAAGC CGCGGGAGGA GCAGTACAAC

AGCACGTACC GTGTGGTCAG CGTCCTCACC GTCCTGCACC AGGACTGGCT GAATGGCAAG GAGTACAAGT

GCAAGGTCTC CAACAAAGCC CTCCCAGCCC CCATCGAGAA AACCATCTCC AAAGCCAAAG GGCAGCCCCG

AGAACCACAG GTGTACACCC TGCCCCCATC CCGGGAAGAG ATGACCAAGA ACCAGGTCAG CCTGACCTGC

CTGGTCAAAG GCTTCTATCC CAGCGACATC GCCGTGGAGT GGGAGAGCAA TGGGCAGCCG GAGAACAACT

ACAAGACCAC GCCTCCCGTG CTGGACTCCG ACGGCTCCTT CTTCCTCTAC AGCAAGCTCA CCGTGGACAA

GAGCAGGTGG CAGCAGGGGA ACGTCTTCTC ATGCTCCGTG ATGCATGAGG CTCTGCACAA CCACTACACG

CAGAAGAGCC TCTCCCTGTC TCCGGGTAAA
```

Antibody 508.20.33b Heavy Chain Variable Region Nucleic Acid Sequence
(SEQ ID NO: 39)
GAA GTTCAGCTGG TGGAGTCTGG CGGTGGCCTG GTGCAGCCAG GGGGCTCACT CCGTTTGTCC

TGTGCAGCTT CTGGCTTCAC CTTCTCTAGT ACTGCTATTC ACTGGGTGCG TCAGGCCCCG GGTAAGGGCC

TGGAATGGGT TGCTAGGATT TCTCCTGCTA ACGTAATAC TAACTATGCC GATAGCGTCA AGGGCCGTTT

CACTATAAGC GCAGACACAT CCAAAAACAC AGCCTACCTA CAAATGAACA GCTTAAGAGC TGAGGACACT

GCCGTCTATT ATTGTGCTCG TTGGATCGGG TCCCGGGAGC TGTACATTAT GGACTACTGG GGTCAAGGAA

CCCTGGTCAC CGTCTCCTCG

Antibody 508.20.33b Full Length Light Chain Nucleic Acid Sequence
(SEQ ID NO: 40)
GA TATCCAGATG ACCCAGTCCC CGAGCTCCCT GTCCGCCTCT GTGGGCGATA GGGTCACCAT

CACCTGCCGT GCCAGTCAGG ATGTGTCCAC TGCTGTAGCC TGGTATCAAC AGAAACCAGG AAAAGCTCCG

AAGCTTCTGA TTTACTCGGC ATCCTTCCTC TACTCTGGAG TCCCTTCTCG CTTCTCTGGT AGCGGTTCCG

GGACGGATTT CACTCTGACC ATCAGCAGTC TGCAGCCGGA AGACTTCGCA ACTTATTACT GTCAGCAAGC

CTATCCGGCC CTACACACGT TCGGACAGGG TACCAAGGTG GAGATCAAAC GAACTGTGGC TGCACCATCT

GTCTTCATCT TCCCGCCATC TGATGAGCAG TTGAAATCTG GAACTGCTTC TGTTGTGTGC CTGCTGAATA

ACTTCTATCC CAGAGAGGCC AAAGTACAGT GGAAGGTGGA TAACGCCCTC CAATCGGGTA ACTCCCAGGA

GAGTGTCACA GAGCAGGACA GCAAGGACAG CACCTACAGC CTCAGCAGCA CCCTGACGCT GAGCAAAGCA

GACTACGAGA AACACAAAGT CTACGCCTGC GAAGTCACCC ATCAGGGCCT GAGCTCGCCC GTCACAAAGA

GCTTCAACAG GGGAGAGTGT

Antibody 508.20.33b Light Chain Variable Region Nucleic Acid Sequence
(SEQ ID NO: 41)
GA TATCCAGATG ACCCAGTCCC CGAGCTCCCT GTCCGCCTCT GTGGGCGATA GGGTCACCAT

CACCTGCCGT GCCAGTCAGG ATGTGTCCAC TGCTGTAGCC TGGTATCAAC AGAAACCAGG AAAAGCTCCG

AAGCTTCTGA TTTACTCGGC ATCCTTCCTC TACTCTGGAG TCCCTTCTCG CTTCTCTGGT AGCGGTTCCG

GGACGGATTT CACTCTGACC ATCAGCAGTC TGCAGCCGGA AGACTTCGCA ACTTATTACT GTCAGCAAGC

CTATCCGGCC CTACACACGT TCGGACAGGG TACCAAGGTG GAGATCAAAC GA

In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-PCSK9 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-PC SK9 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

C. Assays

Anti-PCSK9 antibodies provided herein may be identified, screened for, or characterized for their physical/chemical properties and/or biological activities by various assays known in the art.

1. Binding Assays and Other Assays

In one aspect, an anti-PCSK9 antibody of the invention is tested for its PCSK9 binding activity, e.g., by known methods such as ELISA, Western blot, etc. Numerous types of competitive binding assays can be used to determine if an anti-PCSK9 antibody competes with another, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In certain embodiments, binding is inhibited by at least 80-85%, 85-90%, 90-95%, 95-97%, or 97% or more.

In one aspect of the invention, competition assays may be used to identify an antibody that competes with anti-PCSK9 antibody 508.20.04a, 508.20.04b, 508.20.06, 508.20.28a, 508.20.28b, 508.20.33a, 508.20.33b or 508.20.84 for binding to PCSK9. In certain embodiments, such a competing antibody binds to the same epitope (e.g., a linear or a conformational epitope) that is bound by anti-PCSK9 antibody 508.20.04a, 508.20.04b, 508.20.06, 508.20.28a, 508.20.28b, 508.20.33a, 508.20.33b and/or 508.20.84. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized PCSK9 is incubated in a solution comprising a first labeled antibody that binds to PCSK9 (e.g., anti-PCSK9 antibody 508.20.04a, 508.20.04b, 508.20.06, 508.20.28a, 508.20.28b, 508.20.33a, 508.20.33b or 508.20.84) and a second unlabeled antibody that is being tested for its ability to compete with the first antibody for binding to PCSK9. The second antibody may be present in a hybridoma supernatant. As a control, immobilized PCSK9 is incubated in a solution comprising the first labeled antibody but not the second unlabeled antibody. After incubation under conditions permissive for binding of the first antibody to PCSK9, excess unbound antibody is removed, and the amount of label associated with immobilized PCSK9 is measured. If the amount of label associated with immobilized PCSK9 is substantially reduced in the test sample relative to the control sample, then that indicates that the second antibody is competing with the first antibody for binding to PCSK9. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-PCSK9 antibodies thereof having biological activity. Biological activity of the anti-PCSK9 antibodies may include, e.g., blocking, antagonizing, suppressing, interfering, modulating and/or reducing one or more biological activities of PCSK9. Antibodies having such biological activity in vivo and/or in vitro are provided.

In certain embodiments, anti-PCSK9 antibody binds human PCSK9 and prevents interaction with the LDLR. In certain embodiments, anti-PCSK9 antibody binds specifically to human PCSK9 and/or substantially inhibits binding of human PCSK9 to LDLR by at least about 20%-40%, 40-60%, 60-80%, 80-85%, or more (for example, by measuring binding in an in vitro competitive binding assay). In certain embodiments, the invention provides isolated anti-PCSK9 antibodies which specifically bind to PCSK9 and which antagonize the PCSK9-mediated effect on LDLR levels when measured in vitro using the LDLR down regulation assay in HepG2 cells disclosed herein.

D. Immunoconjugates

The invention also provides immunoconjugates comprising an anti-PCSK9 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethyl-lauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{153}$Sm, $^{212}$Bi, $^{32}$P, $^{212}$Pb, and radioactive isotopes of Lu. When the radioconjugate is used for detection, it may comprise a radioactive atom for scintigraphic studies, for example $^{99m}$Tc or $^{123}$I, or a spin label for nuclear magnetic resonance (NMR) imaging (also known as magnetic resonance imaging, MRI, such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-PCSK9 antibodies provided herein is useful for detecting the presence of PCSK9 in a biological sample. The term "detecting" as used herein encompasses quantitative or qualitative detection. In certain embodiments, a biological sample is blood, serum or other liquid samples of biological origin. In certain embodiments, a biological sample comprises a cell or tissue.

In one embodiment, an anti-PCSK9 antibody for use in a method of diagnosis or detection is provided. In a further aspect, a method of detecting the presence of PCSK9 in a biological sample is provided. In certain embodiments, the method comprises detecting the presence of PCSK9 protein in a biological sample. In certain embodiments, PCSK9 is human PCSK9. In certain embodiments, the method comprises contacting the biological sample with an anti-PCSK9 antibody as described herein under conditions permissive for binding of the anti-PCSK9 antibody to PCSK9, and detecting whether a complex is formed between the anti-PCSK9 antibody and PCSK9. Such method may be an in vitro or in vivo method. In one embodiment, an anti-PCSK9 antibody is used to select subjects eligible for therapy with an anti-PCSK9 antibody, e.g. where PCSK9 or LDL-cholesterol is a biomarker for selection of patients.

Exemplary disorders that may be diagnosed using an antibody of the invention include cholesterol related disorders (which includes "serum cholesterol related disorders"), including any one or more of the following: hypercholesterolemia, heart disease, metabolic syndrome, diabetes, coronary heart disease, stroke, cardiovascular diseases, Alzheimers disease and generally dyslipidemias, which can be manifested, for example, by an elevated total serum cholesterol, elevated LDL, elevated triglycerides, elevated very low density lipoprotein (VLDL), and/or low HDL. In one aspect, the invention provides a method for treating or preventing hypercholesterolemia, and/or at least one symptom of dyslipidemia, atherosclerosis, cardiovascular disease (CVD) or coronary heart disease, in an individual comprising administering to the individual an effective amount of anti-PCSK9 antibody. In certain embodiments, the invention provides an effective amount of an anti-PCSK9 antibody for use in treating or preventing hypercholesterolemia, and/or at least one symptom of dyslipidemia, atherosclerosis, CVD or coronary heart disease, in a subject. The invention further provides the use of an effective amount of an anti-PCSK9 antibody that antagonizes extracellular or circulating PCSK9 in the manufacture of a medicament for treating or preventing hypercholesterolemia, and/or at least one symptom of dyslipidemia, atherosclerosis, CVD or coronary heart disease, in an individual.

In certain embodiments, labeled anti-PCSK9 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

This invention also encompasses compositions, including pharmaceutical formulations, comprising an anti-PCSK9 antibody, and polynucleotides comprising sequences encoding an anti-PCSK9 antibody. In certain embodiments, compositions comprise one or more antibodies that bind to PCSK9, or one or more polynucleotides comprising sequences encoding one or more antibodies that bind to PCSK9. These compositions may further comprise suitable carriers, such as pharmaceutically acceptable excipients including buffers, which are well known in the art.

Pharmaceutical formulations of an anti-PCSK9 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide statin. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

In one aspect, the invention provides a composition comprising an anti-PCSK9 antibody at about 100 to about 225 mg/mL, arginine succinate at about 180 to about 220 mM, polysorbate at about 0.01% to about 0.03%, and pH at about 5.2 to about 5.8. In certain embodiments, the composition is suitable for subcutaneous administration. In certain embodiments, the viscosity of the composition is less than about 25 cP at 25° C., less than about 20 cP at 25° C., less than about 15 cP at 25° C., less than about 12 cP at 25° C., or less than about 10 cP at 25° C. In certain embodiments, the composition is stable for at least one month, at least two months, at least three months, at least four months, at least five months, or at least six months at 2-8° C. In some embodiments, the composition is in a 0.5-mL, 1-mL, 1.25-mL, 1.5-mL, 1.75-mL, 2-mL, 2.25-mL, or 2.5-mL pre-filled syringe. In certain embodiments, the antibody in the composition is about any of 110, 120, 125, 130, 135, 140, 145, 150, 155, 160, 165, 170, 175, 180, 185, 190, 195, 200, 205, 210, 215, 220, and 225 mg/mL, including concentrations between any of these concentrations. In certain embodiments, arginine succinate in the composition is about any of 180, 185, 190, 200, 210 and 220 mM, including concentrations between any of these concentrations. In certain embodiments, polysorbate (e.g., polysorbate 20, polysorbate 80) in the composition is about any of 0.01%, 0.015%, 0.02%, 0.025%, and 0.03%, including concentrations between any of these concentrations. In certain embodiments, the composition has a pH at any of 5.0, 5.2, 5.4, 5.5, 5.6, 5.8, 5.9, 6.0, 6.1 and 6.2, including pH between any of these values. In certain embodiments, the anti-PCSK9 antibody in the composition is at about 150 mg/mL, arginine succinate in the composition is at about 200 mM, and polysorbate 20 in the composition is about 0.02%, and pH at about 5.5.

In one aspect, the invention provides a composition comprising an anti-PCSK9 antibody at about 150 to about 225 mg/mL, histidine acetate at about 10 to about 30 mM, arginine acetate at about 150 to about 170 mM, polysorbate at about 0.01% to about 0.03%, and pH at about 5.8 to about 6.2. In certain embodiments, the composition is suitable for subcutaneous administration. In certain embodiments, the viscosity of the composition is less than about 25 cP at 25° C., less than about 20 cP at 25° C., less than about 15 cP at 25° C., less than about 12 cP at 25° C., or less than about 10 cP at 25° C. In certain embodiments, the composition is stable for at least one month, at least two months, at least three months, at least four months, at least five months, or at least six months at 2-8° C. In some embodiments, the composition is in a 0.5-mL, 1-mL, 1.25-mL, 1.5-mL, 1.75-mL, 2-mL, 2.25-mL, or 2.5-mL pre-filled syringe. In certain embodiments, the antibody in the composition is about any of 150, 155, 160, 165, 170, 175, 180, 185, 190, 195, 200, 205, 210, 215, 220, and 225 mg/mL, including concentrations between any of these concentrations. In certain embodiments, histidine acetate in the composition is about any of 10, 15, 20, 25, and 30 mM, including concentrations between these concentrations. In certain embodiments, arginine acetate in the composition is about any of 150, 155, 160, 165, and 170 mM, including concentrations between any of these concentrations. In certain embodiments, polysorbate (e.g., polysorbate 20, polysorbate 80) in the composition is about any of 0.01%, 0.015%, 0.02%, 0.025%, and 0.03%, including concentrations between any of these concentrations. In certain embodiments, the composition has a pH at any of 5.8, 5.9, 6.0, 6.1 and 6.2, including pH between any of these values. In certain embodiments, the anti-PCSK9 antibody in the composition is at about 200 mg/mL, histidine acetate in the composition is at about 20 mM, arginine acetate in the composition is at about 160 mM, and polysorbate 20 in the composition is about 0.02%, and pH at about 6.0.

Also provided herein is a subcutaneous administration device containing the anti-PCSK9 antibody in a composition described herein, for delivering to an individual a flat dose in the range of 200 mg to 1200 mg of the antibody. A complete dose for one administration may be in one or more of the devices. In certain embodiments, the concentration of the antibody in the device is about 200 mg/mL. In certain embodiments, the device is a pre-filled syringe (e.g., 0.5-mL syringe, 1-mL syringe, 1.25-mL syringe, 1.5-mL syringe, 1.75-mL syringe, 2-mL syringe, 2.25-mL syringe, or 2.5-mL syringe) or a high volume, single use, subcutaneous infusion device (e.g., for delivery of from 1-10 mL, 2-8 mL, 3-6 mL, 4-5 mL, or 4, 5, 6, 7, 8, 9, or 10 mL).

G. Therapeutic Methods and Compositions

Any of the anti-PCSK9 antibodies provided herein may be used in therapeutic methods.

In one aspect, an anti-PCSK9 antibody for use as a medicament is provided. In another aspect, an anti-PCSK9 antibody for use in treating conditions associated with cholesterol related disorder is provided. In certain embodiments, an anti-PCSK9 antibody for use in treating conditions associated with elevated level of LDL-cholesterol is provided. In certain embodiments, an anti-PCSK9 antibody for use in a method of treatment is provided. In certain embodiments, the invention provides an anti-PCSK9 antibody for use in a method of treating an individual having conditions associated with elevated level of LDL-cholesterol comprising administering to the individual an effective amount of the anti-PCSK9 antibody. In certain embodiments, the methods and uses described herein further comprise administering to the individual an effective amount of at least one additional therapeutic agent, e.g., statin. In certain embodiments, the invention provides an anti-PCSK9 antibody for use in reducing LDL-cholesterol level in a subject. In further embodiments, the invention provides an anti-PCSK9 antibody for use in lowering serum LDL-cholesterol level in a subject. In certain embodiments, the invention provides an anti-PCSK9 antibody for use in increasing availability of LDLR in a subject. In certain embodiments, the invention provides an anti-PCSK9 antibody for use in inhibiting binding of PCSK9 to LDLR in a subject. In certain embodiments, the invention provides an anti-PCSK9 antibody for use in a method of reducing LDL-cholesterol level in an individual comprising administering to the individual an effective of the anti-PCSK9 antibody to reduce the LDL-cholesterol level. In certain embodiments, the invention provides an anti-PCSK9 antibody for use in a method of lowering serum LDL-cholesterol level in an individual comprising administering to the individual an effective of the anti-PCSK9 antibody to lower the serum LDL-cholesterol level. In certain embodiments, the invention provides an anti-PCSK9 antibody for use in a method of increasing availability of LDLR in an individual comprising administering to the individual an effective of the anti-PCSK9 antibody to increase availability of LDLR. In certain embodiments, the invention provides an anti-PCSK9 antibody for use in a method of inhibiting binding of PCSK9 to LDLR in an individual comprising administering to the individual an effective of the anti-PCSK9 antibody to inhibit the binding of PCSK9 to LDLR.

An "individual" or "subject" according to any of the embodiments described herein is preferably a human.

In a further aspect, the invention provides for the use of an anti-PCSK9 antibody in the manufacture or preparation of a medicament. In one embodiment, the medicament is for treatment of cholesterol related disorder. In certain embodiments, the cholesterol related disorder is hypercholesterolemia. In another embodiment, the medicament is for use in a method of treating hypercholesterolemia comprising administering to an individual having hypercholesterolemia an effective amount of the medicament.

In certain embodiments, the disorder treated is any disease or condition which is improved, ameliorated, inhibited or prevented by removal, inhibition or reduction of PCSK9 activity. In certain embodiments, diseases or disorders that are generally addressable (either treatable or preventable) through the use of statins can also be treated. In certain embodiments, disorders or disease that can benefit from the prevention of cholesterol synthesis or increased LDLR expression can also be treated by anti-PCSK9 antibodies of the present invention. In certain embodiments, individuals treatable by the anti-PCSK9 antibodies and therapeutic methods of the invention include individuals indicated for LDL apheresis, individuals with PCSK9-activating mutations (gain of function mutations, "GOF"), individuals with heterozygous Familial Hypercholesterolemia (heFH), individuals with primary hypercholesterolemia who are statin intolerant or statin uncontrolled, and individuals at risk for developing hypercholesterolemia who may be preventably treated. Other indications include dyslipidemia associated with secondary causes such as Type 2 diabetes mellitus, cholestatic liver diseases (primary biliary cirrhosis), nephrotic syndrome, hypothyroidism, obesity, and the prevention and treatment of atherosclerosis and cardiovascular diseases. In certain embodiments, the individuals treatable by the anti-PCSK9 antibodies and therapeutic methods described herein include individuals with LDL-c levels of 90-250 mg/dL and with coronary heart disease (CHD) or a CHD risk equivalent as described in detail in Example 12.

In certain embodiments, the methods described herein comprise administering an anti-PCSK9 antibody to an individual suffering from coronary heart disease. In certain embodiments, an individual with coronary heart disease has a history of documented myocardial infarction. In certain embodiments, an individual with coronary heart disease refers to an individual who has had a prior coronary revascularization procedure (e.g., percutaneous coronary intervention or coronary artery bypass graft). In certain embodiments, an individual with coronary heart disease refers to an individual having at least one coronary atherosclerotic lesion with 50% diameter stenosis (e.g., as determined by coronary angiography including invasive coronary angiography or cardiac computed tomography coronary angiography).

In certain embodiments, the methods described herein comprise administering an anti-PCSK9 antibody to an individual having at least one CHD risk equivalent. In certain embodiments, an individual with a CHD risk equivalent is an individual having one or more forms of clinical atherosclerotic disease, such as, for example, peripheral arterial disease (e.g., ankle/brachial blood pressure index of <0.85, prior percutaneous or surgical peripheral arterial revascularization procedure, prior non-traumatic amputation of a lower extremity due to peripheral artery disease, or ≥50% diameter stenosis on prior vascular imaging), carotid artery disease (e.g., carotid atherosclerotic lesion with ≥50% diameter stenosis or prior cutaneous or surgical carotid revascularization procedure), prior ischemic stroke, or abdominal aortic aneurysm. In certain embodiments, an individual with a CHD risk equivalent is an individual having type II diabetes. In certain embodiments, an individual with a CHD risk equivalent is an individual having type I diabetes coupled with organ damage (e.g., retinopathy, neuropathy, or nephropathy including microalbuminuria). In certain embodiments, an individual with a CHD risk equivalent is an individual having moderate to severe chronic kidney disease.

In certain embodiments, the methods described herein comprise administering an anti-PCSK9 antibody to an individual having one or more of the following risk factors: age (≥45 years for men or ≥55 years for women), smoking (within 1 month), hypertension (systolic blood pressure≥140 mmHg, diastolic blood pressure≥90 mmHg, or taking an antihypertensive medication), low HDL cholesterol (<40 mg/dL), or a family history of premature CHD.

In certain embodiments, the methods and uses described herein further comprises administering to the individual an effective amount of at least one additional therapeutic agent, e.g., statin. In certain embodiments, the additional therapeutic agent is for preventing and/or treating atherosclerosis and/or cardiovascular diseases. In certain embodiment, the additional therapeutic agent is for use in a method of reducing the risk of recurrent cardiovascular events. In certain embodiments, the additional therapeutic agent is for elevating the level of HDL-cholesterol in a subject.

In a further aspect, the invention provides pharmaceutical formulations comprising any of the anti-PCSK9 antibodies provided herein, e.g., for use in any of the above therapeutic methods. In one embodiment, a pharmaceutical formulation comprises any of the anti-PC SK9 antibodies provided herein and a pharmaceutically acceptable carrier. In another embodiment, a pharmaceutical formulation comprises any of the anti-PC SK9 antibodies provided herein and at least one additional therapeutic agent, e.g., statin.

Antibodies of the invention can be used either alone or in combination with other agents in a therapy. For instance, an antibody of the invention may be co-administered with at least one additional therapeutic agent. In certain embodiments, such additional therapeutic agent elevates the level of LDLR. In certain embodiments, an additional therapeutic agent is a LDL-cholesterol lowering drugs such as statin, e.g., atorvastatin, fluvastatin, lovastatin, mevastatin, pitavastatin, pravastatin, rosuvastatin, simvastatin, or any combination thereof, e.g., VYTORIN®, ADVICOR® or SIMCOR®. In certain embodiments, an additional therapeutic agent is a HDL-cholesterol raising drugs.

Such combination therapies noted above encompass combined administration (where two or more therapeutic agents are included in the same or separate formulations), and separate administration, in which case, administration of the anti-PCSK9 antibody of the invention can occur prior to, simultaneously, and/or following, administration of the additional therapeutic agent and/or adjuvant.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Anti-PC SK9 antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered.

In certain embodiments, a flat-fixed dosing regimen is used to administer anti-PCSK9 antibody to an individual. Depending on the type and severity of the disease an exemplary flat-fixed dosage might range from 10 to 1200 mg of anti-PCSK9 antibody. One exemplary dosage of the antibody would be in the range from about 10 mg to about 1000 mg. Another exemplary dosage of the antibody would be in the range from about 100 mg to about 600 mg. Another exemplary dosage of the antibody would be in the range from about 200 mg to about 800 mg. Another exemplary dosage of the antibody would be in the range from about 350 mg to about 400 mg. Another exemplary dosage of the antibody would be in the range from about 750 mg to about 800 mg. In certain embodiments, 150 mg, 200 mg, 220 mg, 300 mg, 380 mg, 400 mg, 500 mg, 600 mg, 700 mg, 760 mg, 800 mg, 1000 mg, 1140 mg, or 1200 mg of anti-PCSK9 antibody is administered to an individual. In certain embodiments, the flat dose of the anti-PCSK9 antibody is administered every 2 weeks, every 4 weeks, every 6 weeks, every 8 weeks, every 10 weeks, or every 12 weeks. In certain embodiments, the flat dose of the anti-PCSK9 antibody is administered no more frequently than once every 2 weeks, every 4 weeks, every 6 weeks, every 8 weeks, every 10 weeks, or every 12 weeks. In certain embodiments, the flat dose of the anti-PCSK9 antibody is administered every month, every 1.5 months, every 2 months, every 2.5 months, or every 3 months. In certain embodiments, the flat dose of the anti-PCSK9 antibody is administered no more frequently than once every month, every 1.5 months, every 2 months, every 2.5 months, or every 3 months. In certain embodiments, the anti-PCSK9 antibody is administered subcutaneously. However, other dosage regimens may be useful. The progress of this therapy is easily monitored by conventional techniques and assays.

In certain embodiments, the flat, fixed, subcutaneous dose to be administered is provided in a volume that is less than or equal to 5 mL, 4.5 mL, 4 mL, 3.8 mL, 3.5 mL, 3 mL, 2.5 mL, 2 mL, 1.9 mL, 1.5 mL, or 1 mL. In certain embodiments, the flat, fixed, subcutaneous dose is 800 mg in a total volume of less than or equal to 4 mL. In certain embodiments, the flat, fixed, subcutaneous dose is 760 mg in a total volume of less than or equal to 3.8 mL. In certain embodiments, the flat, fixed, subcutaneous dose is 600 mg in a total volume of less than or equal to 3 mL. In certain embodiments, the flat, fixed, subcutaneous dose is 400 mg in a total volume of less than or equal to 2 mL. In certain embodiments, the flat, fixed, subcutaneous dose is 380 mg in a total volume of less than or equal to 1.9 mL.

In certain embodiments, the LDL-cholesterol level in the individual treated by the methods described herein is reduced by at least about 45%, at least about 50%, at least about 55%, or at least about 60% from baseline. In some embodiments, the LDL-cholesterol level in the individual treated by the methods described is reduced at least about 45%, at least about 50%, at least about 55%, or at least about 60% from baseline, and maintains at the reduced level for at least two weeks, at least one month, at least two months, or three months after last dosing. In some embodiments, the LDL-cholesterol level in the individual treated by the methods described is reduced at least about 45%, at least about 50%, at least about 55%, or at least about 60% from baseline within about 1 week, about 10 days, or about 2 weeks of the initial dose. In some embodiments, the LDL-cholesterol level in the individual treated by the methods described is reduced at least about 45%, at least about 50%, at least about 55%, or at least about 60% from baseline within about 1 week, about 10 days, or about 2 weeks of the initial dose, and maintains at the reduced level for at least two weeks, at least one month, at least two months, or three months after last dosing. In certain embodiments, the LDL-cholesterol level in the individual treated by the methods described is reduced at least about 45% and maintains at the reduced level for at least about six weeks, at least about 7 weeks or at least about 1.5 months. In certain embodiments, the LDL-cholesterol level in the individual treated by the methods described is reduced at least about 45% within about 1 week from the initial dose and maintains at the reduced level for at least about six weeks, at least about 7 weeks or at least about 1.5 months. In certain embodiments, the LDL-cholesterol level in the individual treated by the methods described is reduced at least about 50% and maintains at the reduced level for at least about four weeks or at least about 1 month. In certain embodiments, the LDL-cholesterol level in the individual treated by the methods described is reduced at least about 50% within about 10 days from the initial dose and maintains at the reduced level for at least about four weeks or at least about 1 month. In certain embodiments, the LDL-cholesterol level in the individual treated by the methods described is reduced at least about 50% and maintains at the reduced level for at least about eight weeks or at least about 2 months. In certain embodiments, the LDL-cholesterol level in the individual treated by the methods described is reduced at least about 50% within about 10 days from the initial dose and maintains at the reduced level for at least about eight weeks or at least about 2 months. In certain embodiments, the LDL-cholesterol level in the individual treated by the methods described is reduced at least about 55% and maintains at the reduced level for at least about two weeks. In certain embodiments, the LDL-cholesterol level in the individual treated by the methods described is reduced at least about 55% within about 2 weeks of the initial dose and maintains at the reduced level for at least about two weeks. As used herein, a "baseline" level (such as baseline level for LDL-cholesterol level) in an individual refers to the level before an administration of an anti-PC SK9 antibody described herein to the individual. In certain embodiments, the baseline may be a mean or average of two or more measurements obtained before administration of an anti-PC SK9 antibody.

In certain embodiments, the LDL-cholesterol level in the individual treated by the methods described herein is reduced by at least about 60 mg/dL, at least about 70 mg/dL, at least about 75 mg/dL, at least about 80 mg/dL, or at least about 90 mg/dL from baseline. In some embodiments, the LDL-cholesterol level in the individual treated by the methods described is reduced by at least about 60 mg/dL, at least about 70 mg/dL, at least about 75 mg/dL, at least about 80 mg/dL, or at least about 90 mg/dL from baseline, and maintains at the reduced level for at least two weeks, at least one month, at least two months, or three months after last dosing. In some embodiments, the LDL-cholesterol level in the individual treated by the methods described is reduced by at least about 60 mg/dL, at least about 70 mg/dL, at least about 75 mg/dL, at least about 80 mg/dL, or at least about 90 mg/dL from baseline within about 1 week, about 10 days, or about 2 weeks of the initial dose. In some embodiments, the LDL-cholesterol level in the individual treated by the methods described is reduced by at least about 60 mg/dL, at least about 70 mg/dL, at least about 75 mg/dL, at least about 80 mg/dL, or at least about 90 mg/dL from baseline within about 1 week, about 10 days, or about 2 weeks of the initial dose, and maintains at the reduced level for at least two weeks, at least one month, at least two months, or three months after last dosing. In certain embodiments, the LDL-cholesterol level in the individual treated by the methods described is reduced by at least about 60 mg/dL or 70 mg/dL and maintains at the reduced level for at least about six weeks, at least about 7 weeks or at least about 1.5 months. In certain embodiments, the LDL-cholesterol level in the individual treated by the methods described is reduced by at least about 60 mg/dL or 70 mg/dL within about 1 week from the initial dose and maintains at the reduced level for at least about six weeks, at least about 7 weeks or at least about 1.5 months. In certain embodiments, the LDL-cholesterol level in the individual treated by the methods described is reduced by at least about 80 mg/dL and maintains at the reduced level for at least about four weeks or at least about 1 month. In certain embodiments, the LDL-cholesterol level in the individual treated by the methods described is reduced by at least about 80 mg/dL within about 10 days from the initial dose and maintains at the reduced level for at least about four weeks or at least about 1 month. In certain embodiments, the LDL-cholesterol level in the individual treated by the methods described is reduced by at least about 90 mg/dL and maintains at the reduced level for at least about two weeks. In certain embodiments, the LDL-cholesterol level in the individual treated by the methods described is reduced by at least about 90 mg/dL within about 2 weeks of the initial dose and maintains at the reduced level for at least about two weeks.

In certain embodiments, the reduction in LDL-cholesterol levels is maintained within a certain range between dosings. In certain embodiments, upon administration of a dose of an anti-PCSK9 antibody, LDL-cholesterol levels are reduced to a nadir of at least about 45%, at least about 50%, at least about 55%, or at least about 60% from baseline and do not increase beyond about 40%, 45%, 50%, 55%, or 60% below baseline before the next dosing of the anti-PCSK9 antibody. In certain embodiments, upon administration of a dose of an anti-PCSK9 antibody, LDL-cholesterol levels are reduced to a nadir of at least about 45% from baseline and do not increase beyond about 40% or 45% below baseline before the next dosing of the anti-PCSK9 antibody. In certain embodiments, upon administration of a dose of an anti-PCSK9 antibody, LDL-cholesterol levels are reduced to a nadir of at least about 50% from baseline and do not increase beyond about 40%, 45%, or 50% below baseline before the next dosing of the anti-PCSK9 antibody. In certain embodiments, upon administration of a dose of an anti-PCSK9 antibody, LDL-cholesterol levels are reduced to a nadir of at least about 55% from baseline and do not increase beyond about 40%, 45%, 50%, or 55% below baseline before the next dosing of the anti-PCSK9 antibody. In certain embodiments, upon administration of a dose of an anti-PCSK9 antibody, LDL-cholesterol levels are reduced to a nadir of at least about 60% from baseline and do not increase beyond about 40%, 45%, 50%, 55%, or 60% below baseline before the next dosing of the anti-PCSK9 antibody.

In certain embodiments, the reduction in LDL-cholesterol levels is maintained within a certain range between dosings. In certain embodiments, upon administration of a dose of an anti-PCSK9 antibody, LDL-cholesterol levels are reduced to a nadir of at least about 60 mg/dL, at least about 70 mg/dL, at least about 75 mg/dL, at least about 80 mg/dL, or at least about 90 mg/dL below baseline and do not increase beyond about 55 mg/dL, 60 mg/dL, 65 mg/dL, 70 mg/dL, 75 mg/dL, 80 mg/dL or 90 mg/dL below baseline before the next dosing of the anti-PCSK9 antibody. In certain embodiments, upon administration of a dose of an anti-PCSK9 antibody, LDL-cholesterol levels are reduced to a nadir of at least about 60 mg/dL below baseline and do not increase beyond about 55 mg/dL or 60 mg/dL below baseline before the next dosing of the anti-PCSK9 antibody. In certain embodiments, upon administration of a dose of an anti-PCSK9 antibody, LDL-cholesterol levels are reduced to a nadir of at least about 70 mg/dL below baseline and do not increase beyond about 55 mg/dL, 60 mg/dL, 65 mg/dL, or 70 mg/dL below baseline before the next dosing of the anti-PCSK9 antibody. In certain embodiments, upon administration of a dose of an anti-PCSK9 antibody, LDL-cholesterol levels are reduced to a nadir of at least about 75 mg/dL below baseline and do not increase beyond about 55 mg/dL, 60 mg/dL, 65 mg/dL, 70 mg/dL, or 75 mg/dL below baseline before the next dosing of the anti-PCSK9 antibody. In certain embodiments, upon administration of a dose of an anti-PCSK9 antibody, LDL-cholesterol levels are reduced to a nadir of at least about 80 mg/dL below baseline and do not increase beyond about 55 mg/dL, 60 mg/dL, 65 mg/dL, 70 mg/dL, 75 mg/dL, or 80 mg/dL below baseline before the next dosing of the anti-PCSK9 antibody. In certain embodiments, upon administration of a dose of an anti-PCSK9 antibody, LDL-cholesterol levels are reduced to a nadir of at least about 90 mg/dL below baseline and do not increase beyond about 55 mg/dL, 60 mg/dL, 65 mg/dL, 70 mg/dL, 75 mg/dL, 80 mg/dL or 90 mg/dL below baseline before the next dosing of the anti-PCSK9 antibody.

In one embodiment, an anti-PCSK9 antibody is administered to a subject at a dose of 800 mg every 8 weeks, wherein the level of LDL-cholesterol in the subject is reduced by at least 50% below baseline within 10 days and does not increase to more than 40% or 45% below baseline before the next dose. In one embodiment, an anti-PCSK9 antibody is administered to a subject at a dose of 760 mg every 8 weeks, wherein the level of LDL-cholesterol in the subject is reduced by at least 45% below baseline within 14 days and does not increase to more than 35% or 40% below baseline before the next dose. In one embodiment, an anti-PCSK9 antibody is administered to a subject at a dose of 400 mg every 4 weeks, wherein the level of LDL-cholesterol in the subject is reduced by at least 50% below baseline within 10 days and does not increase to more than 45% or 50% below baseline before the next dose. In one embodiment, an anti-PCSK9 antibody is administered to a subject at a dose of 380 mg every 4 weeks, wherein the level of LDL-cholesterol in the subject is reduced by at least 50% below baseline within 10 days and does not increase to more than 45% or 50% below baseline before the next dose.

In certain embodiments, subjects receiving the anti-PCSK9 antibody are monitored for LDL-c levels and if their levels drop below 25 or 15 mg/dL, then their dose is adjusted down to around 50% or 25% of the initial dose, by reducing the total amount of antibody administered to around 50% or 25% of the initial dose administered and keeping the frequency of injections the same, by keeping the total amount of antibody administered the same but decrease the frequency by 2-fold or 4-fold (e.g., from once every 4 weeks to once every 8 weeks or 16 weeks), or a combination thereof (e.g., by reducing the dose and changing the frequency of administration). In certain embodiments, an anti-PCSK9 antibody is administered to a subject at an initial dose of 800 mg every 8 weeks. The subject is monitored and if the LDL-c levels of the subject drop below 25 or 15 mg/dL, then the subject is switched to a dose of 400 mg every 8 weeks, 400 mg every 16 weeks, 380 mg every 8 weeks, 380 mg every 16 weeks, 200 mg every 8 weeks, 200 mg every 4 weeks, 190 mg every 8 weeks, 190 mg every 4 weeks, 760 mg every 16 weeks or 4 months, or 760 mgs every 24 weeks or 6 month 800 mg every 16 weeks or 4 months, or 800 mgs every 24 weeks or 6 months. In one embodiment, an anti-PCSK9 antibody is administered to a subject at an initial dose of 800 mg every 8 weeks, the subject is monitored and if the subject's LDL-c levels drop below 25 mg/dL, the subject is switched to a dose of 200 mg every 8 weeks. In one embodiment, an anti-PCSK9 antibody is administered to a subject at an initial dose of 800 mg every 8 weeks, the subject is monitored and if the subject's LDL-c levels drop below 15 mg/dL, the subject is switched to a dose of 200 mg every 8 weeks. In certain embodiments, an anti-PCSK9 antibody is administered to a subject at an initial dose of 760 mg every 8 weeks. The subject is monitored and if the LDL-c levels of the subject drop below 25 or 15 mg/dL, then the subject is switched to a dose of 380 mg every 8 weeks, 380 mg every 16 weeks, 200 mg every 4 weeks, 200 mg every 8 weeks, 190 mg every 8 weeks, 190 mg every 4 weeks, 760 mg every 16 weeks or 4 months, or 760 mgs every 24 weeks or 6 months. In one embodiment, an anti-PCSK9 antibody is administered to a subject at an initial dose of 760 mg every 8 weeks, the subject is monitored and if the subject's LDL-c levels drop below 25 mg/dL, the subject is switched to a dose of 190 mg or 200 mg every 8 weeks. In one embodiment, an anti-PCSK9 antibody is administered to a subject at an initial dose of 760 mg every 8 weeks, the subject is monitored and if the subject's LDL-c levels drop below 15 mg/dL, the subject is switched to a dose of 190 mg or 200 mg every 8 weeks. In certain embodiments, an anti-PCSK9 antibody is administered to a subject at an initial dose of 400 mg every 4 weeks. The subject is monitored and if the LDL-c levels of the subject drop below 25 or 15 mg/dL, then the subject is switched to a dose of 200 mg every 4 weeks, 200 mg every 8 weeks, 100 mg every 4 weeks, 400 mg every 8 weeks, 400 mgs every 16 weeks or 3 months, 50 mgs every 2 weeks, or 25 mgs every 2 weeks. In one embodiment, an anti-PCSK9 antibody is administered to a subject at an initial dose of 400 mg every 4 weeks, the subject is monitored and if the subject's LDL-c levels drop below 25 mg/dL, the subject is switched to a dose of 100 mg every 4 weeks. In one embodiment, an anti-PCSK9 antibody is administered to a subject at an initial dose of 400 mg every 4 weeks, the subject is monitored and if the subject's LDL-c levels drop below 15 mg/dL, the subject is switched to a dose of 100 mg every 4 weeks. In one embodiment, an anti-PCSK9 antibody is administered to a subject at an initial dose of 400 mg every 4 weeks, the subject is monitored and if the subject's LDL-c levels drop below 25 mg/dL, the subject is switched to a dose of 200 mg every 8 weeks. In one embodiment, an anti-PCSK9 antibody is administered to a subject at an initial dose of 400 mg every 4 weeks, the subject is monitored and if the subject's LDL-c levels drop below 15 mg/dL, the subject is switched to a dose of 200 mg every 8 weeks. In one embodiment, an anti-PCSK9 antibody is administered to a subject at an initial dose of 400 mg every 4 weeks, the subject is monitored and if the subject's LDL-c levels drop below 25 mg/dL, the subject is switched to a dose of 50 mg every 2 weeks. In one embodiment, an anti-PCSK9 antibody is administered to a subject at an initial dose of 400 mg every 4 weeks, the subject is monitored and if the subject's LDL-c levels drop below 15 mg/dL, the subject is switched to a dose of 50 mg every 2 weeks. In one embodiment, an anti-PCSK9 antibody is administered to a subject at an initial dose of 400 mg every 4 weeks, the subject is monitored and if the subject's LDL-c levels drop below 25 mg/dL, the subject is switched to a dose of 25 mg every 2 weeks. In one embodiment, an anti-PCSK9 antibody is administered to a subject at an initial dose of 400 mg every 4 weeks, the subject is monitored and if the subject's LDL-c levels drop below 15 mg/dL, the subject is switched to a dose of 25 mg every 2 weeks. In certain embodiments, an anti-PCSK9 antibody is administered to a subject at an initial dose of 380 mg every 4 weeks. The subject is monitored and if the LDL-c levels of the subject drop below 25 mg/dL or 15 mg/dL, then the subject is switched to a dose of 200 mg every 4 weeks, 200 mg every 8 weeks, 190 mg every 4 weeks, 100 mg every 4 weeks, 90 mg every 4 weeks, 380 mg every 8 weeks, 380 mgs every 16 weeks or 3 months, 50 mg every 2 weeks, or 25 mg every 2 weeks. In one embodiment, an anti-PCSK9 antibody is administered to a subject at an initial dose of 380 mg every 4 weeks, the subject is monitored and if the subject's LDL-c levels drop below 25 mg/dL, the subject is switched to a dose of 100 mg every 4 weeks. In one embodiment, an anti-PCSK9 antibody is administered to a subject at an initial dose of 380 mg every 4 weeks, the subject is monitored and if the subject's LDL-c levels drop below 15 mg/dL, the subject is switched to a dose of 100 mg every 4 weeks. In one embodiment, an anti-PCSK9 antibody is administered to a subject at an initial dose of 380 mg every 4 weeks, the subject is monitored and if the subject's LDL-c levels drop below 25 mg/dL, the subject is switched to a dose of 200 mg every 8 weeks. In one embodiment, an anti-PCSK9 antibody is administered to a subject at an initial dose of 380 mg every 4 weeks, the subject is monitored and if the subject's LDL-c levels drop below 15 mg/dL, the subject is switched to a dose of 200 mg every 8 weeks. In one embodiment, an anti-PCSK9 antibody is administered to a subject at an initial dose of 380 mg every 4 weeks, the subject is monitored and if the subject's LDL-c levels drop below 25 mg/dL, the subject is switched to a dose of 190 mg every 8 weeks. In one embodiment, an anti-PCSK9 antibody is administered to a subject at an initial dose of 380 mg every 4 weeks, the subject is monitored and if the subject's LDL-c levels drop below 15 mg/dL, the subject is switched to a dose of 190 mg every 8 weeks. In one embodiment, an anti-PCSK9 antibody is administered to a subject at an initial dose of 380 mg every 4 weeks, the subject is monitored and if the subject's LDL-c levels drop below 25 mg/dL, the subject is switched to a dose of 50 mg every 2 weeks. In one embodiment, an anti-PCSK9 antibody is administered to a subject at an initial dose of 380 mg every 4 weeks, the subject is monitored and if the subject's LDL-c levels drop below 15 mg/dL, the subject is switched to a dose of 50 mg every 4 weeks. In one embodiment, an anti-PCSK9 antibody is administered to a subject at an initial dose of 380 mg every 4 weeks, the subject is monitored and if the subject's LDL-c levels drop below 25 mg/dL, the subject is switched to a dose of 25 mg every 2 weeks. In one embodiment, an anti-PCSK9 antibody is administered to a subject at an initial dose of 380 mg every 4 weeks, the subject is monitored and if the subject's LDL-c levels drop below 15 mg/dL, the subject is switched to a dose of 25 mg every 2 weeks.

It is understood that any of the above formulations or therapeutic methods may be carried out using an immunoconjugate of the invention in place of or in addition to an anti-PCSK9 antibody.

H. Articles of Manufacture and Kits

In another aspect of the invention, an article of manufacture or kit containing materials useful for the treatment, prevention and/or diagnosis of the disorders described above is provided. In certain embodiments, the article of manufacture or kit comprises a container containing one or more of the anti-PCSK9 antibodies or the compositions described herein. In certain embodiments, the article of manufacture or kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an anti-PCSK9 antibody of the invention. The label or package insert indicates that the composition is used for treating the condition of choice. Moreover, the article of manufacture or kit may comprise (a) a first container with a composition contained therein, wherein the composition comprises an anti-PCSK9 antibody of the invention; and (b) a second container with a composition contained therein, wherein the composition comprises a further cytotoxic or otherwise therapeutic agent. In certain embodiments, the second container comprises a second therapeutic agent, wherein the second therapeutic agent is a cholesterol-lowering drug of the "statin" class. In certain embodiments, the statin is and/or comprises atorvastatin (e.g., LIPITOR® or Torvast), fluvastatin (e.g., LESCOL), lovastatin (e.g., MEVACOR®, ALTOCOR™, or ALTOPREV®), mevastatin (pitavastatin (e.g., LIVALO® or PITAVA®), pravastatin (e.g., PRAVACHOL®, SELEKTINE®, LIPOSTAT®), rosuvastatin (e.g., CRESTOR®), simvastatin (e.g., ZOCOR®, LIPEX®), or any combination thereof, e.g., VYTORIN®, ADVICOR® or SIMCOR®.

The article of manufacture or kit in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture or kit may include an immunoconjugate of the invention in place of or in addition to an anti-PCSK9 antibody.

III. EXAMPLES

The following are examples of methods and compositions of the invention. It is understood that various other embodiments may be practiced, given the general description provided above.

Example 1

Generation of Anti-PC SK9 Antibodies

Residue numbers are according to Kabat (Kabat et al., Sequences of proteins of immunological interest, 5th Ed., Public Health Service, National Institutes of Health, Bethesda, Md. (1991)).

Library Sorting and Screening to Identify Anti-PCSK9 Antibodies

Biotinylated human PCSK9 generated in-house was used as antigen for library sorting. The phage libraries were sorted five rounds against biotinylated PCSK9 in solution phase. For the first round of sorting, 20 μg/mL biotinylated PCSK9 was added to antibody phage libraries VH (see, e.g., Lee et al., *J Immunol. Meth.* 284:119-132, 2004) and VHNL (see Liang et al., JMB. 366: 815-829, 2007) pre-blocked with phage blocking buffer PBST (phosphate-buffered saline (PBS) and 1% (w/v) bovine serum albumin (BSA) and 0.05% (v/v) TWEEN®-20) and incubated overnight at room temperature. The following day 120 μl of PBST/BSA pre-absorbed DYNABEADS® MYONE™ Streptavidin T1 (Invitrogen, Carlsbad, Calif.) was added to each library and incubated for 1 hour at room temperature. The beads were then washed three times with PBT (PBS with 0.05% TWEEN®-20), and bound phage were eluted with 1 mL 50 mM HCl and 500 mM NaCl for 30 minutes and neutralized with 400 μL of 1 M Tris base (pH7.5). Recovered phages were amplified in *E. coli* XL1-BLUE® cells. During the subsequent selection rounds, incubation of antibody phage with the biotinylated PCSK9 was reduced to 2-3 hours, and the phage bound antigen was captured for 30 minutes on NEUTRAVIDIN® coated (Catalog #89890, 10 μg/ml, Fisher Scientific, Waltham, Mass.) or streptavidin-coated (Catalog #21125, 10 μg/ml, Fisher Scientific, Waltham, Mass.) NUNC® 96 well MAXISORP® immunoplates. The stringency of plate washing was gradually increased.

After 5 rounds of panning, significant enrichment was observed. 96 clones were picked each from VH and VH/VL library sorting to determine whether they specifically bound to human PCSK9. The variable regions of these clones were PCR sequenced to identify unique sequence clones. Unique phage antibodies that bind human PCSK9 at least 5× above background were chosen and reformatted to full length IgGs for evaluation in in vitro cell assay.

Clones of interest were reformatted into IgGs by cloning VL and VH regions of individual clones into the LPG3 and LPG4 vector respectively, transiently expressing in mammalian CHO cells, and purifying with a protein A column.

Construct Libraries for Affinity Improvement of Clones Derived from the VH Library Phagemid pW0703 (derived from phagemid pV0350-2b (Lee et al., *J. Mol. Biol.* 340, 1073-1093 (2004)), containing stop codon (TAA) in all CDR-L3 positions and displaying monovalent Fab on the surface of M13 bacteriophage served as the library template for grafting heavy chain variable domains (VH) of clones of interest from the VH library for affinity maturation. Both hard and soft randomization strategies were used for affinity maturation. For hard randomization, one light chain library with selected positions of the three light chain CDRs was randomized using amino acids designed to mimic natural human antibodies and the designed DNA degeneracy was as described in Lee et al. (*J. Mol. Biol.* 340, 1073-1093 (2004)). For soft randomization, residues at positions 91-96 of CDR-L3, 30-33, 35 of CDR-H1, 50, 52, 53-54, 56, and 58 of CDR-H2, 95-100, 100A, and 100C of CDR-H3, were targeted; and three different combinations of CDR loops, H1/L3, H2/L3, and H3/L3, were selected for randomization. To achieve the soft randomization conditions, which introduced the mutation rate of approximately 50% at the selected positions, the mutagenic DNA was synthesized with 70-10-10-10 mixtures of bases favoring the wild type nucleotides (Gallop et al., *Journal of Medicinal Chemistry* 37:1233-1251 (1994)).

Phage Sorting Strategy to Generate Affinity Improvement

For affinity improvement selection, phage libraries were subjected to five rounds of solution sorting with increasing stringency. For the first round of solution sorting, 3 O.D./ml in 1% BSA and 0.05% TWEEN®-20 of phage input were incubated with 100 nM biotinylated PCSK9 (the concentration is based on parental clone phage IC50 value) in 100 μl buffer containing 1% SUPERBLOCK® (Pierce Biotechnology) and 0.05% TWEEN®-20 for 2 hours at room temperature. The mixture was further diluted 10× with 1% SUPERBLOCK®, and 100 μl/well was applied to NEUTRAVIDIN® coated wells (10 μg/ml) for 30 minutes at room temperature with gentle shaking. The wells were washed with PBS-0.05%

TWEEN®-20 ten times. To determine background binding, control wells containing phage were captured on NEUTRA-VIDIN® coated plates. Bound phage was eluted with 150 μl/well 50 mM HCl, 500 mM KCl for 30 minutes, and subsequently neutralized by 50 μl/well of 1M Tris pH 8, titered, and propagated for the next round. Four more rounds of solution sorting were carried out together with increasing selection stringency. The first couple of rounds were for on-rate selection by decreasing biotinylated target protein concentration from 100 nM to 1 nM, and the last two rounds were for off-rate selection by adding excess amounts of non-biotinylated target protein (300 to 1000 fold more) to compete off weaker binders at room temperature.

High Throughput Affinity Screening ELISA (Single Spot Competition)

Colonies were picked from the fifth round of screening. Colonies were grown overnight at 37° C. in 150 μl/well of 2YT media with 50 μg/ml carbenicillin and $1 \times 10^{10}$/ml K07 in 96-well plate (Falcon). From the same plate, a colony of XL1-BLUE® infected parental phage was picked as control. 96-well NUNC® MAXISORP® plates were coated with 100 μl/well of NEUTRAVIDIN® (10 μg/ml) in PBS at 4° C. overnight. The plates were blocked with 150 μl of 1% BSA and 0.05% TWEEN®-20 in PBS for 1 hour.

35 μl of the phage supernatant was diluted with 35 μl of ELISA (enzyme linked immunosorbent assay) buffer (PBS with 0.5% BSA, 0.05% TWEEN®-20) with or without 15 nM PCSK9 and let incubate for 1 hour at room temperature in an F plate (NUNC®). 35 μl of 3 μg/ml biotinylated-PCSK9 was then added to each well and incubated for 15 minutes at room temperature. 95 μl of mixture was transferred side by side to the NEUTRAVIDIN® coated plates. The plate was gently shaken for 15 min to allow the capture of biotinylated-PCSK9 bound phage to the plate. The plate was washed ten times with PBS-0.05% TWEEN®-20. The binding was quantified by adding horseradish peroxidase (HRP)-conjugated anti-M13 antibody in ELISA buffer (1:2500) and incubated for 30 minutes at room temperature. The plates were washed with PBS-0.05% TWEEN®-20 ten times. Next, 100 μl/well of a 1:1 ratio of 3,3',5,5'tetramethylbenzidine (TMB) Peroxidase substrate and Peroxidase Solution B ($H_2O_2$) (Kirkegaard-Perry Laboratories (Gaithersburg, Md.)) was added to the well and incubated for 5 minutes at room temperature. The reaction was stopped by adding 100 μl 0.1 M Phosphoric Acid ($H_3PO_4$) to each well and allowed to incubate for 5 minutes at room temperature. The O.D. (optical density) of the yellow color in each well was determined using a standard ELISA plate reader at 450 nm. The O.D. reduction (%) was calculated by the following equation:

$$OD_{450nm} \text{ reduction}(\%) = [(OD_{450nm} \text{ of wells with competitor})/(OD^4_{450nm} \text{ of well with no competitor})] * 100$$

Figure 1:
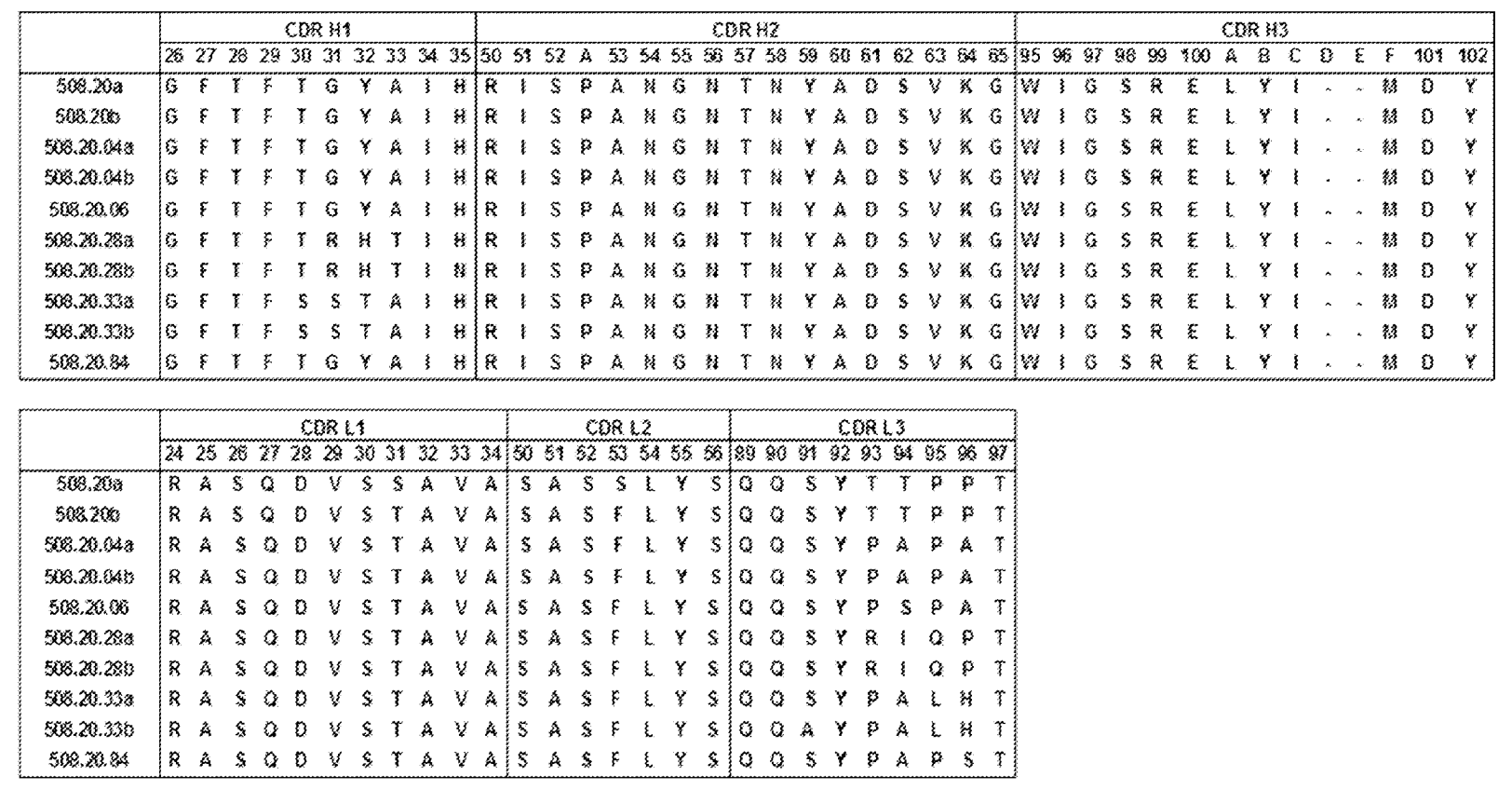
Figure 2A:
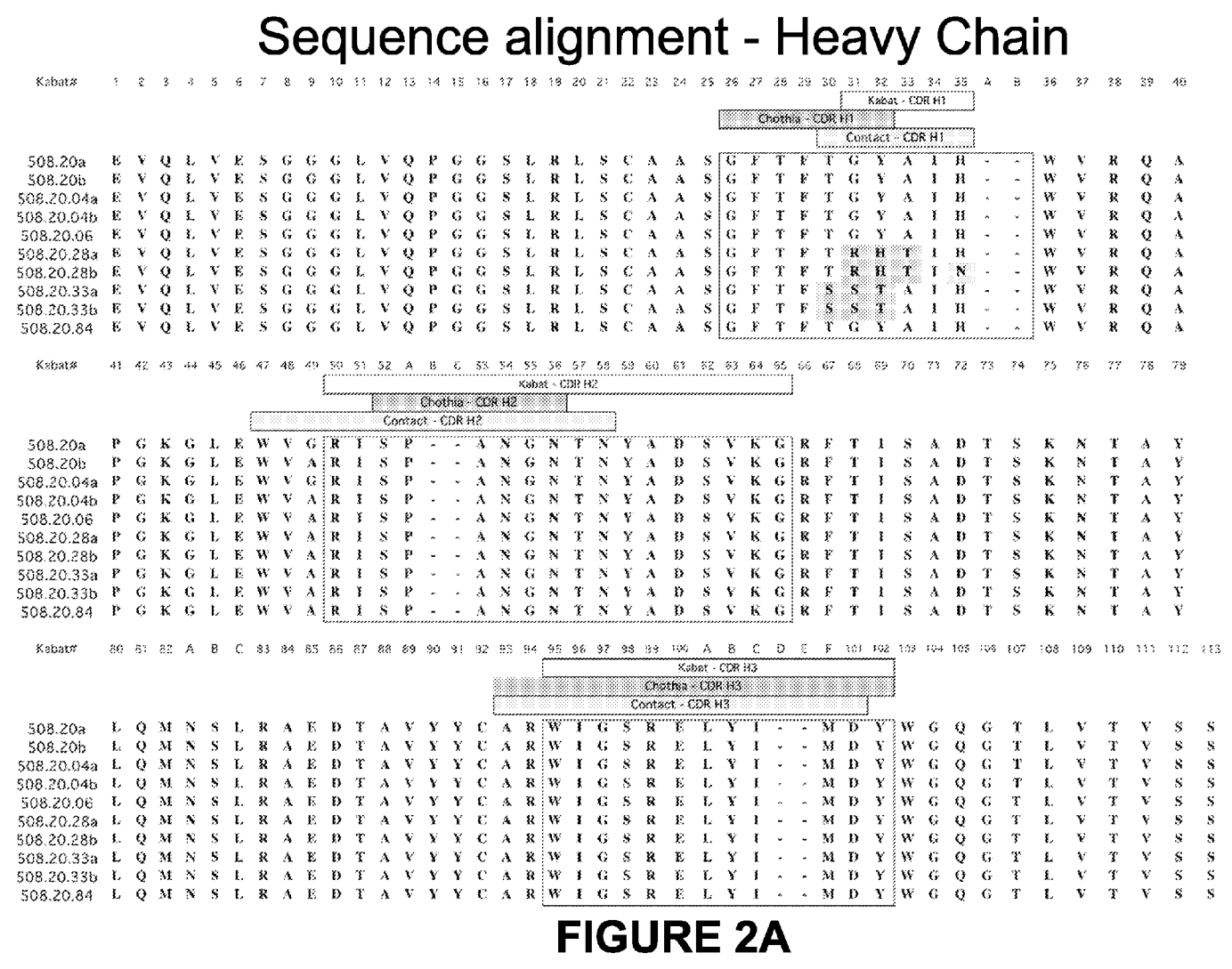
Figure 2B:
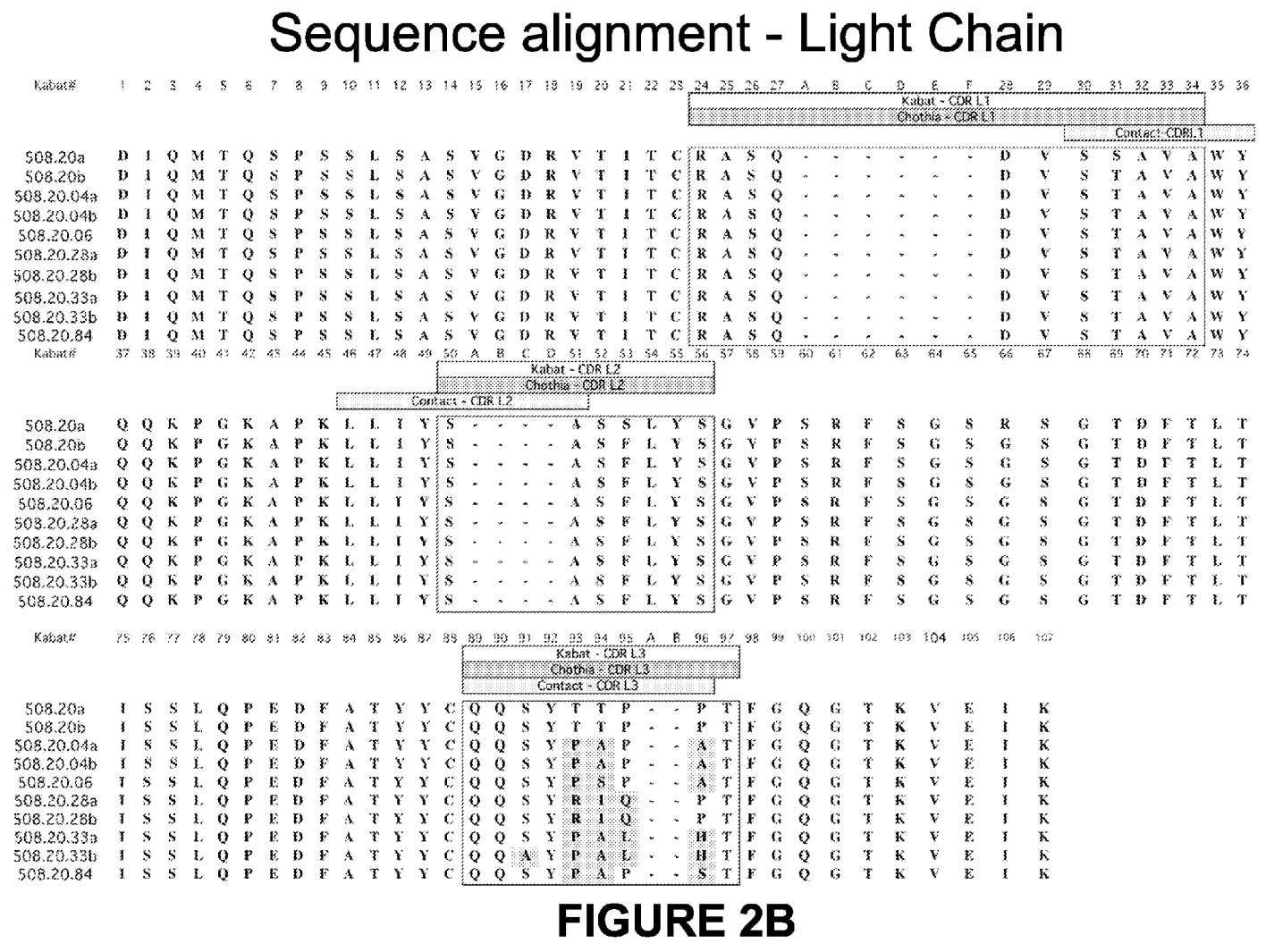

In comparison to the $OD_{450nm}$ reduction (%) of the well of parental phage (100%), clones that had the $OD_{450nm}$ reduction (%) lower than 50% were picked for sequence analysis. Unique clones were selected for phage preparation to determine binding affinity (phage $IC_{50}$) against PCSK9 by comparison to parental clone (clone 508.20b). Then the most affinity-improved clones (508.20.04b, 508.20.06, 508.20.28b, 508.20.33b and 508.20.84) were reformatted into human IgG₁ for antibody production and further BIAcore binding kinetic analysis and other in vitro or in vivo assay. See FIGS. 1 and 2.

Example 2

Characterization of Anti-PCSK9 Antibodies by BIAcore

Binding affinities of anti-PCSK9 antibodies were measured by Surface Plasmon Resonance (SRP) using a BIACORE® 3000 instrument. Anti-PCSK9 human antibodies were captured by mouse anti-human Fc antibody (Catalog# BR-1008-39, GE Healthcare, Piscataway, N.J.) coated on CM5 biosensor chips to achieve approximately 200 response units (RU). For kinetics measurements, two-fold serial dilutions (500 nM to 0.245 nM) of human, murine, rhesus, and cyno PCSK9 (Genentech, South San Francisco, Calif.) were injected in PBT buffer (PBS with 0.05% TWEEN®-20) at 25° C. with a flow rate of 30 μl/min. Association rates ($k_{on}$) and dissociation rates ($k_{off}$) were calculated using a simple one-to-one Langmuir binding model (BIACORE® Evaluation Software version 3.2). The equilibrium dissociation constant ($K_D$) was calculated as the ratio $k_{off}/k_{on}$. See FIG. 3.

Example 3

LDLR-PCSK9 Binding Assay

A competition binding ELISA was performed to investigate the activity of anti-PCSK9 antibodies in blocking human PCSK9 binding to LDLR. Briefly, 1 μg/mL of soluble human LDLR extracellular domain (R&D Systems, Minneapolis, Minn.) was coated on 384-well MAXISORP®-plate Nalgene Nunc International, Rochester, N.Y.) at 4° C. overnight. Then 0.25 μg/mL of biotinylated human PCSK9 pre-mixed with different concentrations of anti-PCSK9 antibodies and control antibodies were added to the plate and incubated for 2 hour at room temperature. The binding of PCSK9 to coated LDLR was detected by adding streptavidin-HRP (GE Healthcare) and substrate 3,3',5,5'-tetramethyl benzidine (TMBE-1000, Moss, Inc., Pasadena, Md.). The binding results (OD) were plotted against antibody concentration and $IC_{50}$ values were generated using KALEIDAGRAPH® software. See FIG. 4.

Example 4

Antibodies Prevent LDLR Downregulation on HepG2 Cells

Figure 5:
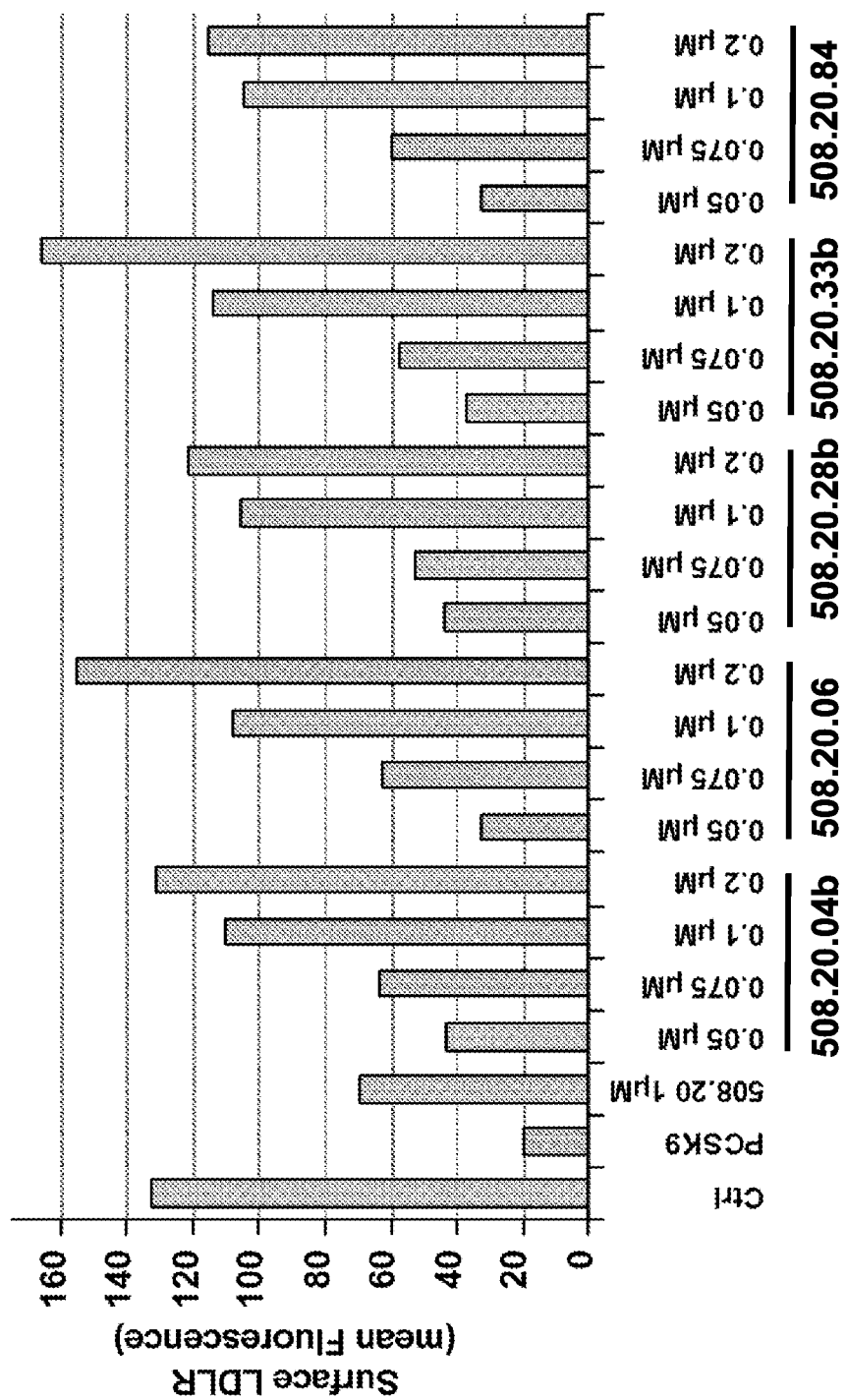
FIG. 5. Different concentrations of anti-PCSK9 antibodies were incubated with 15 μg/ml PCSK9 and added to HepG2 cells for 4 hours. Cells were processed for FACS analysis of surface LDLR. The data indicate that the anti-PCSK9 antibodies effectively prevented LDLR downregulation. The positive control is cells not treated with PCSK9.

HepG2 cells were seeded at $1 \times 10^5$ into a 48-well plate. The next day, the media was changed to 10% lipoprotein deficient serum (LPDS, Frederick, Md.). The following day, 15 μg/ml PCSK9 plus/minus anti-PCSK9 antibody were added to cells for 4 hours at 37° C. Cells were rinsed with PBS and detached using 2.5 mM EDTA. Cells were incubated with 1:20 anti-LDLR (Progen Biotechnik, Heidelberg, Germany) for 15 minutes, washed with PBS and incubated with 1:200 goat anti-mouse ALEXA FLUOR® 488 from Invitrogen (Carlsbad, Calif.) for 15 minutes. Cells were washed and resuspended in PBS plus 10 μg/ml propidium iodide. The samples were then analyzed with a dual laser flow cytometer (FACSCAN™, Becton Dickinson, Franklin Lakes, N.J.). The data suggest all five of the anti-PCSK9 antibodies (508.20.04b, 508.20.06, 508.20.28b, 508.20.33b and 508.20.84) prevent downregulation of LDLR. See FIG. 5.

Example 5

LDLR Downregulation in Mouse Liver

Figure 6:
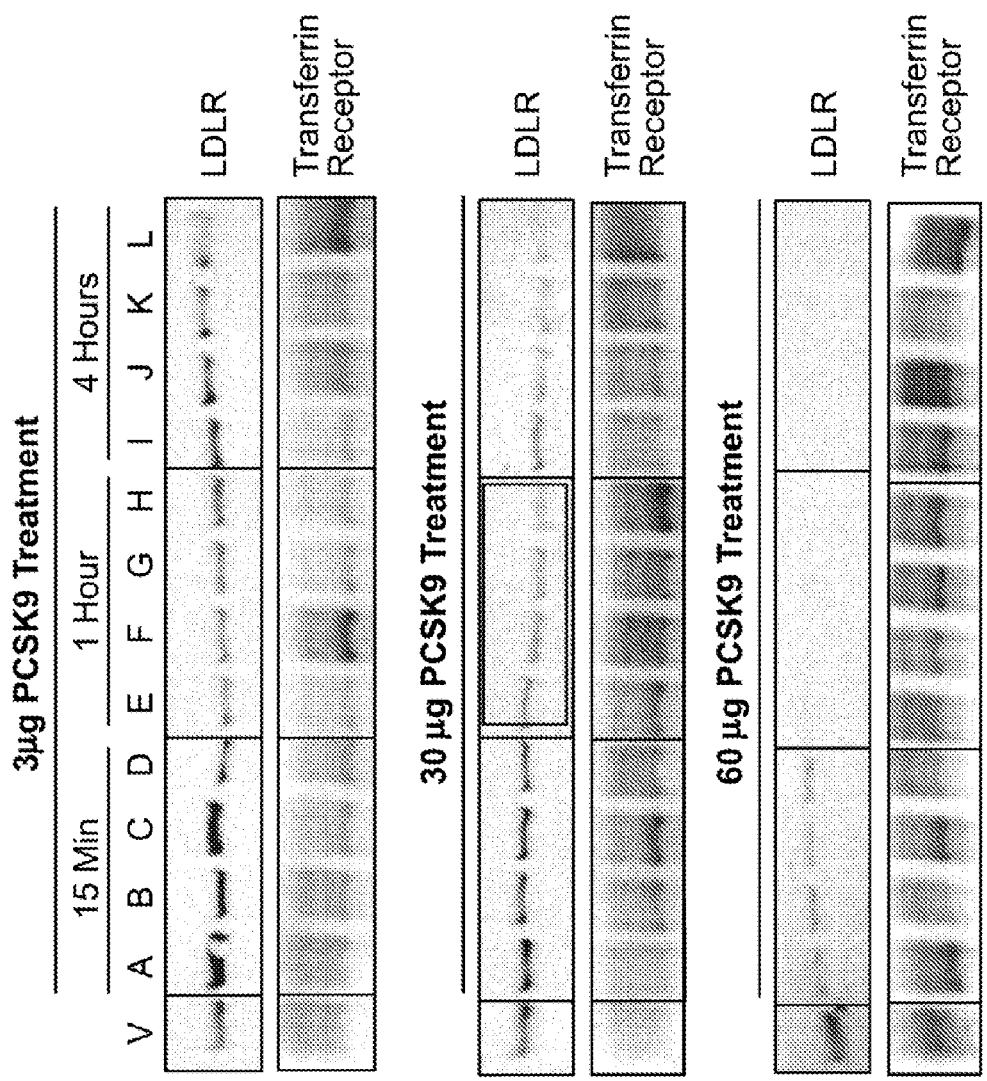
FIG. 6. Western blot with anti-LDLR antibody showing that 30 μg of PCSK9 for 1 hr significantly downregulated LDLR levels in mouse liver.

Normal C57/BL6 mice (Charles River, Wilmington, Mass.) were treated with 3, 30 or 601.4 of PCSK9 by I.V.

administration. Using the PROTEOEXTRACT® Native Membrane Protein Extraction Kit from Calbiochem (Gibbstown, N.J.) according to the manufacturer's instructions, liver from each mouse was harvested 15 min, 1 hr or 4 hrs after PCSK9 I.V. administration and proteins extracted. As a control, 5 mice were treated with vehicle only and 8 µg of each liver lysate were pooled for analysis. Lysates were analyzed by SDS-PAGE on 8% tris-gly gel (Invitrogen, Carlsbad, Calif.). Proteins were transferred to nitrocellulose membrane using IBLOT® (Invitrogen). The membrane was blocked with 5% nonfat milk for 1 hour and then incubated with 1:500 anti-LDLR (Abcam, Cambridge, Mass.) in 5% nonfat milk overnight at 4° C. The next day, the membrane was washed three times with TBS-T, incubated with 1:5000 anti-rabbit HRP (GE Healthcare, Piscataway, N.J.) for 1 hour and washed with TBS-T three times. Proteins were visualized using ECL-Plus (GE Healthcare) and exposed to X-OMAT®AR film (Kodak, Rochester, N.Y.). After an overnight exposure, the membrane was washed with TBS-T, incubated with 1:500 anti-transferrin receptor antibody (Invitrogen) for 1 hour, washed with TBS-T, incubated with 1:5000 anti-mouse HRP (GE Healthcare) for 1 hour, washed with TBS-T and visualized with ECL-Plus. Western blot with anti-LDLR antibody shows that 30 µg of PCSK9 for 1 hour significantly downregulated LDLR levels in mouse liver. See FIG. 6.

Example 6

Antibodies Prevent Liver LDLR Downregulation

Figure 7:
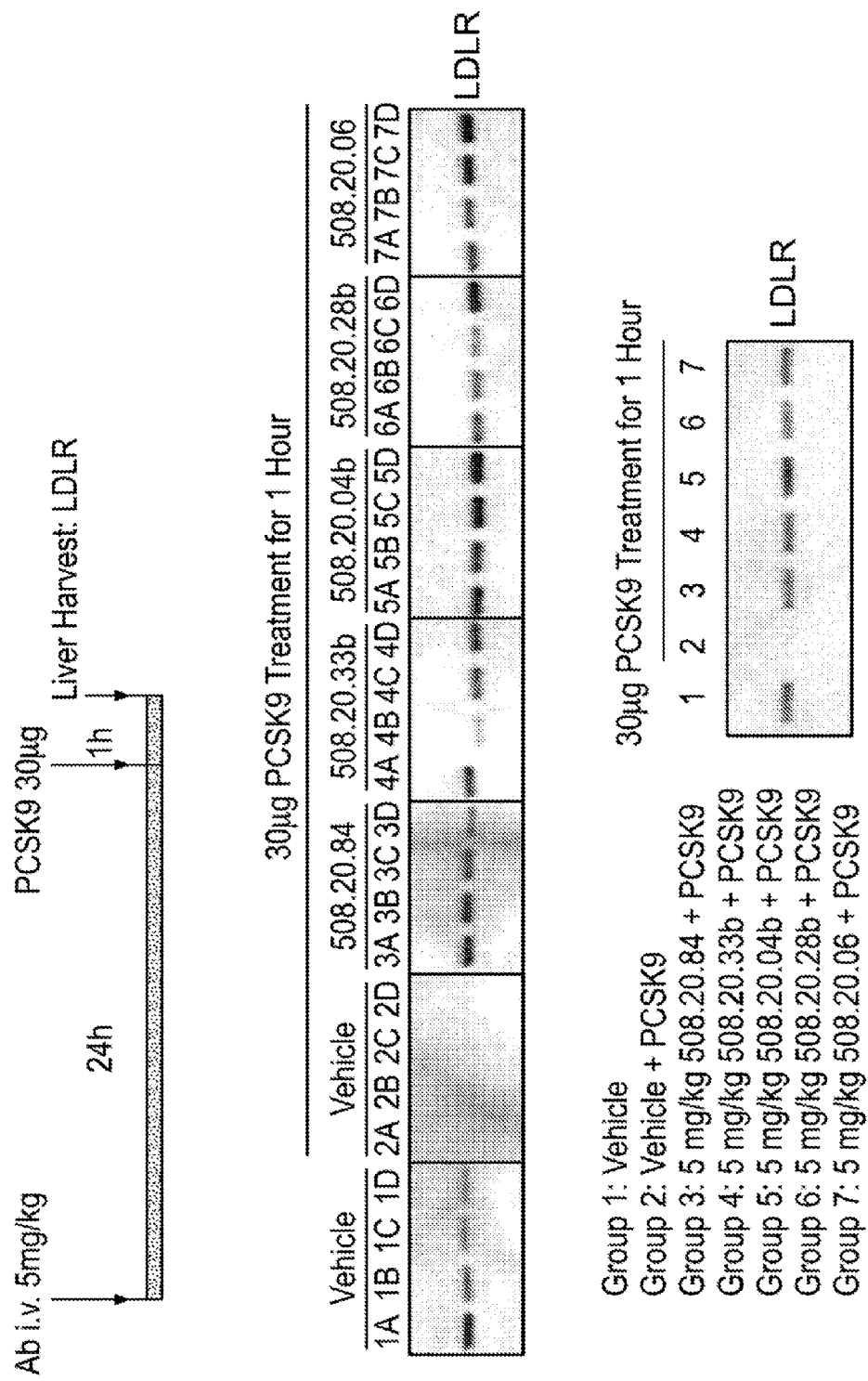
FIG. 7. Western blot with anti-LDLR antibody showing that all five anti-PCSK9 antibodies prevented LDLR downregulation in mouse liver. The bottom immunoblot is a pool of 4 livers (10 μg of protein from each liver) per treatment group.

Normal C57/BL6 (Charles River) mice were injected with vehicle or 5 mg/kg anti-PCSK9 antibodies 24 hours prior to treatment with 30 µg PCSK9 for 1 hour. Liver from each mouse was harvested using the PROTEOEXTRACT® Native Membrane Protein Extraction Kit (Calbiochem) according to the manufacturer's instructions. Lysates were analyzed by SDS-PAGE on 8% bis-tris gel. Proteins were transferred to nitrocellulose membrane using IBLOT® (Invitrogen). The membrane was blocked with 5% nonfat milk for 1 hour and then incubated with 1:500 anti-LDLR (Abcam) in 5% nonfat milk overnight at 4° C. The next day, the membrane was washed three times with TBS-T, incubated with 1:5000 anti-rabbit HRP (GE Healthcare) for 1 hour and washed three times with TBS-T. Proteins were visualized using ECL-Plus (GE Healthcare) and exposed to X-OMAT®AR film (KODAK®). Western blot with anti-LDLR antibody show that all five anti-PCSK9 antibodies (508.20.84, 508.20.33b, 508.20.04b, 508.20.28b, 508.20.06) prevented LDLR downregulation in mouse liver. See FIG. 7.

Example 7

Pharmacokinetics of Anti-PCSK9 Antibody

Figure 8:
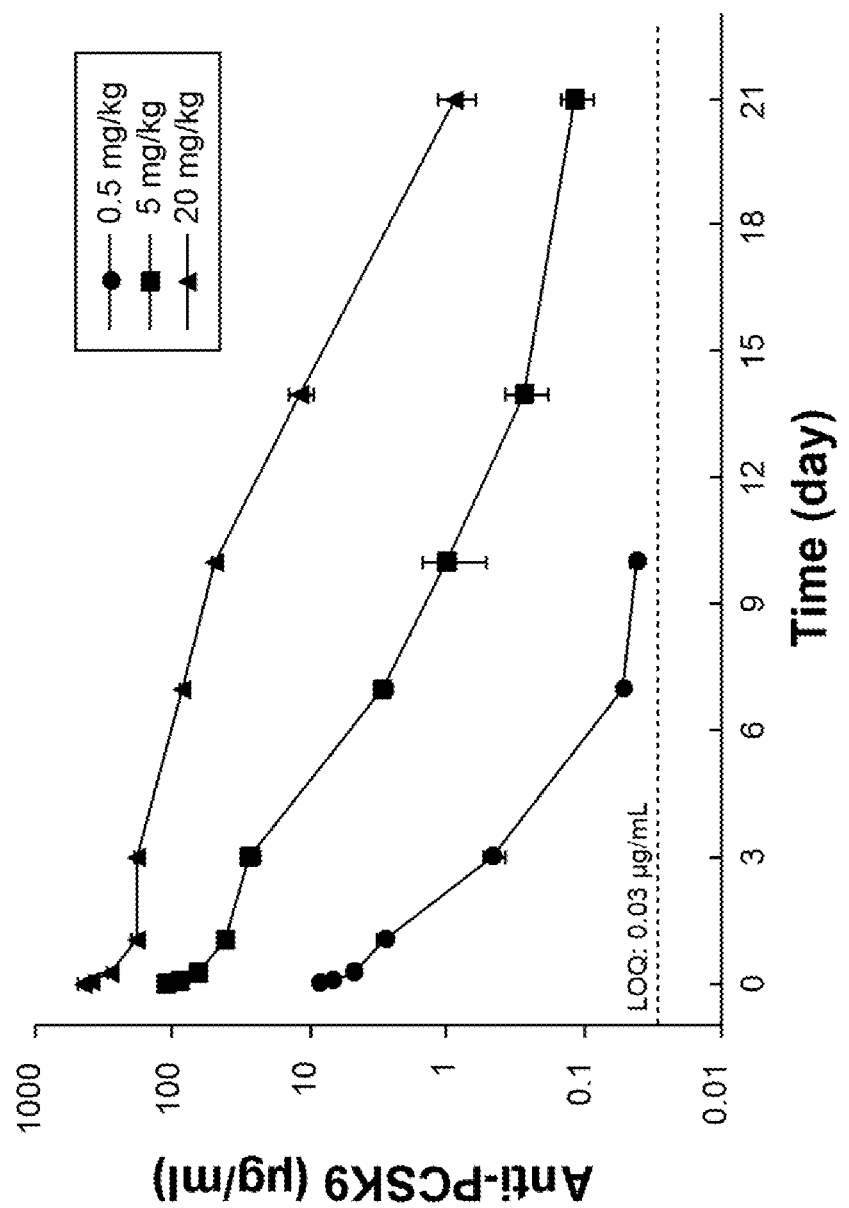
FIG. 8 shows anti-PCSK9 antibody concentrations in sera of C57JBL/6 mice after single I.V. injection. Shown are the average concentrations of the dosing groups 0.5 mg/kg; 5 mg/kg; and 20 mg/kg (n=3).
Figure 9:
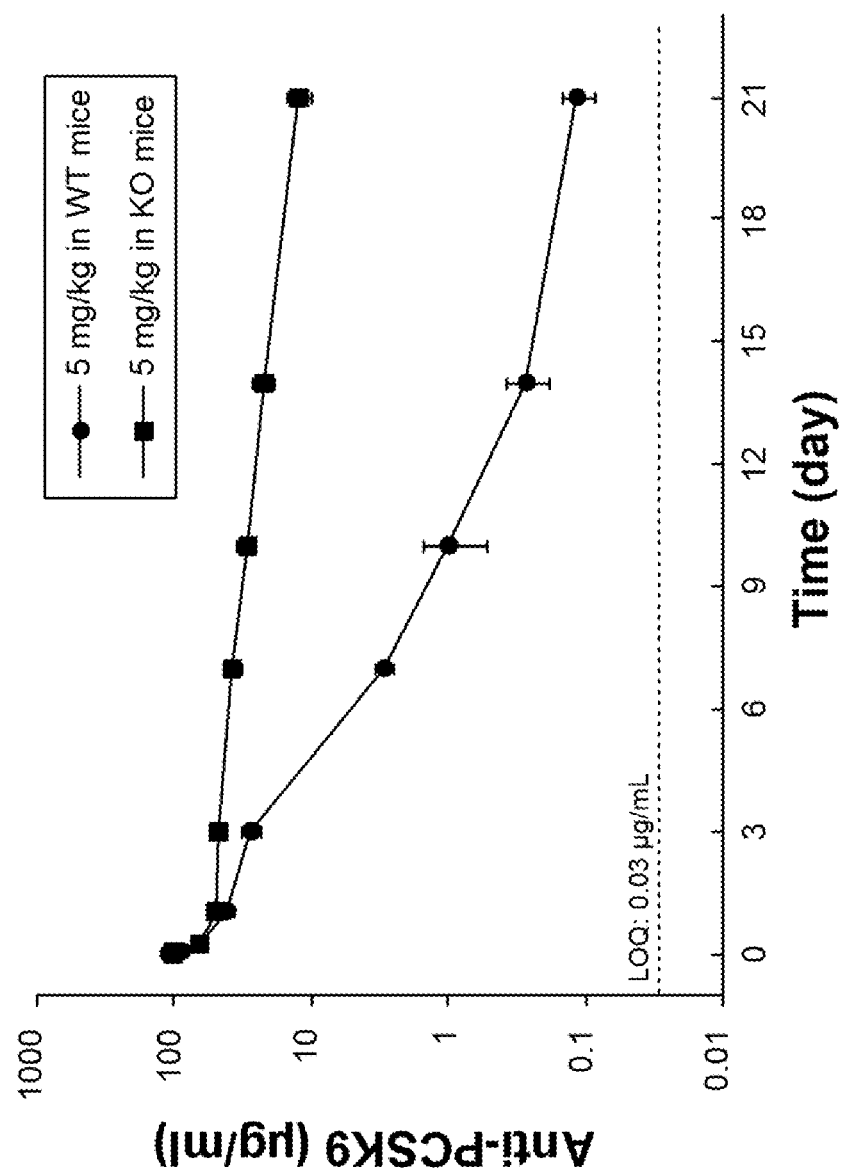
FIG. 9 shows comparison of anti-PCSK9 antibody concentrations in sera of C57JBL/6 WT and PCSK9$^{-/-}$ mice after single I.V. injection of 5 mg/kg anti-PCSK9 antibody. The average concentrations of each dosing group are shown (n=3).

Anti-PCSK9 antibody concentrations in mouse PK study samples were determined using anti-human IgG Fc ELISA. Briefly, donkey anti-human IgG Fc (Jackson ImmunoResearch, West Grove, Pa.) was used to coat assay plates and goat anti-human IgG Fc HRP conjugate (Jackson ImmunoResearch, West Grove, Pa.) was used as detection antibody. The assay was able to measure anti-PCSK9 antibody in up to 10% mouse serum matrix with assay range of 0.31-20 ng/mL. See FIGS. 8 and 9.

Figure 10:
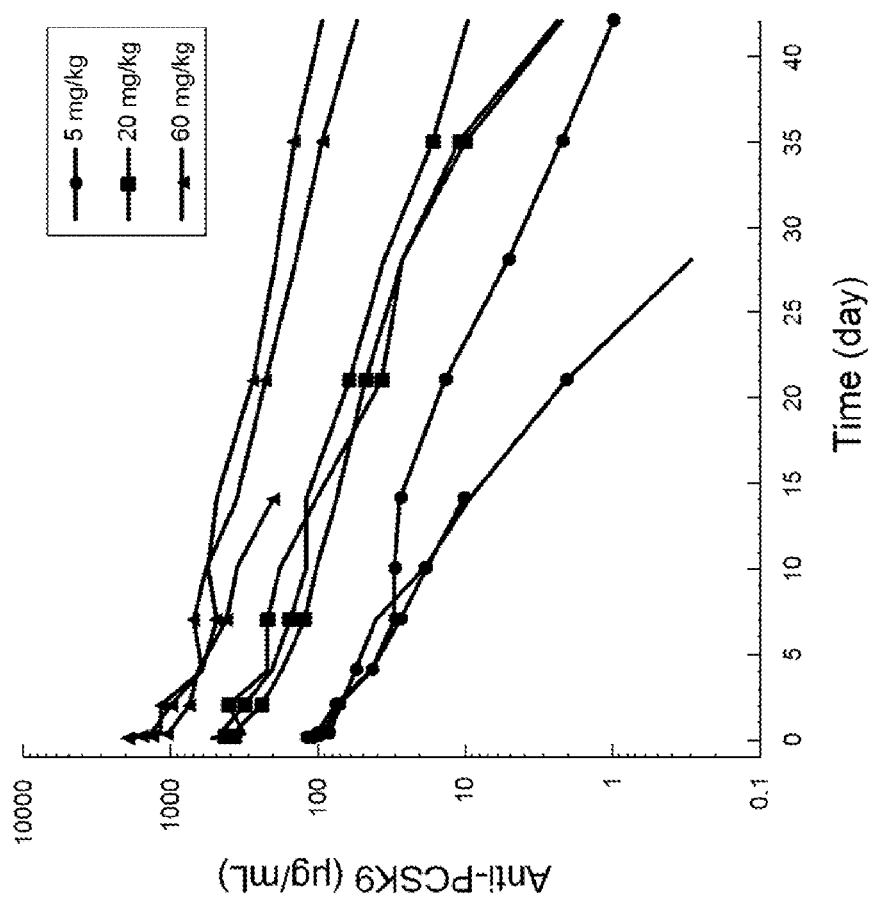
FIG. 10 shows anti-PCSK9 antibody concentrations in sera of individual cynomolgus monkey after single I.V. injection. Three dosing groups are included: 5 mg/kg; 20 mg/kg; and 60 mg/kg.
Figure 11:
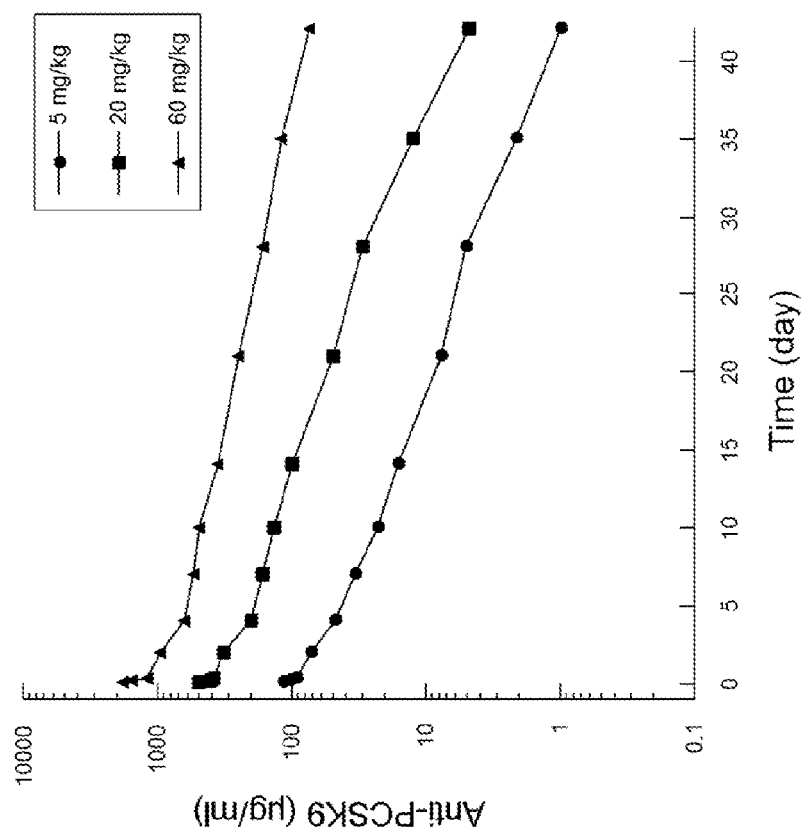
FIG. 11 shows anti-PCSK9 antibody concentrations in sera of cynomolgus monkeys after single I.V. injection. Shown are the average concentrations of the dosing groups 5 mg/kg, 20 mg/kg, and 60 mg/kg (n=3).

Serum anti-PCSK9 antibody concentrations in cynomolgus monkey PK study samples were determined by anti-PCSK9 antibody ELISA using recombinant human PCSK9 (Genentech, Inc. South San Francisco, Calif.) as capture and goat anti-human IgG (H+L) HRP as detection antibody. The assay was able to measure anti-PCSK9 antibody in up to 2% cynomolgus monkey serum matrix with assay range of 0.313-50 ng/mL. See FIGS. 10 and 11.

Example 8

Antibodies Reduce Serum Cholesterol Level in Mice

Eight weeks old male C57BL/6J mice were purchased commercially from Jackson Laboratory. The mice were on housing for one week at the holding room before the start of the experiment. All mice were pre-bled under anesthesia and total cholesterol levels from the mice were determined using INFINITY™ Cholesterol Reagent (Fisher Diagnostics, Middletown, Va.). The mice were randomized into 6 different groups with the same level of average cholesterol level. All mice received a single dose of 10 mg/kg body weight of either control antibody or anti-PCSK9 antibodies. The mice were bled on day 3, day 7, day 10 and day 15 and serum total cholesterol levels were determined using INFINITY™ Cholesterol Reagent (Fisher Diagnostics, Middletown, Va.).

Figure 12:
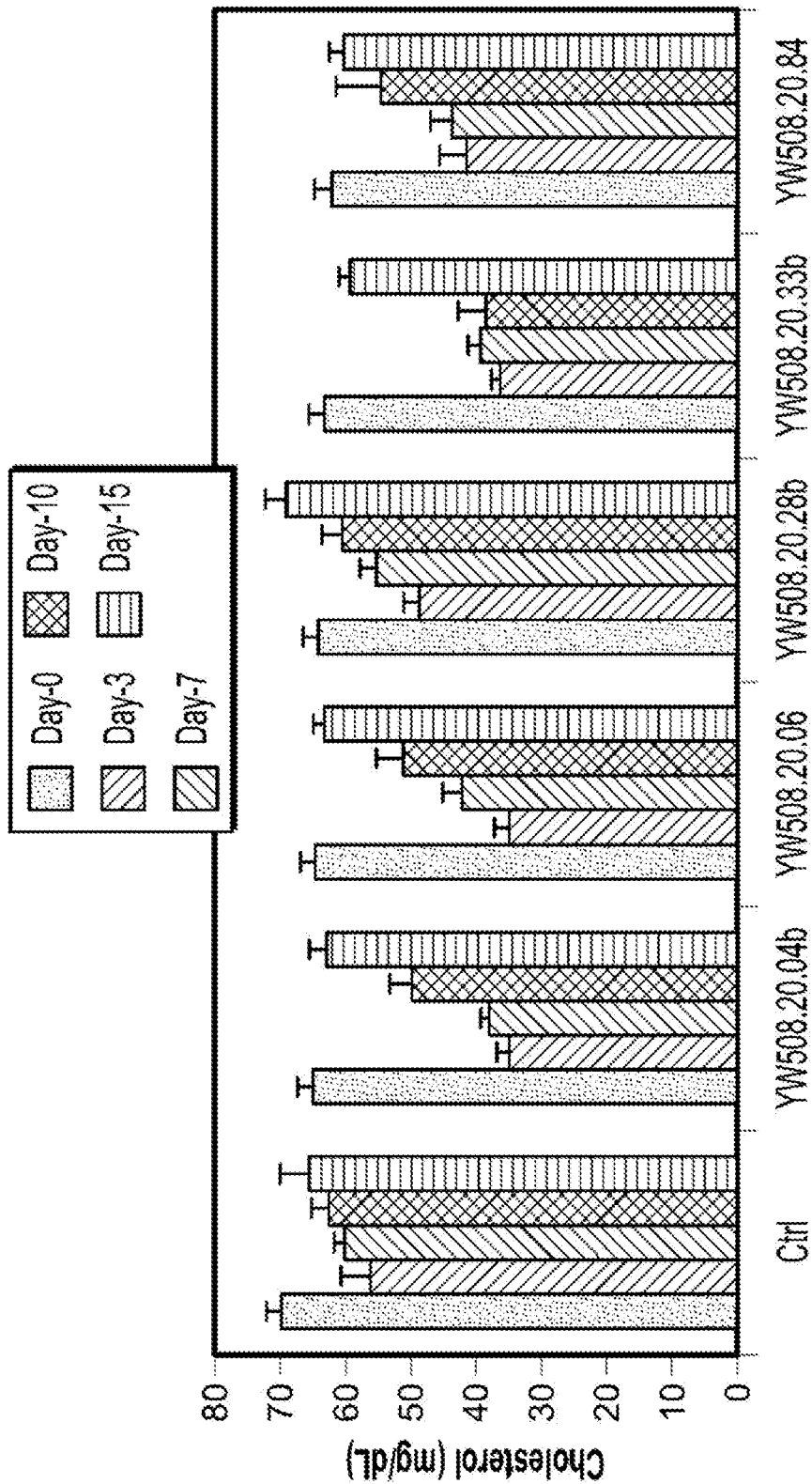
FIG. 12 shows total cholesterol level in the sera of mice treated with a single dose (10 mg/kg body weight) of either control (Crtl) or anti-PCSK9 antibody. Cholesterol levels were measured at different days as indicated in the figure.

All five anti-PCSK9 antibodies (508.20.04b, 508.20.06, 508.20.28b, 508.20.33b, 508.20.84) showed a reduction in total cholesterol levels when a single dose of 10 mg/kg was administered. The administration of anti-PCSK9 antibody resulted in a significant reduction in total cholesterol level on day 3 and up to day 10 when compared to the mice receiving control antibody. See FIG. 12.

Example 9

Enhancement of Statin Effectiveness

Figure 13:
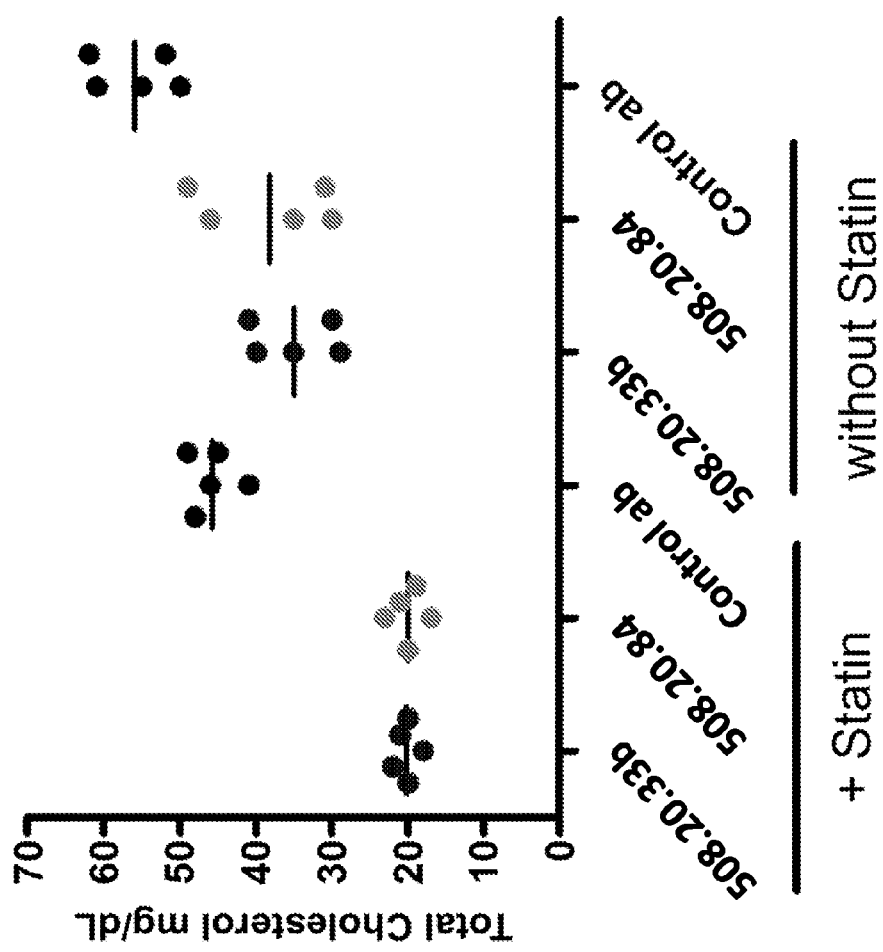
FIG. 13 shows total cholesterol level in the sera from the mice treated with single dose (10 mg/kg body weight) of either control or anti-PCSK9 antibody.

This experiment demonstrates that a combination of anti-PCSK9 antibody and statin results in a greater reduction in total cholesterol level compared to anti-PCSK9 antibody alone or statin alone treatments. See e.g., FIG. 13. Eight weeks old male C57BL/6J mice was purchased from Jackson Laboratory. The mice were grouped into 2 different groups. The non-statin mice received control diet, while statin groups received 0.2% of lovastatin in the diet for 2 weeks prior to antibody administration (Bioserve, Frenchtown, N.J.). All the mice were pre-bled and mice were randomized based on equal average cholesterol level. Mice were bled on day 3 and the total cholesterol levels were assayed using INFINITY™ Cholesterol Reagent (Fisher Diagnostics, Middletown, Va.).

The anti-PCSK9 antibodies showed significant cholesterol lowering effect. Statin alone treatment resulted in modest reduction in total cholesterol level, compared to non-statin groups. The combination of statin plus anti-PCSK9 antibody resulted in an additional reduction compared to anti-PCSK9 alone in total cholesterol level. See FIG. 13.

Example 10

X-Ray Crystal Structure of PCSK9 Bound to Fab Fragment of Anti-PCSK9 Antibody

Protein Purification and Crystallization 210 g of frozen cell paste from 10 L *E. coli* expression were thawed in 1 L of lysis buffer (PBS/25 mM EDTA/1 mM PMSF). Cells were disrupted by Tissuemizer (30 seconds) and the resulting slurry was passed through a microfluidizer twice. Insoluble matter was pelleted by centrifugation. Clarified lysate (250 mL at a time) was loaded onto a Protein G column (cat#17-0618-05, GE Healthcare) at 5 mL/min. The column was then washed with 100 mL of lysis buffer before eluting the bound Fab fragment of anti-PCSK9 antibody with 150 mL of elution buffer (0.58% acetic acid). 25 mL fractions were collected during elution. Fractions containing Fab fragment of anti-PCSK9 antibody were pooled after SDS PAGE analysis.

5 mL prepacked SPHP column (GE Healthcare, cat#17-1152-01) were equilibrated with 50 ml of Buffer A (20 mM MES pH5.5). Pooled fractions from the prior step were loaded onto the column at 3 mL/min. The column was washed with Buffer A to baseline. Bound Fab fragment was eluted with buffer B (20 mM MES pH 5.5, 1M NaCl) using a gradient from 0% to 100% buffer B in 20 column volumes. 2 mL fractions were collected during elution. The fractions containing the protein (determined using SDS-PAGE) were pooled and concentrated to 5 mL before loaded onto a 320 mL S75 gel filtration column that had been pre-equilibrated with sizing buffer (20 mM Hepes 7.2, 150 mM NaCl). The sizing buffer was run continuously at 1.5 mL/min for 220 mins while collecting 2 mL fractions. The peak fractions (A280) were analyzed using SDS-PAGE.

Human PCSK9 (Genbank EF692496) complementary deoxyribonucleic acids (cDNAs) containing a histidine (His)$_8$ C-terminal tag (SEQ ID NO:32) were inserted into a mammalian expression vector (pRK5) with a cytomegalovirus (CMV) promoter using standard molecular biology techniques. Protein was expressed by transient transfection of Chinese hamster ovary (CHO) cells and purified from conditioned media using affinity chromatography on a nickel-nitrilotriacetic-agarose column (Qiagen) followed by gel filtration on a SEPHACRYL® S-200 column (GE Healthcare). The correct masses of purified proteins were verified by sodium dodecyl sulfate polyacrylamide gel electrophoresis (SDS-PAGE) and the accuracy of amino acid sequences were confirmed by N-terminal sequencing.

The purified Fab fragment of anti-PCSK9 antibody and 6.9 mg of PCSK9 protein were mixed in 2-fold molar excess of the Fab fragment and incubated at 4° C. for 1 hour before concentration to 5 mL. The concentrated mixture was then loaded onto a SUPERDEX® 200 size exclusion column (cat#17-1071-01, GE Healthcare) pre-equilibrated with sizing buffer. The sizing buffer was continuously run at 1.5 mL/min for 220 mins while collecting 2 mL fractions. The peak fractions (A280) containing both PCSK9 and Fab fragment of anti-PCSK9 antibody (SDS-PAGE) were pooled and concentrated to 20 mg/mL. The concentrated complex was then used to set up crystallization trials. Initial crystals were formed from a 1:1 mixture between protein and reservoir containing 1.3 M potassium/sodium phosphate at pH 7 using sitting drops. Crystals were optimized by varying the protein: reservoir ratio in hanging drops. A selected crystal was treated with mother liquor supplemented with 25% glycerol and preserved in liquid nitrogen.

Structure Determination of the PCSK9:Fab Fragment of Anti-PCSK9 Antibody Complex Diffraction data extending to about 3.5 Å resolution were collected at synchrotron beamline SSRL 7-1 and integrated and scaled in space group 1222. Approximate phases were obtained by the method of molecular replacement, using the previously reported structure of PCSK9 (Hampton et al., *PNAS* 104:14609-9 (2007), pdb accession code 2QTW) and the previously reported structure of an antibody Fv fragment (Eigenbrot et al., *J Mol Biol* 229:969-95 (1993), pdb accession code 1FVC). The constant region of Fab fragment of anti-PCSK9 antibody was placed as a rigid body using a part of a previously reported homologous structure (Eigenbrot et al. supra, pdb accession code 1FVD) after partial refinement had improved phases. The final refined structure has crystallographic R-values of 25 & 30%. Data collection and refinement statistics appear in Table 1 below.

TABLE 1

| Data collection | |
| --- | --- |
| space group | I222 |
| unit cell (Å, °) | a = 92.283, b = 142.523, c = 253.983 |
| $V_M$ (Å$^3$/Dalton) | 2.8 |
| Resolution (Å) | 40-3.5 (3.63-3.50) |
| Rsym$^{a,b}$ | 0.184 (0.807) |
| Number of observations | 157526 |
| Unique reflections | 21579 |
| Completeness (%)$^b$ | 100 (100) |
| I/σI$^b$ | 11 (2.6) |
| Wilson B (Å$^2$) | 58 |
| Refinement | |
| Resolution (Å) | 40-3.5 |
| Number of reflections (F > 0σ(F)) | 20644 |
| Final R$^c$, R$_{FREE}$ | 0.247, 0.295 |
| complexes/asymmetric unit | 1 |
| protein residues | 994 |
| solvent molecules | 0 |
| atoms | 7463 |
| Mean B-factor (Å$^2$) | 86 |
| Rmsd bonds (Å) | 0.007 |
| Rmsd angles (°) | 1.1 |
| Rmsd bonded Bs (Å$^2$) | 2.4/1.9 |
| Number of TLS groups | 4 |
| Ramachandran (%) | 81.5/16.8/0.6/1.1 |

$^a$Rsym = Σ||I| − |<I>||/Σ|<I>|, where I is the intensity of a single observation and <I> the average intensity for symmetry equivalent observations.
$^b$In parenthesis, for the highest resolution shell.
$^c$R = Σ|Fo − Fc|/Σ|Fo|, where Fo and Fc are observed and calculated structure factor amplitudes, respectively. R$_{FREE}$ is calculated as R for reflections sequestered from refinement.

Determination of Epitope on PCSK9 from the X-Ray Structure

A 4 Å criterion was applied using the molecular analysis program PYMOL™. PCSK9 residues within 4 Å of any part of the Fab fragment of anti-PCSK9 antibody were determined as an epitope. Based on the analysis, the epitope comprises one or more of the following residues: R194, E195, D238, A239, A341, Q342, E366, D367, I369, S376, T377, C378, F379, S381 and H391 of human PCSK9.

Example 11

Human Clinical Trial, Single and Multiple Ascending Doses

A randomized, double-blind, placebo-controlled, single and multiple dose study was conducted to evaluate, primarily, the safety and tolerability of single and multiple (four weekly) doses of study drug (YW508.20.33b reformatted into human IgG$_1$ having a heavy chain with SEQ ID NO: 35 and a light chain with SEQ ID NO: 36) administered by subcutaneous (SC) injection to healthy volunteers with elevated serum low-density lipoprotein cholesterol (LDL-c) concentration. 80 healthy adult volunteers (men and women) with elevated serum LDL-c concentrations (130-220 mg/dL) were randomized into 10 cohorts each containing 8 subjects. Subjects in each cohort were randomized to receive either study drug or placebo (6 active and 2 placebo subject per cohort).

Figure 14:
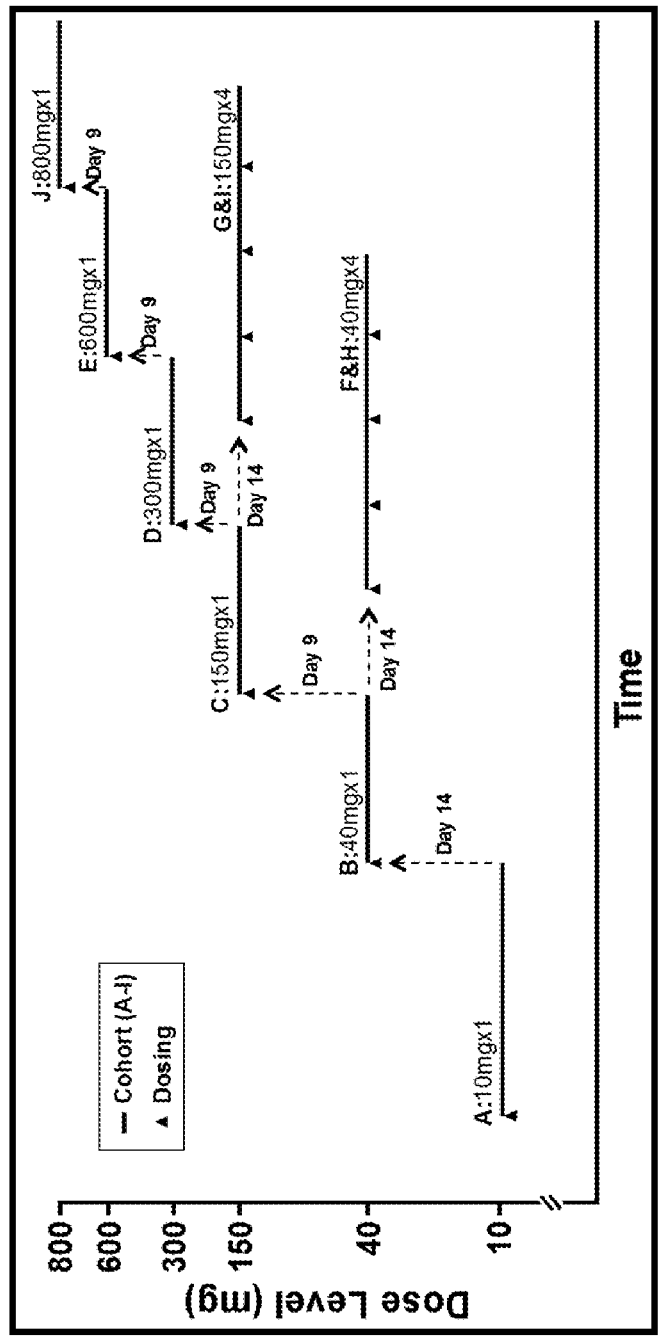
FIG. 14 shows a schematic of the Phase I trial design including cohorts A-J. Each cohort included six patients treated with the active agent and two patients treated with placebo, for a total of 8 patients per cohort and 80 total patients.

The cohorts were dosed as shown in FIG. 14 and the Table 2. All doses were administered subcutaneously using syringes, typically in the abdomen or thigh. The drug product was formulated as 150 mg/mL antibody in 200 mM arginine succinate, 0.02% polysorbate 20, pH 5.5. For the multiple dose cohorts, study drug was administered once per week for four consecutive weeks. The statin cohorts (H and I), were initially administered atorvastatin at 20 mg once a day orally for at least 7 days, followed by a safety and tolerability assessment. If the 20 mg dose was well tolerated, the dose was increased to 40 mg daily and continued for a minimum of 21 days prior to initiation of study drug on Day 1. Subjects in cohorts H and I continued atorvastatin (40 mg PO daily) until and including Day 35. Treatment was discontinued for any subject whose direct LDL-c level fell below 25 mg/dL at any point during the study.

TABLE 2

Overview of Study Dose Cohorts.

| Cohort | Dose (mg) | Total doses administered | Follow-up duration[a] | Atorvastatin |
|---|---|---|---|---|
| A | 10 | 1 | 8 weeks | No |
| B | 40 | 1 | 8 weeks | No |
| C | 150 | 1 | 12 weeks | No |
| D | 300 | 1 | 12 weeks | No |
| E | 600 | 1 | 16 weeks | No |
| F | 40 | 4 | 16 weeks | No |
| G | 150 | 4 | 16 weeks | No |
| H | 40 | 4 | 16 weeks | Yes |
| I | 150 | 4 | 16 weeks | Yes |
| J | 800 | 1 | 16 weeks | No |

[a] = Time between first dose of study drug and final study visit.

Subjects were followed for 8 to 16 weeks following initiation of study drug with frequent safety, PK and PD assessments. The following data were evaluated: safety outcomes (adverse events, abnormalities in hematology, clinical chemistry, and urinalysis, and incidence of anti-therapeutic antibodies), pharmacokinetic (PK) profile (including $C_{max}$, total serum apparent clearance (CL/F), apparent volume of distribution (V/F), total exposure (AUC), $t_{max}$, $t_{1/2}$, and dose proportionality (based on AUC)), pharmacodynamics outcomes (percent and absolute reduction from baseline in LDL-c at day 15 in single dose cohorts and day 36 in multiple dose cohorts), and percent and absolute change from baseline over time in total cholesterol, LDL-c, HDL-c, non-HDL-c, triglycerides, and lipid particle sub-fractions.

Early results from the study have not identified a drug-related, clinically significant pattern of adverse events. There were no serious or severe adverse events, no discontinuations for adverse events, and no dose-limiting toxicities. The tested doses have not defined a maximum tolerated dose. Two moderate adverse events have been reported: one headache (study drug-treated subject in the 10-mg single dose cohort) and one radius fracture (study drug-treated subject in the 600-mg single dose cohort). Five study drug-treated subjects, all in multiple dose cohorts and treated with concomitant atorvastatin, were discontinued from study drug therapy because of LDL-c levels below the protocol-specified threshold of 25 mg/dL. There were no associated adverse events in these subjects.

Figure 15:
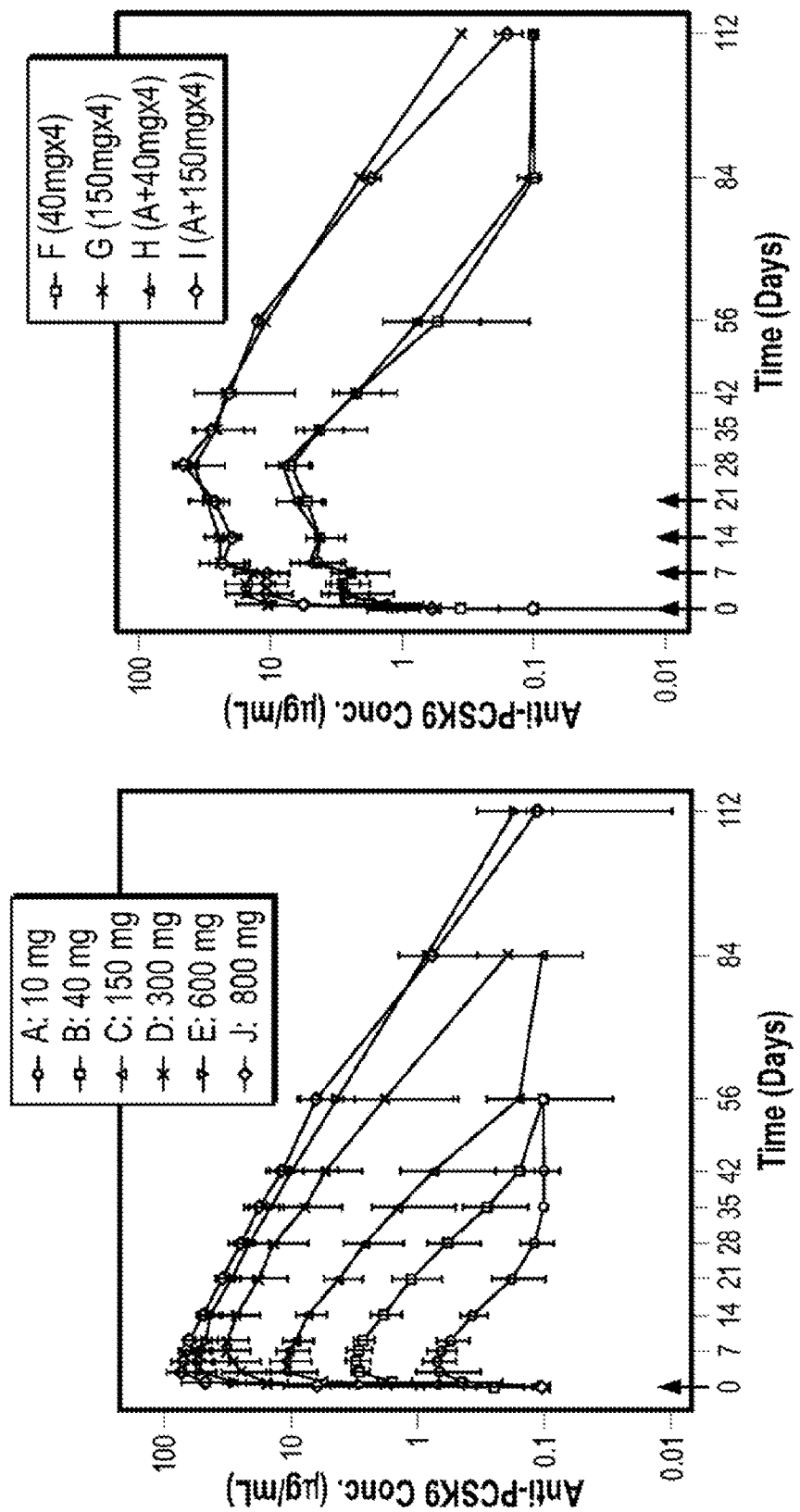
FIG. 15 shows pharmacokinetic data for study cohorts A-J. Results from the single dose cohorts A-E and J are shown in the left panel and results from the multiple dose cohorts F-I are shown in the right panel. Red arrows indicate timing of drug administration.

As shown in FIG. 15 (left panel), there was a dose related increase in exposure from 10-600 mg for study drug. No differences in PK were observed between statin treated and untreated groups (FIG. 15, right panel). There was a saturable clearance of study drug with a Km of 5.94 ug/mL.

Figure 16:
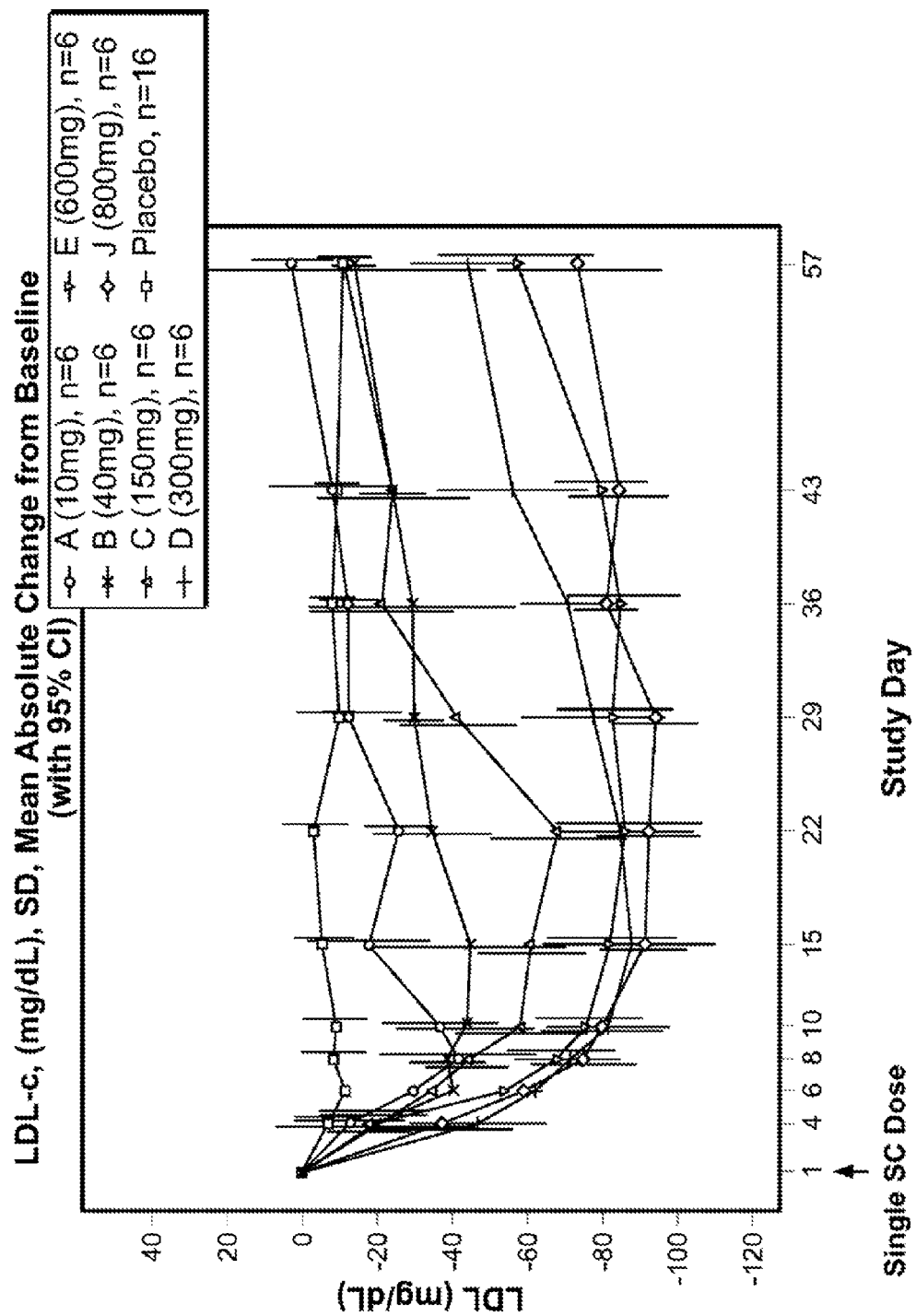
FIG. 16 shows mean absolute change from baseline in LDL-c (mg/dL) levels for the single dose cohorts.
Figure 17:
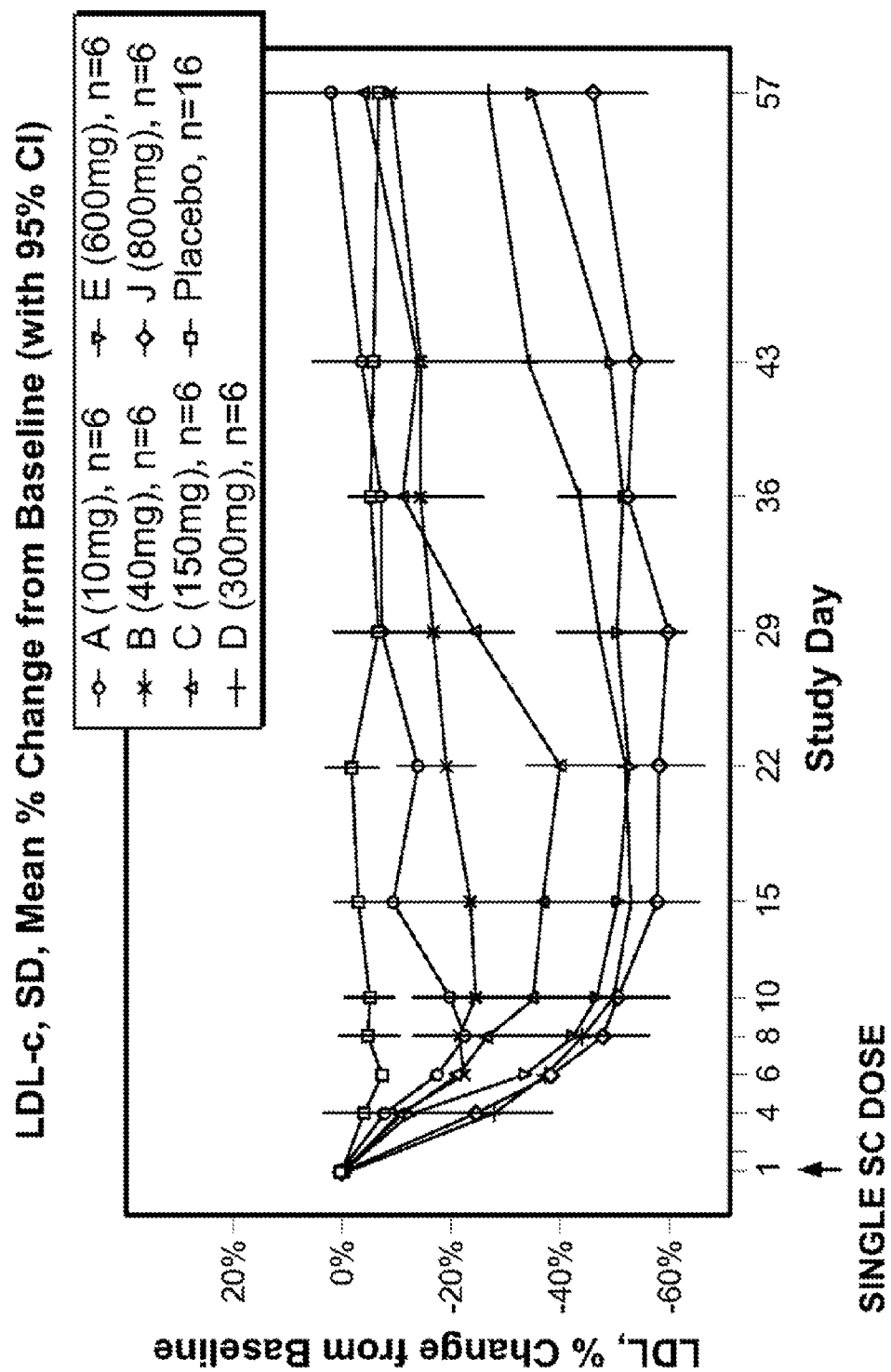
FIG. 17 shows mean percent change in baseline in LDL-c levels for the single dose cohorts.
Figure 18:
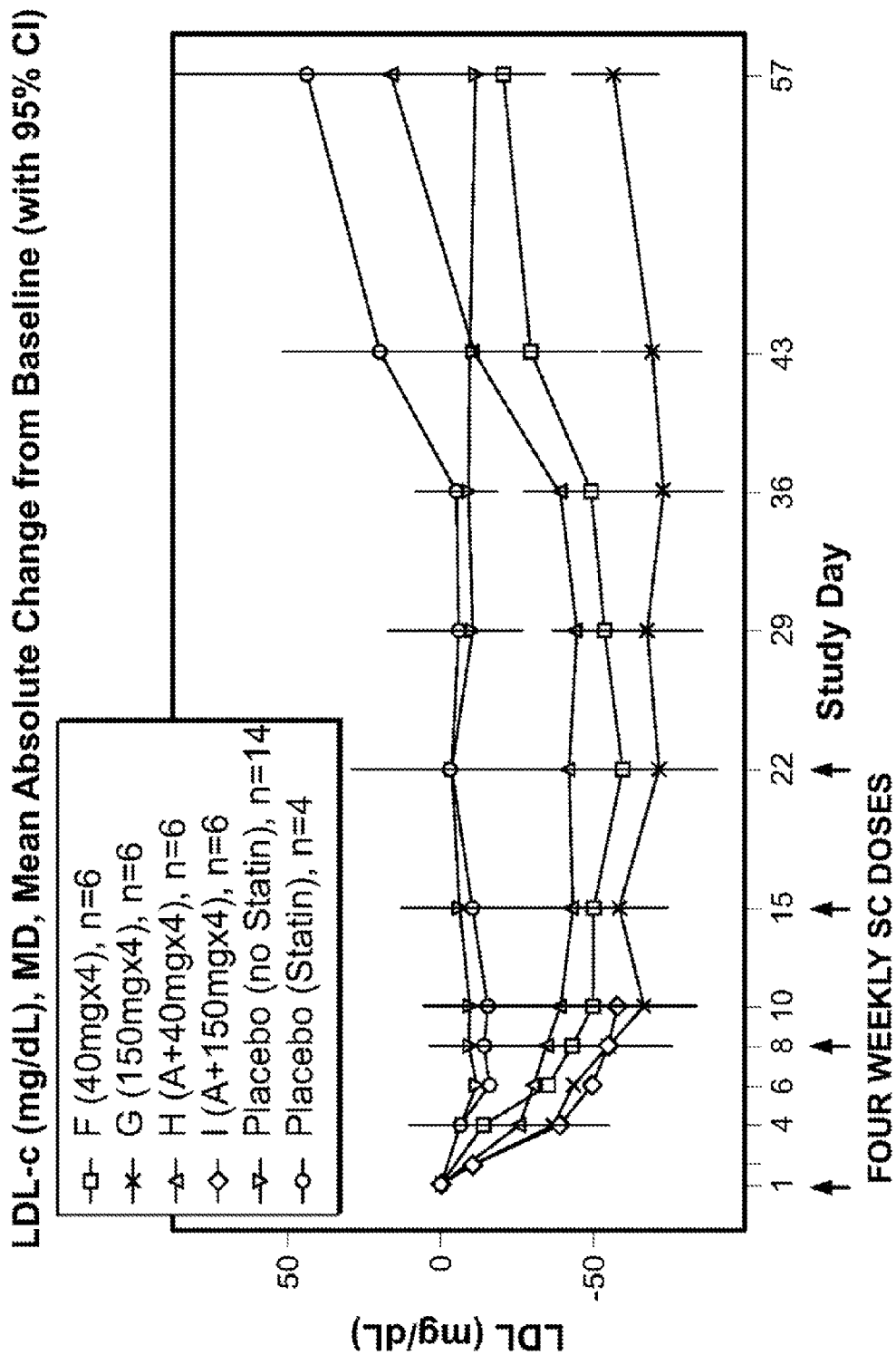
FIG. 18 shows mean absolute change from baseline in LDL-c (mg/dL) levels for the multiple dose cohorts.
Figure 19:
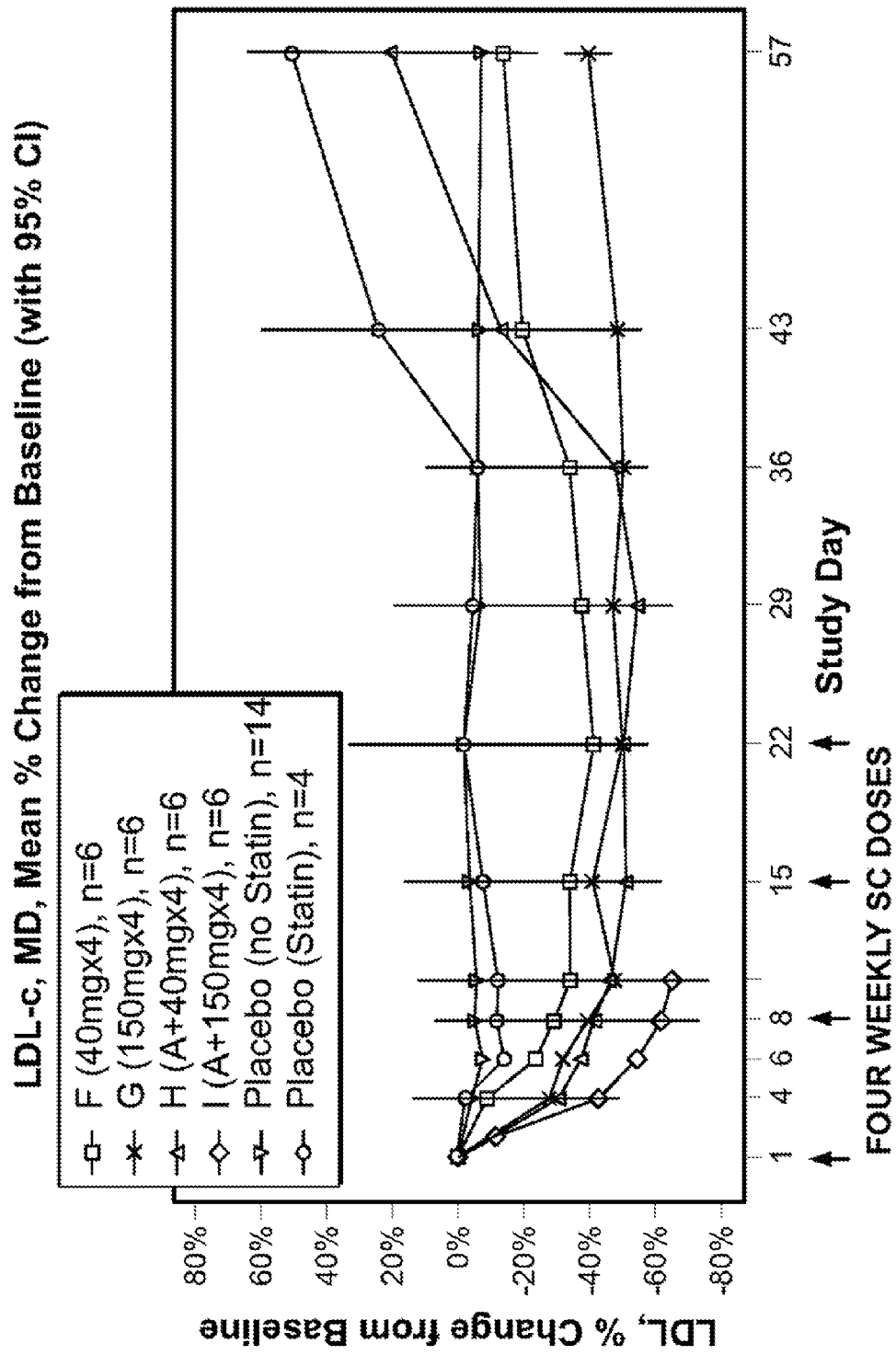
FIG. 19 shows mean percent change in baseline in LDL-c levels for the multiple dose cohorts.

As shown in FIGS. 16-19 and Tables 3 and 4, study drug produced clinically meaningful LDL-c reductions in healthy volunteers, alone and in combination with statin. Pharmacodynamic (PD) data showed a dose-dependent reduction in LDL-c that was statistically significant in all cohorts except the 10 mg single dose cohort. LDL-c decreased by 80-90 mg/dL in the highest dose groups (300-800 mg in the single dose cohorts), from an average baseline LDL-c of 160-170 mg/dL. Similar reductions in LDL-c levels were seen between atorvastatin (cohorts H and I) and non-statin cohorts (cohorts F and G) (see FIGS. 18 and 19 and Tables 3 and 4). The differences between cohorts I and G (at day 10) and F and H (at day 36) are not statistically significant. As shown in FIGS. 16 and 17, at doses≥300 mg, the maximal LDL-c effect appears to saturate but the duration of the effect lengthens. The data support monthly or less frequent dosing.

TABLE 3

Absolute Change in LDL-c Levels from Baseline in Single and Multiple Dose Cohorts.

| | Mean (SD) Change in LDL (mg/dL) | | |
|---|---|---|---|
| Arm | Active | Placebo | P-value[a] |
| Single Dose (at day 15) | | | |
| A (10 mg) | −18 (21) | −5.6 (15) | 0.22 |
| B (40 mg) | −45 (32) | | 0.03 |
| C (150 mg) | −61 (17) | | <0.001 |
| D (300 mg) | −88 (28) | | <0.001 |
| E (600 mg) | −82 (22) | | <0.001 |
| J (800 mg) | −91 (14) | | <0.001 |
| Multiple Dose (at day 36) | | | |
| F (40 mg × 4) | −50 (28) | −9.7 (13) | 0.016 |
| G (150 mg × 4) | −71 (26) | | 0.001 |
| H (A[b] + 40 mg × 4) | −38 (10) | −5 (14) | 0.009 |
| I (A[b] + 150 mg × 4) | N/A[c] | −15 (21) | N/A[c] |

[a] = The differences between cohorts I and G (at day 10) and F and H (at day 36) are not statistically significant.
[b] = A is Atorvastatin.
[c] = Multiple subjects in cohort I (150 mg × 4 + Atorvastatin) were discontinued after day 10 due to LDL levels falling below the protocol threshold of <25 mg/dL.

TABLE 4

Percent Change in LDL-c Levels from Baseline in Single and Multiple Dose Cohorts.

| | Mean % (SD) Change in LDL | | |
|---|---|---|---|
| Arm | Active | Placebo | P-value |
| Single Dose (at day 15) | | | |
| A (10 mg) | −9.4 (11) | −3.7 (10) | 0.3 |
| B (40 mg) | −23 (12) | | 0.008 |
| C (150 mg) | −37 (11) | | <0.001 |
| D (300 mg) | −53 (10) | | <0.001 |
| E (600 mg) | −51 (18) | | <0.001 |
| J (800 mg) | −58 (4) | | <0.001 |
| Multiple Dose (at day 36) | | | |
| F (40 mg × 4) | −34 (19) | −6.2 (8) | 0.016 |
| G (150 mg × 4) | −49 (10) | | 0.001 |
| H (A[a] + 40 mg × 4) | −48 (17) | −5.7 (16) | 0.005 |
| I (A[a] + 150 mg × 4) (at day 10) | −65 (13) | −12 (24) | 0.014 |

[a] = A is Atorvastatin.

Example 12

Human Clinical Trial in Patients with Coronary Heart Disease (CHD) or at High Risk of CHD A randomized, double-blind, placebo-controlled, study of study drug (YW508.20.33b reformatted into human IgG$_1$ having a heavy chain with SEQ ID NO: 35 and a light chain with SEQ ID NO: 36) will be conducted to evaluate the safety and efficacy of study drug on top of standard-of-care (SOC) statin in patients with LDL-c levels of 90-250 mg/dL and either coronary heart disease (CHD) or a CHD risk equivalent. Approximately 224 patients (adult men and women) with serum LDL-c concentrations of 90-250 mg/dL and either CHD or a CHD risk equivalent will be randomized to one of five study arms to be administered study drug or a placebo arm, as set forth below in Table 5. All doses will be administered subcutaneously using syringes. The drug product is formulated as 150 mg/mL antibody in 200 mM arginine succinate, 0.02% polysorbate 20, pH 5.5.

TABLE 5

Overview of Study Dose Cohorts.

| | Study Drug Dose Regimen | | Planned Number of Patients | |
|---|---|---|---|---|
| Arm | Dose (mg) | Frequency (weeks) | Active Drug | Placebo |
| A | 400 | 4 | 56 | — |
| B | 200 | 8 | 14 | — |
| C | 400 | 8 | 28 | — |
| D | 800 | 8 | 56 | — |
| E | 800 | 12 | 14 | — |
| F | Placebo | — | — | 56 |
| (A-F) total | — | — | 168 | 56 |

The study will include consecutive periods for screening (0-4 weeks), run-in (0-6 weeks, if necessary), treatment (24 weeks; Days 1-169), and follow-up (12 weeks). The study completion visit at the end of the follow-up period (Day 253) will occur 16 weeks after the final dose of study drug (Day 141). All patients, regardless of treatment assignment, will receive SOC treatment, including statins unless statins are not tolerated. All patients will continue SOC statin therapy throughout the treatment and follow-up periods, at the same dose they were receiving during the run-in period and at enrollment. Other prescription and over-the-counter (OTC) lipid-modifying therapies are not permitted. Patients who have been taking a stable dose of SOC statin therapy (or no statin and have documented intolerance to two or more statins) and no other lipid-modifying therapy for at least 4 weeks (or 6 weeks in the case of fibrates) at the time of screening will not require a run-in period.

Patients will be monitored to determine efficacy based on absolute change from baseline in LDL-c concentration at day 169. In addition, patients will be monitored to determine secondary efficacy outcomes including absolute change from baseline in LDL-c concentration for each arm at the nadir for that arm; average value over time of the change in LDL-c (absolute and percent change) for each arm, up to Day 169, weighted by the number of weeks between consecutive LDL-c measurements; percent change from baseline in LDL-c concentration at Day 169 and at the nadir for each arm; percent and absolute change from baseline in LDL-c concentration at all other designated timepoints; and percent and absolute change from baseline in total cholesterol, non-HDL-c, and apolipoprotein B at Day 169 and at the nadir for each arm. Finally, patients will also be monitored for safety including incidence, nature, and severity of adverse events; incidence and nature of changes in vital signs, physical findings, and clinical laboratory results during and following study drug administration; and incidence of anti-therapeutic antibodies directed against study drug.

The safety of low LDL-c values will be assessed regularly in a blinded, exploratory manner. Study drug will be withheld from patients with two consecutive LDL-c values of <15 mg/dL. This will not be considered an adverse event. Such patients will be treated with placebo instead, in blinded fashion, until LDL-c increases to ≥50 mg/dL, after which these patients will be switched to the lowest dosage (200 mg every 8 weeks). All doses of active drug or placebo will be given according to the study drug administration schedule, that is, on Days 1, 29 (±2 days), 57 (±2 days), 85(±2 days), 113 (±4 days), and 141 (±4 days) only.

The primary efficacy outcome measure is the change from baseline in LDL-c at Day 169. Baseline LDL-c is defined as the average of the last two measurements collected before the first dose of study drug. The treatment comparisons between the study drug doses and between each of the study drug doses and placebo will be based on an analysis of covariance (ANCOVA), which will be performed through a linear regression model adjusting for two covariates: baseline LDL-c concentration (<120 mg/dL, ≥120 mg/dL) and diabetes status (yes, no). The confidence intervals, as well as the least-square estimates from the ANCOVA models, will be used to aid in the interpretation of the study results.

The eligibility criteria define a population of patients with high cardiovascular and CHD risk based on risk categories in the European Society of Cardiology (ESC)/European Atherosclerosis Society (EAS) and National Cholesterol Education Program Adult Treatment Panel III (NCEP ATP III) lipid-lowering guidelines. The study aims to enroll patients who qualify for a therapeutic target LDL-c level of 70 mg/dL according to these guidelines, but who have not come close to this goal despite SOC statin therapy, either because SOC is insufficient or because statins were not tolerated. These patients are in need of additional safe and effective LDL-c-lowering therapies.

CHD refers to a history of documented myocardial infarction, prior coronary revascularization procedure (percutaneous coronary intervention or coronary artery bypass graft), or prior coronary angiography (invasive coronary angiography or cardiac computed tomography coronary angiography) demonstrating at least one coronary atherosclerotic lesion with 50% diameter stenosis.

A CHD risk-equivalent condition is at least one of the following:
1. One or more forms of clinical atherosclerotic disease:
    a. Peripheral arterial disease (previously documented ankle/brachial blood pressure index<0.85, prior percutaneous or surgical peripheral arterial revascularization procedure, prior non-traumatic amputation of a lower extremity due to peripheral artery disease, or 50% diameter stenosis on prior vascular imaging),
    b. Carotid artery disease (previously documented carotid atherosclerotic lesion with ≥50% diameter stenosis on imaging or prior cutaneous or surgical carotid revascularization procedure),
    c. Prior ischemic stroke, documented by CT or MRI brain imaging, not due to embolism of cardiac origin (e.g., atrial fibrillation, valvular disease, or left ventricular mural thrombus) in the opinion of the investigator, or
    d. Abdominal aortic aneurysm with prior surgical or endovascular repair.
2. Diabetes mellitus type 2,
3. Diabetes mellitus type 1 with target organ damage (retinopathy, neuropathy, or nephropathy including microalbuminuria, as determined by the investigator),
4. Moderate to severe chronic kidney disease (manifested by an estimated glomerular filtration rate of 15-60 mL/min/

1.73 m² using the Modification of Diet in Renal Disease equation consistently over at least three measurements spanning at least 3 months, including screening laboratories), or 5. Two or more of the CHD risk factors listed below AND either an absolute 10-year risk of a CHD event≥20% (as determined by the National Cholesterol Education Program Adult Treatment Panel III guideline modification of the Framingham risk score) or a 10-year risk of a first fatal atherosclerotic event≥10% (determined by the Systemic Coronary Risk Estimation system):
  a. Age≥45 years for men or 55 years for women,
  b. Current cigarette smoking (within 1 month),
  c. Hypertension (screening systolic blood pressure≥140 mmHg, diastolic blood pressure≥90 mmHg, or taking an antihypertensive medication to treat hypertension)
  d. Low HDL cholesterol (<40 mg/dL), or
  e. Family history of premature CHD (myocardial infarction or coronary revascularization in a male first-degree relative<55 years of age or in a female first-degree relative<65 years of age).

Standard-of-care statin therapy refers to a therapy meeting one of the following conditions: (1) high-dose simvastatin (40 mg daily), atorvastatin (40-80 mg daily), or rosuvastatin (20-40 mg daily), (2) low-dose simvastatin, atorvastatin, or rosuvastatin and documented intolerance of a high dose of that statin or of any dose of another statin, (3) other statin (any dose) and documented intolerance of simvastatin, atorvastatin, or rosuvastatin (any dose), or (4) no statin and documented intolerance of at least two statins (any statin, any dose).

Diabetes status will be determined based on the presence of any one of the following, according to patient medical record or history, or to screening laboratory test results: (1) $HbA_{1c}$>6.5%, (2) fasting plasma glucose≥126 mg/dL (7.0 mmol/L), (3) prior 2-hour plasma glucose≥200 mg/dL (11.1 mmol/L) during an oral glucose tolerance test (the test should be performed as described by the World Health Organization, with use of a glucose load containing the equivalent of 75 g of anhydrous glucose dissolved in water), or (4) currently on an oral or injectable therapy for a diagnosis of diabetes mellitus.

Example 13

Development of Stable, High Concentration Antibody Formulation

Initial clinical studies (see Examples 11 and 12) were carried out using a formulation of anti-PCSK9 antibody (YW508.20.33b reformatted into human IgG₁ having a heavy chain with SEQ ID NO: 35 and a light chain with SEQ ID NO: 36) formulated at 150 mg/mL antibody in 200 mM arginine succinate, 0.02% (w/v) polysorbate 20 at pH 5.5. However, a formulation with a higher protein concentration (≥200 mg/mL) and increased stability was desired to facilitate administration of higher subcutaneous doses that could be delivered monthly or less frequently.

Viscosity of anti-PCSK9 Formulations

The viscosity of a 200 mM arginine succinate, 0.02% (w/v) PS20, pH 5.5 anti-PCSK9 formulation was evaluated at various protein concentrations. At each protein concentration, the viscosity was measured at 5, 15, 25 and 40° C. using a rheometer (Anton Paar Physica MCR 501) with a shear rate of 1000 l/s.

Figure 20:
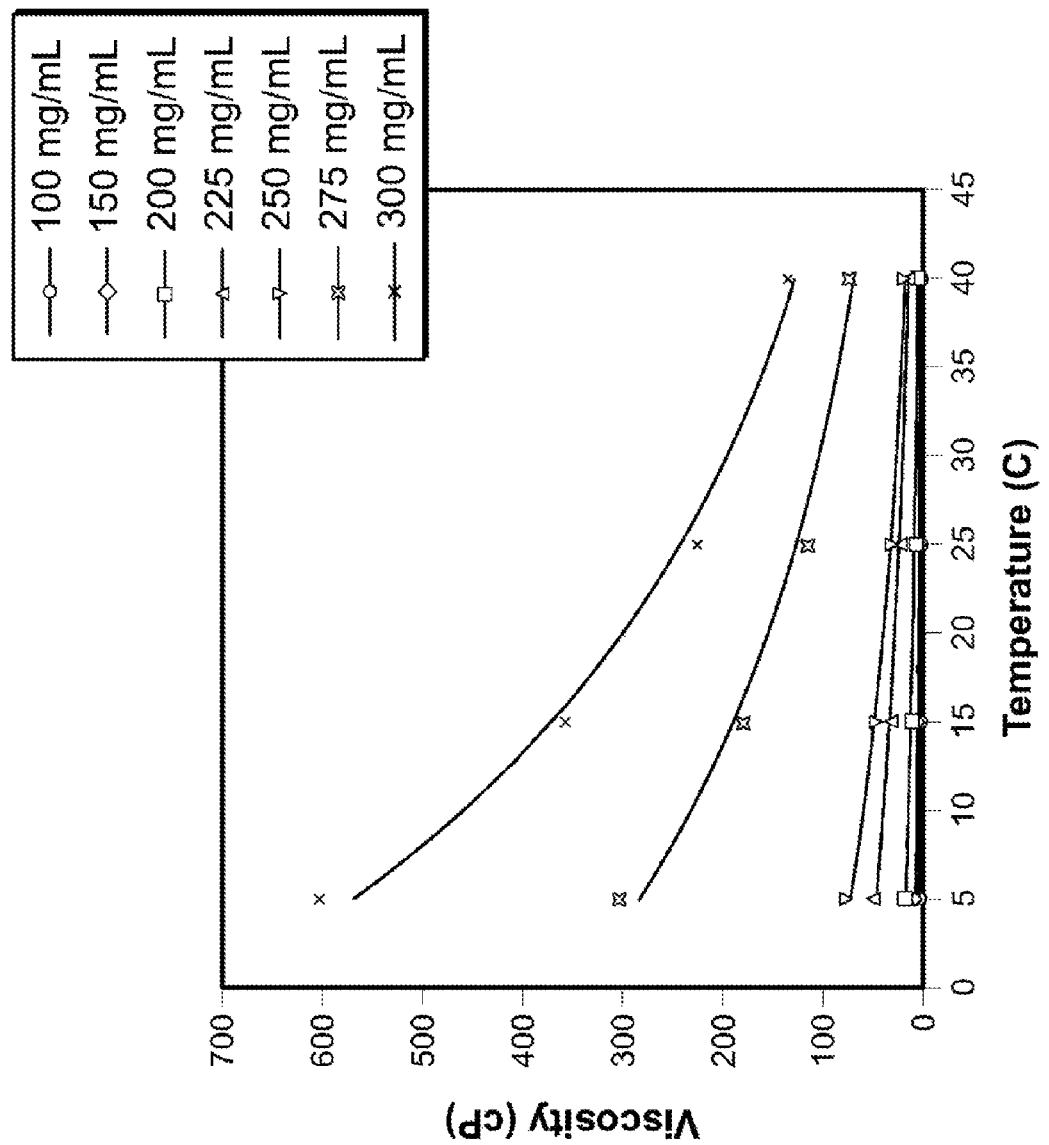
FIG. 20 shows the viscosity of anti-PCSK9 as a function of protein concentration in a formulation of 200 mM arginine succinate, 0.02% PS20, pH 5.5.

Viscosity is an important parameter for subcutaneous dosing of drug solution. A desirable viscosity limit for subcutaneous delivery using a syringe is <10 cP at ambient temperature. The viscosity of anti-PCSK9 at 100 to 300 mg/mL in 200 mM arginine succinate, 0.02% (w/v) PS20, pH 5.5 is presented in Table 6. For anti-PCSK9, viscosity is protein concentration and temperature dependent. As protein concentration increases, viscosity also increases. However, at each concentration, the viscosity can be lowered by increasing temperature. By increasing the protein concentration over 200 mg/mL, viscosity of anti-PCSK9 increased exponentially (FIG. 20). Therefore, anti-PCSK9 at 200 mg/mL was selected as the target concentration.

TABLE 6

Viscosity of anti-PCSK9 from 100 to 300 mg/mL antibody concentration.

| Temp (° C.) | Viscosity (cP)[1] | | | | | | |
|---|---|---|---|---|---|---|---|
| | 100 mg/mL | 150 mg/mL | 200 mg/mL | 225 mg/mL | 250 mg/mL | 275 mg/mL | 300 mg/mL |
| 5 | 4.6 ± 0.27 | 8.0 ± 0.16 | 18.6 ± 0.17 | 50.2 ± 0.99 | 76.9 ± 0.83 | 306 ± 5.8 | 603 ± 9.2 |
| 15 | 3.1 ± 0.10 | 5.2 ± 0.08 | 11.7 ± 0.15 | 31.9 ± 0.33 | 46.7 ± 0.91 | 179 ± 2.8 | 357 ± 4.8 |
| 25 | 2.5 ± 0.06 | 3.8 ± 0.09 | 8.3 ± 0.13 | 22.6 ± 0.14 | 31.0 ± 0.84 | 115 ± 0.6 | 225 ± 4.1 |
| 40 | 1.8 ± 0.01 | 2.7 ± 0.10 | 5.7 ± 0.26 | 15.5 ± 0.2 | 18.8 ± 0.63 | 74.8 ± 4.3 | 135 ± 3.2 |

[1]200 mM arginine succinate, 0.02% PS20, pH 5.5.

Agitation Study

An agitation study was performed to assess the minimum amount of surfactant required to prevent or minimize aggregation of anti-PCSK9 at 150 mg/mL in 200 mM arginine succinate, pH 5.5. Polysorbate 20 (PS20) was added to the formulation to achieve concentrations of 0.01, 0.02, 0.04, 0.06, 0.08 and 0.1% (w/v). All samples were sterile filtered, and 0.5 mL of each sample was filled into 2-cc glass vial. Samples were agitated using GLAS-COL® benchtop shaker set at 50 cycles/min with a sample displacement of 11 cm for 24 hours at room temperature (RT). The appropriate sample controls (no shaking) in the corresponding configuration were placed in the same vicinity of the shaker. All samples were analyzed by size-exclusion chromatography (SEC) and turbidity by UV measurement at 340-360 nm absorbance (abs).

Figure 21:
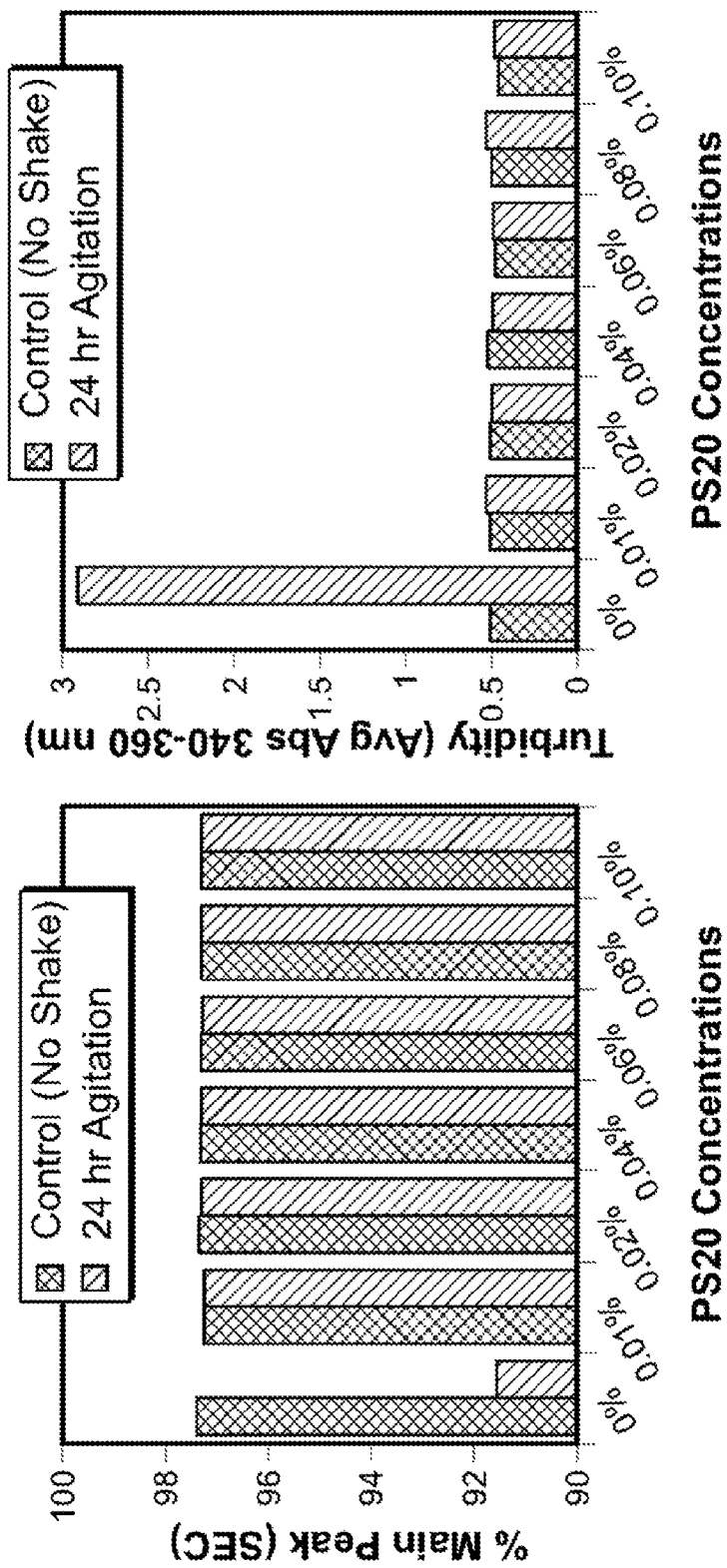
FIG. 21 shows size exclusion chromatography (SEC) (left panel) and turbidity (right panel) analyses for control and agitated anti-PCSK9 samples containing various concentrations of Polysorbate 20 (PS20) in 2 cc glass vials.

The results are presented in FIG. 21. Without PS20 in the formulation, the 24-hour agitated sample (at room temperature) had obvious visible changes when compared to the unshaken control vial. The agitated sample had a milky appearance with an increase in turbidity and a 6% decrease in SEC main peak. With the addition of ≥0.01% PS20 to the formulation, no differences were observed by SEC and turbidity measurement between the control (without agitation) and agitated samples in the vials. These results suggest that the use of 0.01% PS20 was sufficient to prevent agitation-induced aggregate formation of anti-PCSK9 at 200 mg/mL. However, a concentration of 0.02% PS20 was selected as the target concentration to account for potential degradation of the surfactant during product storage.

Oxidation Potential of Anti-PCSK9 Formulations

Oxidation of anti-PCSK9 was determined by trypsin-peptide map and the site(s) of oxidation was characterized by LC-MS. Oxidation of anti-PCSK9 was induced by elevated temperature, light and oxidizing agents such as hydrogen peroxide and 2,2'-Azobis(2-amidinopropane)dihydrochloride (AAPH). The degradation conditions for preparing the oxidative samples are summarized in Table 7. These oxidized anti-PCSK9 samples were also evaluated for possible potency loss due to oxidation by measuring its ability to inhibit PCSK9 binding to low density lipoprotein receptor domain Fc (LDLR$_D$-Fc) fusion protein as described in Example 3.

For peptide mapping, samples were reduced with 1M dithiothreitol, alkylated with 2.9 M iodoacetamide, and buffer exchanged before digestion. Trypsin was used for a 1.5 hour digestion at 37° C. using an enzyme to protein ratio of 1:25. The digestion was quenched with 10% trifluoroacetic acid (TFA) to a final pH 2-3. The resulting peptide digestion mixture was analyzed by reverse-phase liquid chromatography with detection by mass spectrometry (LC-MS) with a LTQ ORBITRAP XL™. The peptide map utilized a linear gradient from 0-40% over 160 minutes at 0.25 mL/min in conjunction with a Phenomenex JUPITER® C18 column (5 µm, 2×250 mm, 300 Å) maintained at 55° C. Mobile phases A and B consisted of 0.1% TFA in water and 0.09% TFA in acetonitrile respectively. Peptides were also detected at 214 and 280 nm abs before MS analysis. LC-MS data was processed by MASCOT® software to identify peptides and respective oxidation sites of anti-PCSK9. Amount of oxidation in a sample was expressed as "total oxidation per site" or accumulative oxidation since Trp and Met produce multiple oxidation products and/or oxidation states.

Figure 22:
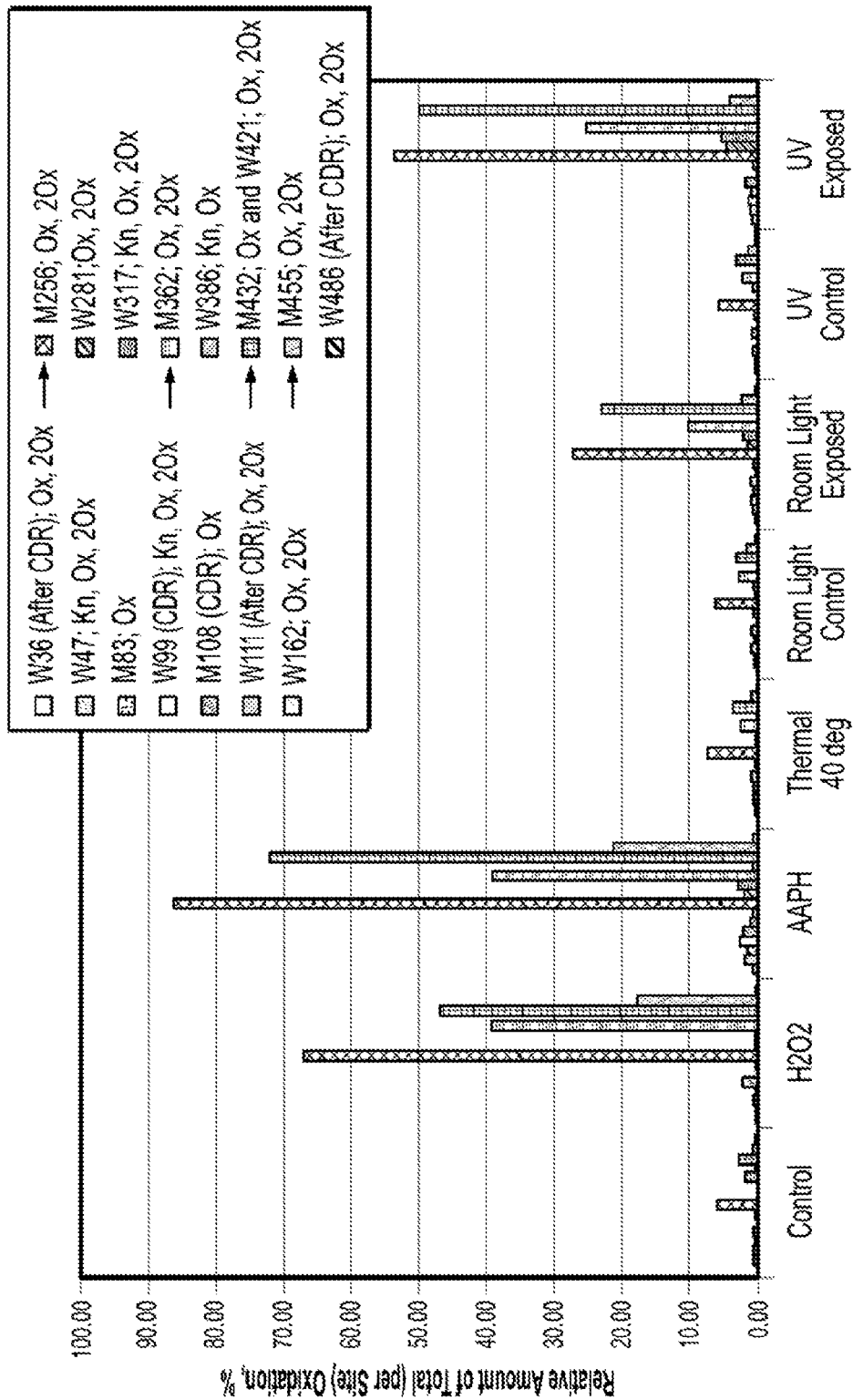
FIG. 22 shows oxidation of methionine and tryptophan residues in anti-PCSK9 under various conditions by peptide mapping.
Figure 23:
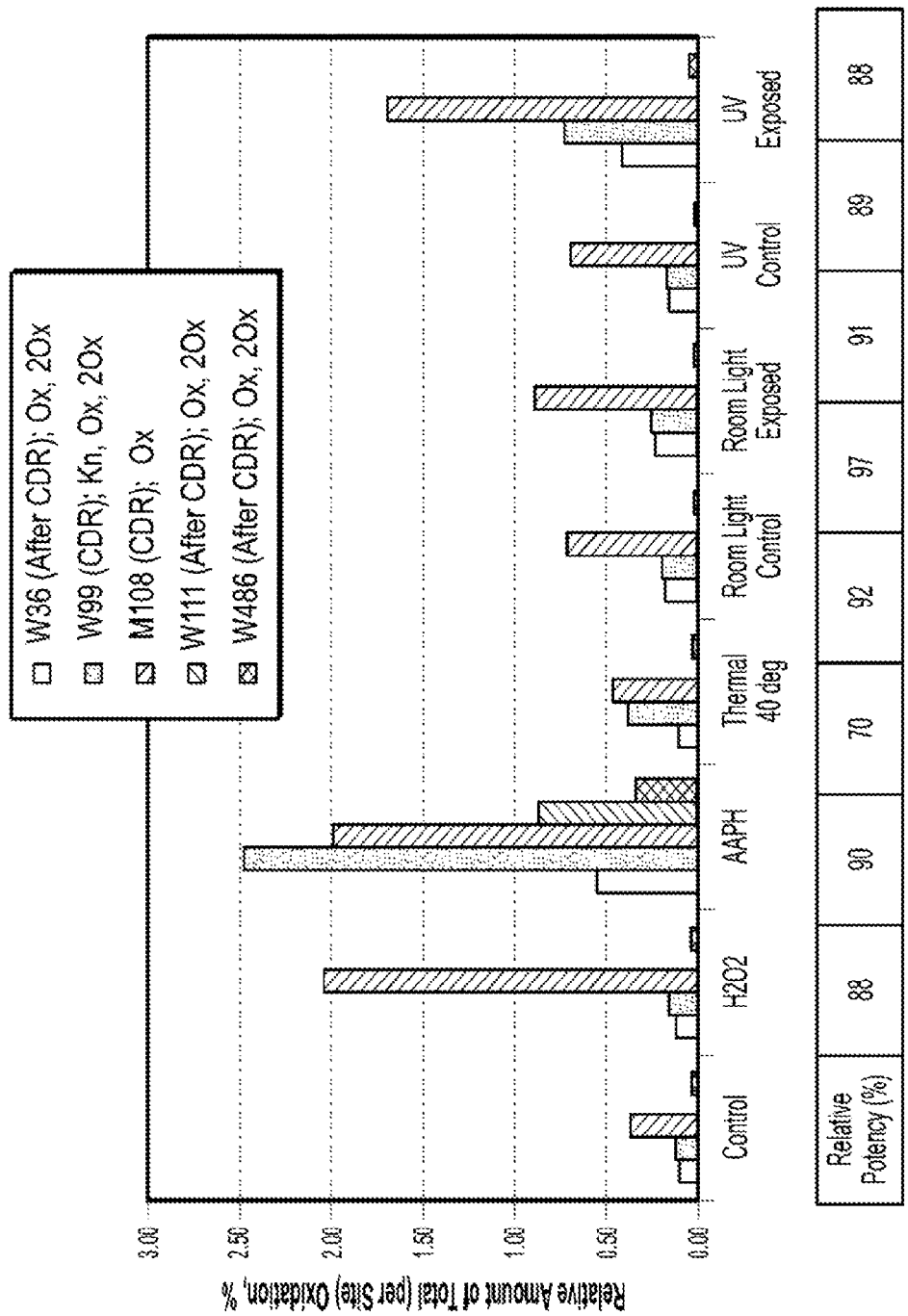
FIG. 23 shows oxidation of methionine and tryptophan residues in and adjacent to CDRs of anti-PCSK9 under various conditions by peptide mapping.

Methionine (Met/M) and Tryptophan (Trp/W) are the two common amino acid residues that are easily oxidized in protein drug products. $W_{99}$ and $M_{108}$ located in the complementarity-determining region (CDR) III of the heavy chain and the three Trp residues ($W_{36}$, $W_{111}$ and $W_{486}$) adjacent to the CDRs are the potential oxidation sites of anti-PCSK9. Oxidation of these amino acid residues may result in loss of drug potency due to their proximity to the CDRs. Peptide mapping analysis of the degraded samples revealed that oxidation of anti-PCSK9 mainly occurred at $M_{256}$, $M_{362}$, $M_{432}$ and $M_{455}$ residues of the Fc portion (FIG. 22). When anti-PCSK9 was degraded by exposing to light (room or UV) and oxidizing agents such as $H_2O_2$ and AAPH, the relative amount of oxidation per site for Met or Trp residues in/adjacent to the CDR was less than 3% with no significant impact on potency (FIG. 23). Therefore, anti-PSCK9 is considered not susceptible to oxidation and the use of antioxidants in the protein formulation is not necessary.

TABLE 7

Anti-PCSK9 Degradation Conditions for Oxidation Analysis.

| Degradation Mode | Exposure Condition | Expected Degradation |
|---|---|---|
| Thermal | 2 weeks @ 40° C. | Oxidation |
| Light | 24 hours of Room Light 1.2 million lux hours | Photo-oxidation |
| Oxidizing Agents | 1000 ppM $H_2O_2$ (24 hours @ 5° C.) | Methionine Oxidation |
| | 5 mM AAPH (24 hours @ 40° C.) | Methionine + Tryptophan Oxidation | pH Profile and Excipient Studies

The effect of formulation pH and excipients on anti-PCSK9 was evaluated at a protein concentration of 200 mg/mL. A pH range of 5.0 to 6.5 in formulations containing arginine succinate, histidine HCl or histidine acetate as buffer species and arginine HCl or arginine acetate as solubilizers were assessed for accelerated stability at 40° C. (see Table 9) and viscosity at 5° C. and 25° C. (see Table 8). The following assays were used for the assessment: SEC, ion-exchange chromatography (IEC), capillary electrophoresis-sodium dodecyl sulfate (CE-SDS) and potency. A total of seven formulations were evaluated.

IEC was performed on an AGILENT® 1100 HPLC and utilized a Dionex PROPAC® WCX-10 column (4×250 mm) with mobile phase A (20 mM HEPES, pH 7.9) and gradient from 1%-34% mobile phase B (20 mM HEPES, 100 mM NaCl, pH 7.9) in 50 minutes at a flow-rate of 0.9 mL/min. The column was maintained at 35° C. The sample load was 40 µg, and the separation was monitored at 280 nm abs.

Effect of pH

Figure 24:
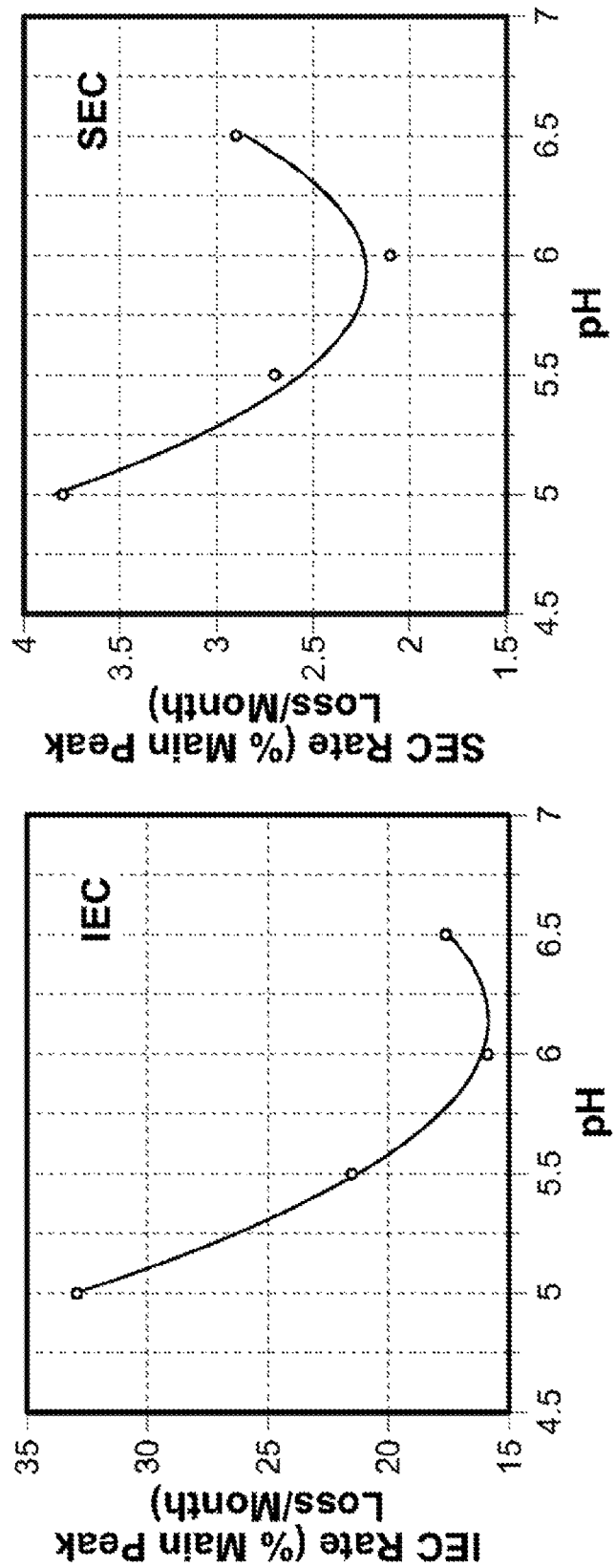
FIG. 24 shows ion exchange chromatography (IEC) (left panel) and SEC (right panel) pH rate profiles for 200 mg/mL anti-PCSK9 from pH 5.0 to 6.5 (200 mM arginine succinate, 0.02% PS20 at pH 5.0-6.0 or 20 mM histidine HCL, 160 mM arginine HCl, 0.02% PS20 at pH 6.5).

The effect of pH on stability of anti-PCSK9 at 200 mg/mL in 200 mM arginine succinate, 0.02% PS20 was evaluated from pH 5.0, 5.5 and 6.0. As analyzed by SEC, IEC and CE-SDS, increasing the formulation pH from 5.0 to 6.0 increased the stability of anti-PCSK9 after 1 month at 40° C. Compared to pH 5.0 and 5.5, the formulation at pH 6.0 had less acidic and basic peak formation as determined by IEC. The formulation at pH 6.0 also had a decrease in high molecular weight species (HMWS) as determined by SEC and low molecular weight species by determined by both SEC and CE-SDS. For the formulation at pH 6.5, anti-PCSK9 was formulated at 200 mg/mL in 20 mM histidine HCl, 160 mM arginine HCl, and 0.02% PS20. The degradation rates of anti-PCSK9 at 40° C. for all formulations at pH 5.0 to 6.5 are shown in Table 9 and the pH rate profiles for IEC and SEC are presented in FIG. 24. Based on the pH rate profiles and degradation rates, a target pH 6.0 was selected.

TABLE 8

Viscosity of anti-PCSK9 at 200 mg/mL in Various Formulations.

| | | | | Viscosity (cP) | |
|---|---|---|---|---|---|
| Formulation | Buffer | Stabilizer/Excipients | pH | 5° C. | 25° C. |
| 1 | 200 mM Arginine Succinate | 0.02% PS20 | 5.0 | 18.2 | 7.7 |
| 2 | | | 5.5 | 18.6 | 8.3 |
| 3 | | | 6.0 | 16.4 | 7.9 |
| 4 | 20 mM Histidine HCl | 160 mM Arginine HCl, 0.02% PS20 | 6.0 | 18.0 | 7.6 |
| 5 | | | 6.5 | 17.5 | 7.3 |
| 6 | 20 mM Histidine Acetate | 160 mM Arginine Acetate, 0.02% PS20 | 5.5 | 16.4 | 7.7 |
| 7 | | | 6.0 | 15.9 | 7.6 |

Effect of Buffer Species

Figure 26:
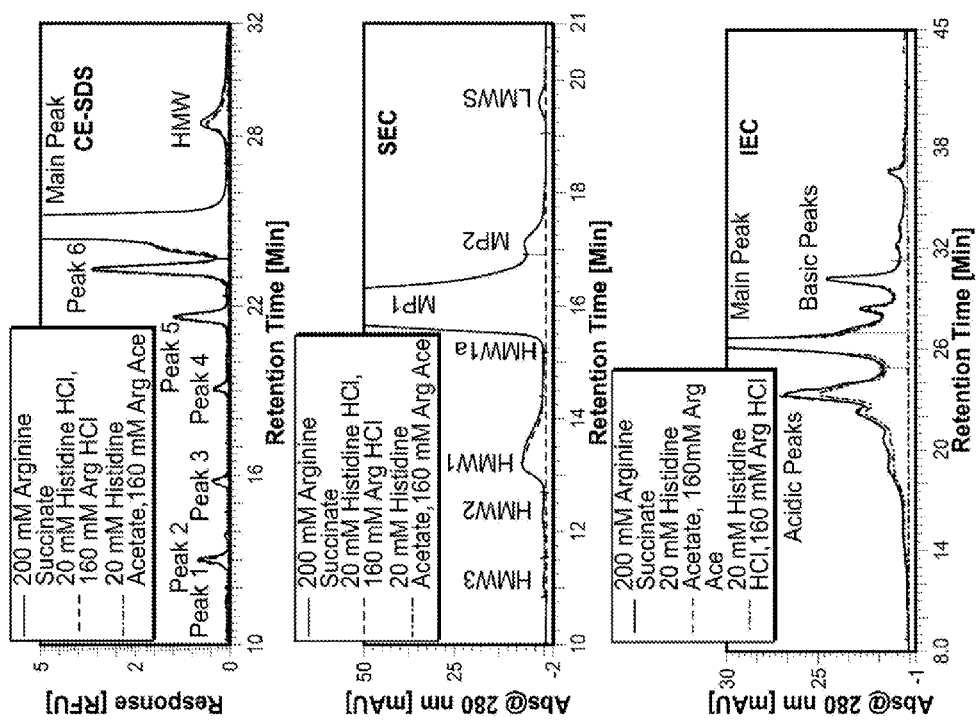
FIG. 26 shows counter-ion effects on 200 mg/mL anti-PCSK9 at pH 6.0 by CE-SDS (top), SEC (middle), and IEC (bottom) after 1 month at 40° C. storage.

The effect of buffer species on accelerated stability of 200 mg/mL anti-PCSK9 at pH 6.0 was evaluated in formulations containing the following three buffer systems: (1) 160 mM arginine succinate, (2) 20 mM histidine HCl and 160 mM arginine HCl, and (3) 20 mM histidine acetate and 160 mM arginine acetate. All three formulations contained 0.02% PS20. After 1 month at 40° C., anti-PCSK9 had comparable CE-SDS profiles among the three buffer systems (FIG. 26, top panel). No differences were observed by SEC between histidine HCl/arginine HCl and histidine acetate/arginine acetate buffer systems, while the use of the arginine succinate buffer had a slight increase in a HMWS Peak (FIG. 26, middle panel). By IEC analysis, the use of histidine HCl/arginine HCl buffer system in the formulation had less acidic peak formation when compared to histidine acetate/arginine acetate buffer system and arginine succinate buffer (FIG. 26, bottom panel). However, the overall degradation rates of anti-PCSK9 at 40° C. determined by SEC, IEC and CE-SDS are comparable in all three buffer systems at pH 6.0 (Table 9).

TABLE 9

Degradation Rate for 200 mg/mL anti-PCK9 at 40° C. in Various Formulations.

| | % Loss/Month at 40° C. | | | | | | |
|---|---|---|---|---|---|---|---|
| | 200 mM Arginine Succinate | | | 20 mM HisHCl, 160 mM ArgHCl | | 20 mM HisAce, 160 mM ArgAce | |
| | pH 5.0 | pH 5.5 | pH 6.0 | pH 6.0 | pH 6.5 | pH 5.5 | pH 6.0 |
| SEC Main Peak | 3.8 | 2.7 | 2.2 | 2.1 | 2.9 | 2.1 | 2.1 |
| IEC Main Peak | 33 | 22 | 19 | 15.9 | 18 | 20.9 | 19 |
| CE-SDS Main Peak | 5.1 | 4.5 | 3.6 | 3.8 | 3.5 | 4.0 | 4.3 |

The stability of anti-PCSK9 in two formulations (histidine HCl, pH 6.0 and histidine acetate, pH 6.0) in a 1 mL syringe was also evaluated.

At 5° C., both formulations were stable for up to 6 months (Tables 10 and 11). At accelerated and stress conditions, formation of acidic variants and aggregation are the major degradation routes for anti-PCSK9 in liquid formulation. At 30° C./65% relative humidity (RH) and 40° C./75% RH, the protein degraded faster in histidine acetate than histidine HCl at pH 6.0 as determined by IEC (Table 11). No differences in aggregation rate were observed by SEC and CE-SDS for either formulation under the same storage conditions (Table 12). No increase in oxidation was observed for both lead formulations when stored at 5° C. for up to 6 months. Although there was a slight increase in oxidation of Met256 (~2%) in the Fc portion in both formulations after 6 months at 30° C./65% RH, increase in oxidation of other Met and Trp residues was not observed. Loss of potency was not observed in either formulation for up to 6 months at 5° C. and 30° C./65% RH. Similar results were obtained using a 2.25 mL syringe.

TABLE 10

Stability Data for 200 mg/mL anti-PCSK9 in 20 mM Histidine HCl, 160 mM Arginine HCl, 0.02% PS20, pH 6.0 in a 1-mL Syringe.

| | | | | IEC | | | SEC | | | | Potency % |
|---|---|---|---|---|---|---|---|---|---|---|---|
| Temp ° C./% RH | Timepoint Days/Months | Strength mg/mL | % Acidic | % Main Peak | % Basic | % HMWS | % Main Peak | % LMWS | | CE-SDS % Main Peak | Relative Potency |
| NA | T = 0/0 | 209 | 11.6 | 73.1 | 15.1 | 0.7 | 99.2 | 0 | | 96.1 | 114 |
| 5 | 28/1 | 210 | 11.9 | 73.5 | 14.5 | 0.6 | 99.3 | 0 | | 96.2 | 101 |
| 5 | 61/2 | 206 | 11.7 | 72.9 | 15.3 | 0.6 | 99.3 | 0 | | 96.0 | 100 |
| 5 | 91/3 | 208 | 11.6 | 73.3 | 15.0 | 0.6 | 99.3 | 0 | | 96.0 | 101 |
| 5 | 183/6 | 208 | 12.4 | 71.9 | 15.6 | 0.7 | 99.2 | 0 | | 95.3 | 103 |
| 30/65 | 28/1 | 210 | 15.0 | 69.5 | 15.3 | 0.7 | 99.1 | 0.1 | | 95.6 | NT |
| 30/65 | 61/2 | 206 | 19.0 | 64.0 | 16.9 | 0.9 | 98.8 | 0.2 | | 94.7 | 91 |
| 30/65 | 91/3 | 204 | 21.4 | 61.9 | 16.5 | 1.0 | 98.5 | 0.4 | | 94.0 | 84 |
| 30/65 | 183/6 | 209 | 33.9 | 48.7 | 17.3 | 1.4 | 97.7 | 0.8 | | 91.2 | 92 |
| 40/75 | 7/0.25 | 206 | 15.0 | 68.6 | 16.3 | 0.8 | 99.0 | 0.1 | | 95.5 | NT |
| 40/75 | 14/0.5 | 206 | 18.9 | 64.3 | 16.7 | 0.9 | 98.8 | 0.2 | | 95.0 | NT |
| 40/75 | 28/1 | 209 | 25.9 | 57.4 | 16.6 | 1.1 | 98.4 | 0.4 | | 93.6 | 105 |

NT = not tested.

TABLE 11

Stability Data for 200 mg/mL anti-PCSK9 in 20 mM Histidine Acetate, 160 mM Arginine Acetate, 0.02% PS20, pH 6.0 in a 1-mL syringe.

| | | | | IEC | | | SEC | | | |
|---|---|---|---|---|---|---|---|---|---|---|
| Temp (° C.) | Timepoint Days/Months | Strength mg/mL | % Acidic | % Main Peak | % Basic | % HMWS | % Main Peak | % LMWS | % Main Peak | % Relative Potency |
| NA | T = 0/0 | 211 | 11.8 | 72.7 | 15.4 | 0.6 | 99.3 | 0 | 96.2 | 100 |
| 5 | 28/1 | 203 | 12.1 | 72.8 | 14.9 | 0.6 | 99.4 | 0 | 96.2 | 106 |

TABLE 11-continued

Stability Data for 200 mg/mL anti-PCSK9 in 20 mM Histidine Acetate,
160 mM Arginine Acetate, 0.02% PS20, pH 6.0 in a 1-mL syringe.

| Temp (° C.) | Timepoint Days/Months | Strength mg/mL | IEC | | | SEC | | | | % Relative Potency |
|---|---|---|---|---|---|---|---|---|---|---|
| | | | % Acidic | % Main Peak | % Basic | % HMWS | % Main Peak | % LMWS | % Main Peak | |
| 5 | 61/2 | 208 | 11.7 | 72.8 | 15.4 | 0.6 | 99.3 | 0 | 96.0 | 97 |
| 5 | 91/3 | 208 | 11.6 | 72.9 | 15.3 | 0.6 | 99.3 | 0 | 96.0 | 92 |
| 5 | 183/6 | 207 | 12.5 | 71.6 | 15.8 | 0.7 | 99.2 | 0 | 95.6 | 98 |
| 30/65 | 28/1 | 209 | 16.8 | 67.5 | 15.6 | 0.7 | 99.1 | 0.1 | 95.6 | NT |
| 30/65 | 61/2 | 210 | 21.6 | 61.8 | 16.4 | 0.9 | 98.8 | 0.2 | 94.7 | 98 |
| 30/65 | 91/3 | 205 | 26.1 | 57.4 | 16.3 | 1.0 | 98.6 | 0.3 | 94.3 | 87 |
| 30/65 | 183/6 | 205 | 41.4 | 42.5 | 16.0 | 1.5 | 97.6 | 0.8 | 91.1 | 91 |
| 40/75 | 7/0.25 | 206 | 17.0 | 66.6 | 16.2 | 0.8 | 99.0 | 0.1 | 95.4 | NT |
| 40/75 | 14/0.5 | 204 | 22.5 | 60.0 | 16.2 | 0.9 | 98.8 | 0.2 | 94.5 | NT |
| 40/75 | 28/1 | 196 | 31.8 | 51.9 | 16.1 | 1.1 | 98.4 | 0.4 | 93.5 | 106 |

NT = not tested.

TABLE 12

Degradation Rates for anti-PCSK9 in a 1-mL Syringe at Accelerated Stability Conditions.

| % Change Per Month | | Histidine HCl[1] | Histidine Acetate[2] |
|---|---|---|---|
| IEC | 30° C./65% RH | 4.0 | 5.0 |
| | 40° C./75% RH | 16.7 | 22.0 |
| SEC | 30° C./65% RH | 0.2 | 0.2 |
| | 40° C./75% RH | 0.8 | 0.9 |
| CE-SDS | 30° C./65% RH | 0.8 | 0.8 |
| | 40° C./75% RH | 2.6 | 2.8 |

[1]Histidine HCl = 200 mg/mL anti-PCSK9 in 20 mM histidine HCl, 160 mM arginine HCl, 0.02% PS20, pH 6.0
[2]Histidine Acetate = 200 mg/mL anti-PCSK9 in 20 mM histidine acetate, 160 mM arginine acetate, 0.02% PS20, pH 6.0

Frozen Stability

Anti-PCSK9 was formulated at 200 mg/mL in the following two formulations: (1) 20 mM histidine HCl, 160 mM arginine HCl, 0.02% PS20, pH 6.0; and (2) 20 mM histidine acetate, 160 mM arginine acetate, 0.02% PS20, pH 6.0. For each formulation, 20 mL of the drug solution was filled into 25-cc 316L stainless steel minicans. All minicans were then placed at −20° C. for up to 6 months for stability analysis.

Figure 25:
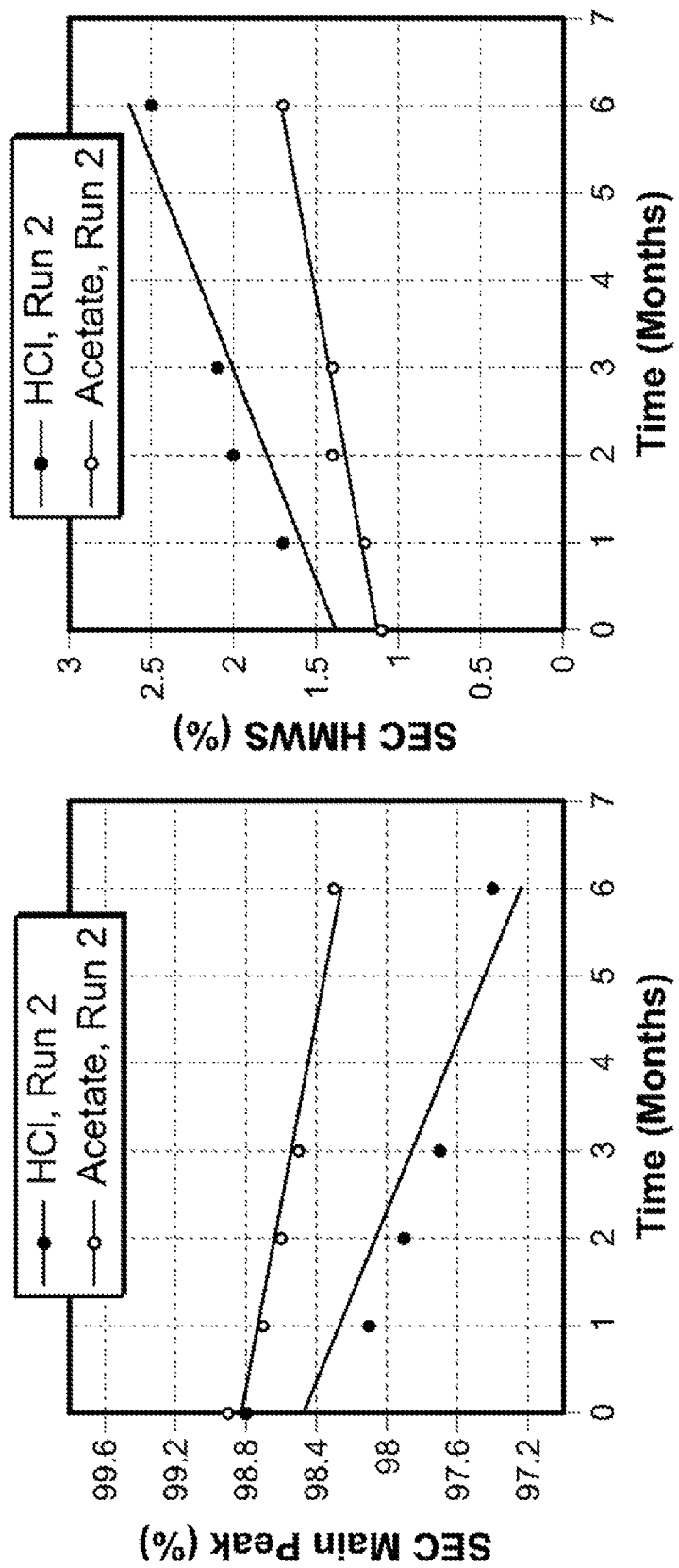
FIG. 25 shows percent main peak (left panel) and percent high molecular weight species (HMWS) (right panel) data by SEC for anti-PCSK9 during frozen storage in HCl (200 mg/mL anti-PCSK9 in 20 mM histidine HCl, 160 mM arginine HCl, 0.02% PS20, pH 6.0) and Acetate (200 mg/mL anti-PCSK9 in 20 mM histidine acetate, 160 mM arginine acetate, 0.02% PS20, pH 6.0) formulations.

No difference was observed by IEC, CE-SDS and potency for both formulations for up to 6 months at −20° C. However, aggregates increased by 1.4% in the histidine HCl after 6 months of frozen storage when compared to only a 0.5% increase in aggregates in the histidine acetate formulations under the same storage condition (see FIG. 25). Due to the faster rate of aggregation with the histidine HCl formulation under frozen storage conditions, the histidine acetate formulation was selected as the preferred buffer.

Effect of Sucrose on Frozen Stability

Sucrose was evaluated for its effect on stabilizing anti-PCSK9 during frozen storage. Using a lab-scale Millipore Tangential Flow Filtration (TFF) system equipped with LCGC10 cartridges, anti-PCSK9 was tested in the following two sucrose-containing formulations: (1) 200 mg/mL anti-PCSK9 in 20 mM histidine HCl, 130 mM arginine HCl, 60 mM sucrose, 0.02% PS20 (w/v), pH 6.0; and (2) 200 mg/mL anti-PCSK9 in 20 mM histidine acetate, 100 mM arginine acetate, 60 mM sucrose, 0.02% PS20 (w/v), pH 6.0. Samples of anti-PCSK9 in the two formulations were placed at −20° C. for up to 3 months and analyzed by SEC for aggregation.

The addition of sucrose (60 mM) had no effect on reducing aggregation of aPCSK9 in the histidine acetate formulation, but it did help to slow down aggregation in the histidine HCl formulation by 0.7% over 3 months at −20° C. However, the addition of sucrose also increased the viscosity from 7-8 cP to 11-13 cP at 25° C. for both formulations, which was undesirable for a subcutaneous formulation. Therefore, sucrose was not selected as a stabilizer for the formulation.

Based on the results described above, a liquid formulation consisting of 200 mg/mL anti-PCSK9 in 20 mM histidine acetate, 160 mM arginine acetate, 0.02% PS20 (w/v), pH 6.0 was selected. This formulation has optimal stability at 2-8° C. and at −20° C. for storage and improved stability when compared to the initial formulation at pH 5.5.

Example 14

Human Clinical Trial in Patients with Coronary Heart Disease (CHD) or at High Risk of CHD This Example describes a phase II clinical study and FIGS. 27-37 show interim results for at least 50% of patients at 12 weeks. The study enrolled 248 patients, including 183 patients treated with study drug and 64 patients treated with placebo. One patient dropped out prior to the first treatment and 13 patients discontinued treatment prior to day 85 of the study. 234 patients completed at least 12 weeks of the study.

A ~3:1 randomized, double-blind, placebo-controlled, study of study drug (YW508.20.33b reformatted into human IgG$_1$ having a heavy chain with SEQ ID NO: 35 and a light chain with SEQ ID NO: 36) was conducted to evaluate the safety and efficacy of study drug on top of standard-of-care (SOC) statin in patients with fasting serum LDL-c (direct) levels of 90-250 mg/dL and either coronary heart disease (CHD) or a CHD risk equivalent. Additional eligibility criteria included weight≥45 kg (100 lb); body mass index of 18-37 kg/m$^2$; and age between 18 and 80. The randomization was stratified by LDL-c>120 mg/dL and diabetes status.

The eligibility criteria for this phase II clinical study defined a population of patients with high cardiovascular and CHD risk based on risk categories in the European Society of Cardiology (ESC)/European Atherosclerosis Society (EAS) and National Cholesterol Education Program Adult Treatment Panel III (NCEP ATP III) lipid-lowering guidelines. This study enrolled patients who qualified for a therapeutic target LDL-c level of 70 mg/dL according to these guidelines, but who had not come close to this goal despite stable SOC statin therapy, either because SOC is insufficient or because statins were not tolerated.

Briefly, CHD refers to a history of documented myocardial infarction, prior coronary revascularization procedure (percutaneous coronary intervention or coronary artery bypass graft), or prior coronary angiography (invasive coronary angiography or cardiac computed tomography coronary angiography) demonstrating at least one coronary atherosclerotic lesion with 50% diameter stenosis.

A patient with a CHD risk-equivalent condition had at least one of the following:
1. One or more forms of clinical atherosclerotic disease:
   a. Peripheral arterial disease (previously documented ankle/brachial blood pressure index<0.85, prior percutaneous or surgical peripheral arterial revascularization procedure, prior non-traumatic amputation of a lower extremity due to peripheral artery disease, or ≥50% diameter stenosis on prior vascular imaging),
   b. Carotid artery disease (previously documented carotid atherosclerotic lesion with ≥50% diameter stenosis on imaging or prior cutaneous or surgical carotid revascularization procedure),
   c. Prior ischemic stroke, documented by CT or MRI brain imaging, not due to embolism of cardiac origin (e.g., atrial fibrillation, valvular disease, or left ventricular mural thrombus) in the opinion of the investigator, or
   d. Abdominal aortic aneurysm with prior surgical or endovascular repair.
2. Diabetes mellitus type 2,
3. Diabetes mellitus type 1 with target organ damage (retinopathy, neuropathy, or nephropathy including microalbuminuria, as determined by the investigator),
4. Moderate to severe chronic kidney disease (manifested by an estimated glomerular filtration rate of 15-60 mL/min/1.73 $m^2$ using the Modification of Diet in Renal Disease equation consistently over at least three measurements spanning at least 3 months, including screening laboratories), or
5. Two or more of the CHD risk factors listed below AND either an absolute 10-year risk of a CHD event≥20% (as determined by the National Cholesterol Education Program Adult Treatment Panel III guideline modification of the Framingham risk score) or a 10-year risk of a first fatal atherosclerotic event≥10% (determined by the Systemic Coronary Risk Estimation system):
   a. Age≥45 years for men or ≥55 years for women,
   b. Current cigarette smoking (within 1 month),
   c. Hypertension (screening systolic blood pressure≥140 mmHg, diastolic blood pressure≥90 mmHg, or taking an antihypertensive medication to treat hypertension)
   d. Low HDL cholesterol (<40 mg/dL), or
   e. Family history of premature CHD (myocardial infarction or coronary revascularization in a male first-degree relative<55 years of age or in a female first-degree relative<65 years of age).

Diabetes status was determined based on the presence of any one of the following, according to patient medical record or history, or to screening laboratory test results: (1) $HbA_{1c}$>6.5%, (2) fasting plasma glucose≥126 mg/dL (7.0 mmol/L), (3) prior 2-hour plasma glucose≥200 mg/dL (11.1 mmol/L) during an oral glucose tolerance test (the test should be performed as described by the World Health Organization, with use of a glucose load containing the equivalent of 75 g of anhydrous glucose dissolved in water), or (4) currently on an oral or injectable therapy for a diagnosis of diabetes mellitus.

Exclusion criteria included: planned coronary, carotid or peripheral arterial revascularization procedure or surgery during study; uncontrolled clinically significant medical disease as listed in the protocol within 3 months or screening; any acquired or congenital immunosuppression; any organ transplant other than the corneal transplant; life expectancy<2 years, in the investigator's judgment; fasting serum triglyceride levels>=400 mg/dL; history of alcoholism or drug addiction with a year of screening; use of illicit drugs with 3 months of screening; pregnancy or not willing to use highly effective contraception; history of anaphylaxis or anaphylactic reactions.

248 patients (adult men and women) with serum LDL-c concentrations of 90-250 mg/dL and either CHD or a CHD risk equivalent were randomized to one of five study arms and were administered study drug or a placebo arm (Arm F). Patients in the first study arm (Arm A) were administered 400 mg of anti-PCSK9 antibody every 4 weeks; patients in the second study arm (Arm B) were administered 200 mg of anti-PCSK9 antibody every 8 weeks; patients in the third study arm (Arm C) were administered 400 mg of anti-PCSK9 antibody every 8 weeks; patients in the fourth study arm (Arm D) were administered 800 mg of anti-PCSK9 antibody every 8 weeks; and patients in the fifth study arm (Arm E) were administered 800 mg of anti-PCSK9 antibody every 12 weeks. An overview of study dose cohorts, study drug dose regimen, and number of patients per arm are provided in FIG. 27. All doses were administered subcutaneously using syringes. The drug product is formulated as 150 mg/mL antibody in 200 mM arginine succinate, 0.02% polysorbate 20, pH 5.5.

The demographics of the patients in the study are set forth below in Table 13, indicating no difference by arm. The patients' baseline characteristics are set forth below in Table 14, indicating no difference by arm.

TABLE 13

Patient Demographics
(Mean (SD), unless noted)

| | 400 mg/4 W (n = 57) | 200 mg/8 W (n = 23) | 400 mg/8 W (n = 30) | 800 mg/8 W (n = 50) | 800 mg/12 W (n = 23) | Placebo (n = 64) | mITT (n = 247) |
|---|---|---|---|---|---|---|---|
| Age (years) | 66 (8.5) | 63 (10.0) | 63 (8.1) | 64 (8.9) | 64 (7.2) | 63 (7.8) | 64 (8.4) |
| Weight (kg) | 89 (15.4) | 89 (15.3) | 85 (11.7) | 83 (17.7) | 83 (17.1) | 87 (15.1) | 86 (15.6) |
| BMI (kg/m) | 31 (4.3) | 30 (4.5) | 30 (4.2) | 29 (5.2) | 29 (3.7) | 30 (5.0) | 30 (4.7) |
| Female (%) | 24 (42%) | 8 (35%) | 16 (53%) | 24 (48%) | 10 (44%) | 24 (38%) | 106 (43%) |
| Hispanic (%) | 1 (2%) | 1 (4%) | 1 (3%) | 1 (2%) | 1 (4%) | 5 (8%) | 10 (4%) |
| Race: White (%) | 55 (97%) | 19 (83%) | 27 (90%) | 44 (88%) | 23 (100%) | 59 (92%) | 227 (92%) |
| Race: Black (%) | 1 (2%) | 2 (9%) | 2 (7%) | 5 (10%) | 0 | 3 (5%) | 13 (5%) |
| Race: Asian (%) | 0 | 0 | 1 (3%) | 1 (2%) | 0 | 1 (2%) | 3 (1%) |
| Race: Other (%) | 1 (2%) | 1 (4%) | 0 | 0 | 0 | 1 (2%) | 3 (1%) |
| Race: Native (%) | 0 | 1 (4%) | 0 | 0 | 0 | 0 | 1 (0.4%) |

TABLE 14

Patient Baseline Characteristics
(Mean (SD), unless noted)

|  | 400 mg/4 W (n = 57) | 200 mg/8 W (n = 23) | 400 mg/8 W (n = 30) | 800 mg/8 W (n = 50) | 800 mg/12 W (n = 23) | Placebo (n = 64) | mITT (n = 247) |
|---|---|---|---|---|---|---|---|
| Pre-diabetic (% FBG ≥ 100 mg/dl) | 68% | 65% | 60% | 54% | 65% | 59% | 62% |
| Statin use (%) | 88% | 78% | 73% | 76% | 74% | 89% | 82% |
| LDL-c ≥ 120 (%) | 46% | 48% | 60% | 54% | 52% | 45% | 50% |
| LDL-c (mg/dL) | 123 (31.3) | 123 (25.3) | 133 (35.2) | 127 (31.5) | 134 (43.8) | 122 (31.4) | 126 (32.7) |
| Median LDL-c (mg/dL) | 117 | 117 | 123 | 118 | 123 | 111 | 117 |
| Triglyceride (mg/dL) | 156 (66.3) | 146 (60.0) | 152 (54.3) | 173 (90.8) | 144 (37.0) | 141 (63.1) | 153 (67.8) |
| Median Trig. (mg/dL) | 142 | 132 | 142 | 149 | 145 | 132 | 142 |
| Family history of CHD (% yes) | 26 (46%) | 5 (22%) | 13 (43%) | 20 (40%) | 9 (39%) | 18 (28%) | 91 (37%) |
| Smoker: never (%) | 23 (40%) | 6 (26%) | 13 (43%) | 17 (34%) | 7 (30%) | 25 (39%) | 91 (37%) |

Figure 27:
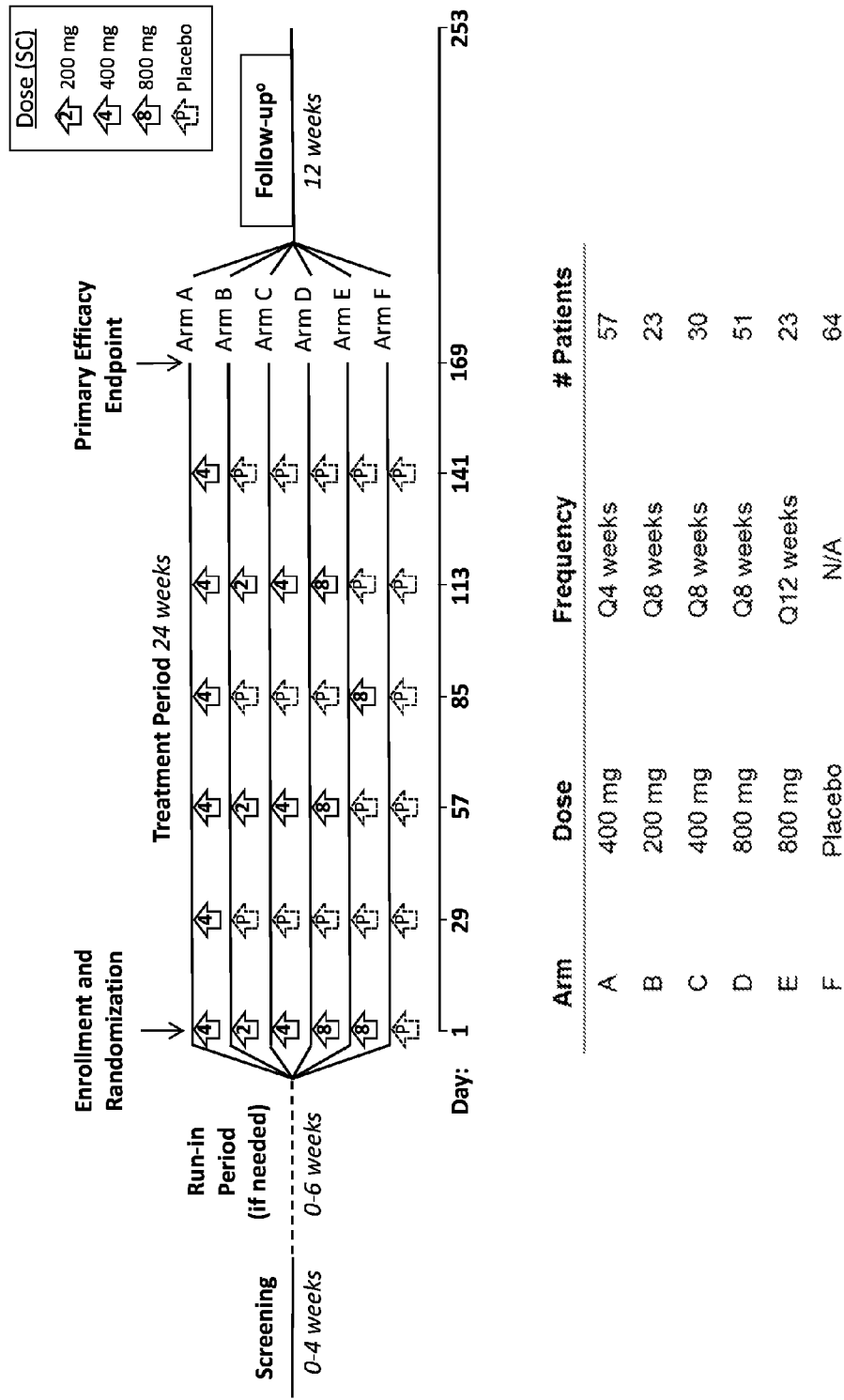
FIG. 27 shows the study design of a phase II clinical trial, including an overview of study dose cohorts, anti-PCSK9 antibody dose regimen, and number of patients in each arm of the trial.

As shown in FIG. 27, the study includes consecutive periods for screening (0-4 weeks), run-in (0-6 weeks, if necessary), treatment (24 weeks; Days 1-169), and follow-up (12 weeks). The study completion visit at the end of the follow-up period (Day 253) occurs 16 weeks after the final dose of study drug (Day 141). All patients, regardless of treatment assignment, received standard-of-care (SOC) treatment, including statins unless statins were not tolerated. SOC statin therapy refers to a therapy meeting one of the following conditions: (1) high-dose simvastatin (40 mg daily), atorvastatin (40-80 mg daily), or rosuvastatin (20-40 mg daily), (2) low-dose simvastatin, atorvastatin, or rosuvastatin and documented intolerance of a high dose of that statin or of any dose of another statin, (3) other statin (any dose) and documented intolerance of simvastatin, atorvastatin, or rosuvastatin (any dose), or (4) no statin and documented intolerance of at least two statins (any statin, any dose). All patients continue SOC statin therapy throughout the treatment and follow-up periods, at the same dose they were receiving during the run-in period and at enrollment. Other prescription and over-the-counter (OTC) lipid-modifying therapies (e.g., red yeast rice, omega-3 fatty acid supplements, etc.) are not permitted. Patients who had been taking a stable dose of SOC statin therapy (or no statin and had documented intolerance to two or more statins) and no other lipid-modifying therapy for at least 4 weeks (or 6 weeks in the case of fibrates) at the time of screening did not require a run-in period.

All doses of active drug or placebo are given according to the study drug administration schedule, that is, on Days 1, 29 (±2 days), 57 (±2 days), 85(±2 days), 113 (±4 days), and 141 (±4 days) only. See FIG. 28. Patients are monitored to determine efficacy based on absolute change from baseline in LDL-c concentration at day 169. In addition, patients are monitored to determine secondary efficacy outcomes including absolute change from baseline in LDL-c concentration for each arm at the nadir for that arm; average value over time of the change in LDL-c (absolute and percent change) for each arm, up to Day 169, weighted by the number of weeks between consecutive LDL-c measurements; percent change from baseline in LDL-c concentration at Day 169 and at the nadir for each arm; percent and absolute change from baseline in LDL-c concentration at all other designated timepoints; and percent and absolute change from baseline in total cholesterol, non-HDL-c, and apolipoprotein B at Day 169 and at the nadir for each arm.

The primary efficacy outcome measure includes the change from baseline in LDL-c at Day 169. Baseline LDL-c is defined as the average of the last two measurements collected before the first dose of study drug. The treatment comparisons between the study drug doses and between each of the study drug doses and placebo were based on an analysis of covariance (ANCOVA), which was performed through a linear regression model adjusting for two covariates: baseline LDL-c concentration (<120 mg/dL, ≥120 mg/dL) and diabetes status (yes, no). The confidence intervals, as well as the least-square estimates from the ANCOVA models, were used to aid in the interpretation of the study results. The secondary efficacy outcome measures include absolute change in LDL-c at nadir and all time points; weighted average of change in LDLc per week; percent change from baseline in LDL-c at Day 169, nadir and all visits; absolute and percent change in total cholesterol, non-HDL-c, and apolipoprotein B at Day 169 and at the nadir.

Table 15 below shows patient disposition after 12 weeks of treatment.

TABLE 15

Disposition after 12 weeks of treatment.

|  | 400 mg/4 W (n = 57) | 200 mg/8 W (n = 23) | 400 mg/8 W (n = 30) | 800 mg/8 W (n = 51) | 800 mg/12 W (n = 23) | Placebo (n = 64) | ITT* (n = 248) |
|---|---|---|---|---|---|---|---|
| Completed study | 0 | 0 | 0 | 0 | 0 | 0 | 0 |
| Discontinued study | 2 (4%) | 0 | 1 (3%) | 3 (6%) | 0 | 1 (2%) | 7 (3%) |
| Discontinued drug | 3 (5%) | 0 | 1 (3%) | 4 (8%) | 0 | 2 (3%) | 10 (4.0%) |
| Adverse event | 1 (2%) | 0 | 0 | 0 | 0 | 0 | 1 (0.4%) |
| Protocol violation | 2 (4%) | 0 | 0 | 2 (4%) | 0 | 0 | 4 (1.6%) |
| Subject choice | 0 | 0 | 1 (3%) | 1 (2%) | 0 | 1 (2%) | 3 (1.2%) |
| Sponsor choice | 0 | 0 | 0 | 1 (2%) | 0 | 0 | 1 (0.4%) |
| Other | 0 | 0 | 0 | 0 | 0 | 1 (2%) | 1 (0.4%) |

Interim data of this study are summarized in Table 16 below and in FIGS. 28-36.

TABLE 16

Patients' Total Cholesterol, non-HDL-c, and Apolipoprotein B, Measured from Baseline to Nadir

|  | 400 mg/4 W (n = 57) | 200 mg/8 W (n = 23) | 400 mg/8 W (n = 30) | 800 mg/8 W (n = 50) | 800 mg/12 W (n = 23) | Placebo (n = 63) |
|---|---|---|---|---|---|---|
| TC, mean absolute change (mg/dL) | −99.9 | −73.9 | −92.3 | −102.0 | −92.3 | −24.4 |
| Reduction from placebo | 74.9 | 48.7 | 64.7 | 75.5 | 66.2 |  |
| 95% confidence interval | 65.2, 84.6 | 36.0, 61.5 | 52.9, 76.4 | 65.5, 85.5 | 53.4, 79.0 |  |
| TC, mean relative change (%) | −49.4 | −37.7 | −43.6 | −48.6 | −44.8 | −12.4 |
| Reduction from placebo | 36.7 | 25.2 | 30.8 | 35.8 | 32.1 |  |
| 95% confidence interval | 32.6, 40.8 | 19.8, 30.7 | 25.7, 35.8 | 31.6, 40.1 | 26.6, 37.6 |  |
| Non-HDLc, mean abs. ch. (mg/dL) | −101.6 | −76.2 | −96.3 | −103.3 | −95.0 | −24.1 |
| Reduction from placebo | 76.7 | 51.3 | 68.7 | 76.9 | 69.0 |  |
| 95% confidence interval | 66.9, 86.5 | 38.4, 64.1 | 56.9, 80.5 | 66.9, 87.0 | 56.1, 81.9 |  |
| Non-HDLc, mean rel. change (%) | −67.3 | −52.1 | −60.5 | −65.9 | −59.8 | −16.6 |
| Reduction from placebo | 50.3 | 35.5 | 43.7 | 49.1 | 43.0 |  |
| 95% confidence interval | 45.2, 55.4 | 28.8, 42.2 | 37.5, 49.8 | 43.9, 54.3 | 36.3, 49.7 |  |
| Apo-B, mean abs. change (mg/dL) | −64.3 | −48.5 | −59.1 | −65.6 | −62.8 | −15.8 |
| Reduction from placebo | 48.1 | 32.3 | 41.4 | 48.5 | 46.0 |  |
| 95% confidence interval | 42.0, 54.3 | 24.2, 40.4 | 33.9, 48.8 | 42.2, 54.9 | 37.8, 54.1 |  |
| Apo-B, mean relative change (%) | −63.1 | −49.2 | −55.8 | −62.7 | −58.3 | −15.7 |
| Reduction from placebo | 47.0 | 33.4 | 39.9 | 46.8 | 42.3 |  |
| 95% confidence interval | 42.2, 51.7 | 27.1, 39.6 | 34.2, 45.7 | 41.9, 51.7 | 36.1, 48.6 |  |

Figure 28:
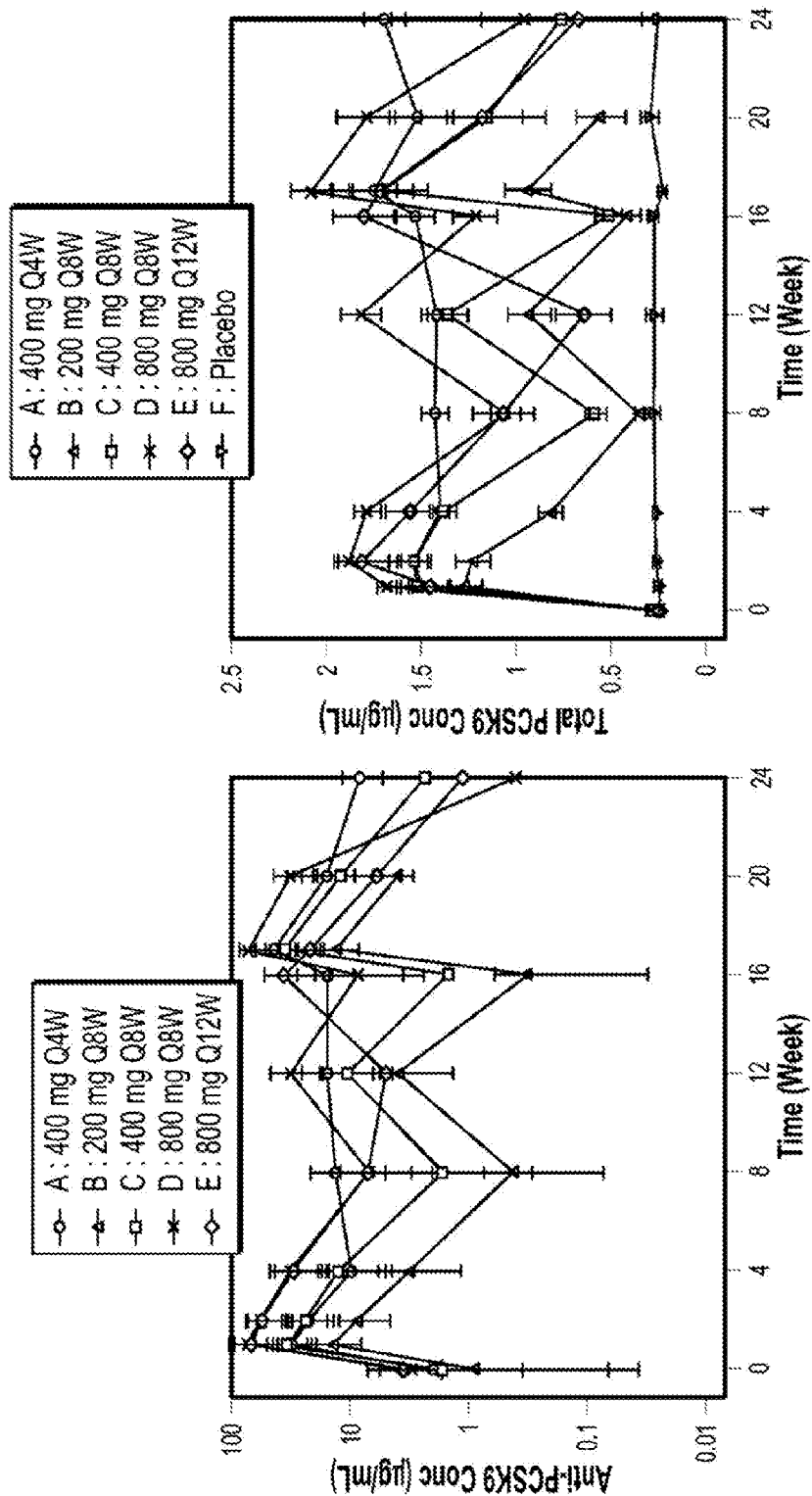
FIG. 28 shows mean pharmacokinetics (+/−standard deviation) (left panel) and mean total PCSK9 (+/−standard error) (right panel) in patients receiving anti-PCSK9 antibody or placebo.

FIG. 28 provides mean pharmacokinetics (+/−standard deviation) (left panel) and mean total PCSK9, e.g. both drug-bound and free PCSK9 (+/−standard error) (right panel).

Figure 29:
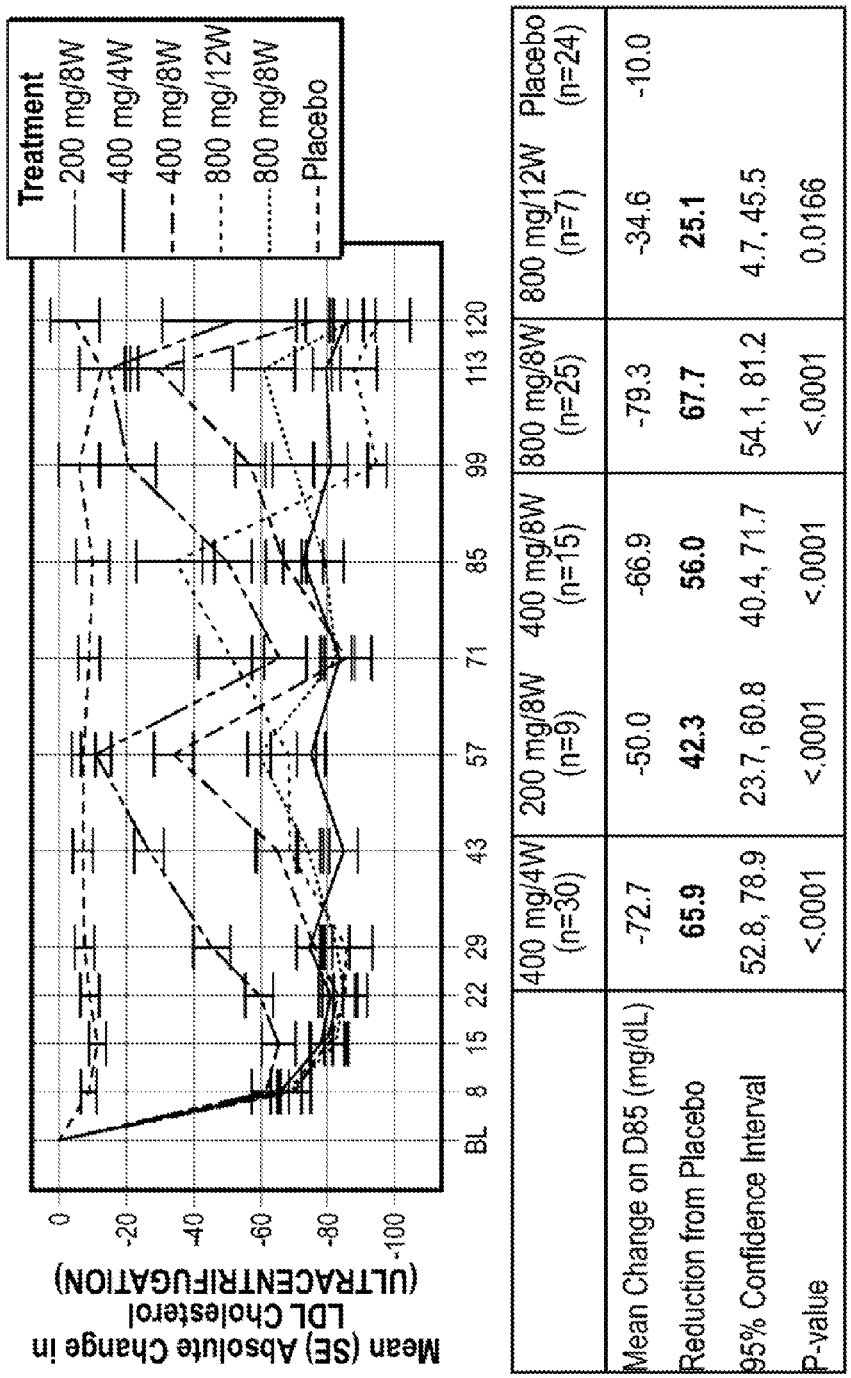
FIG. 29 shows the absolute change from baseline in direct LDL cholesterol observed in patients receiving anti-PCSK9 antibody or placebo.
Figure 30:
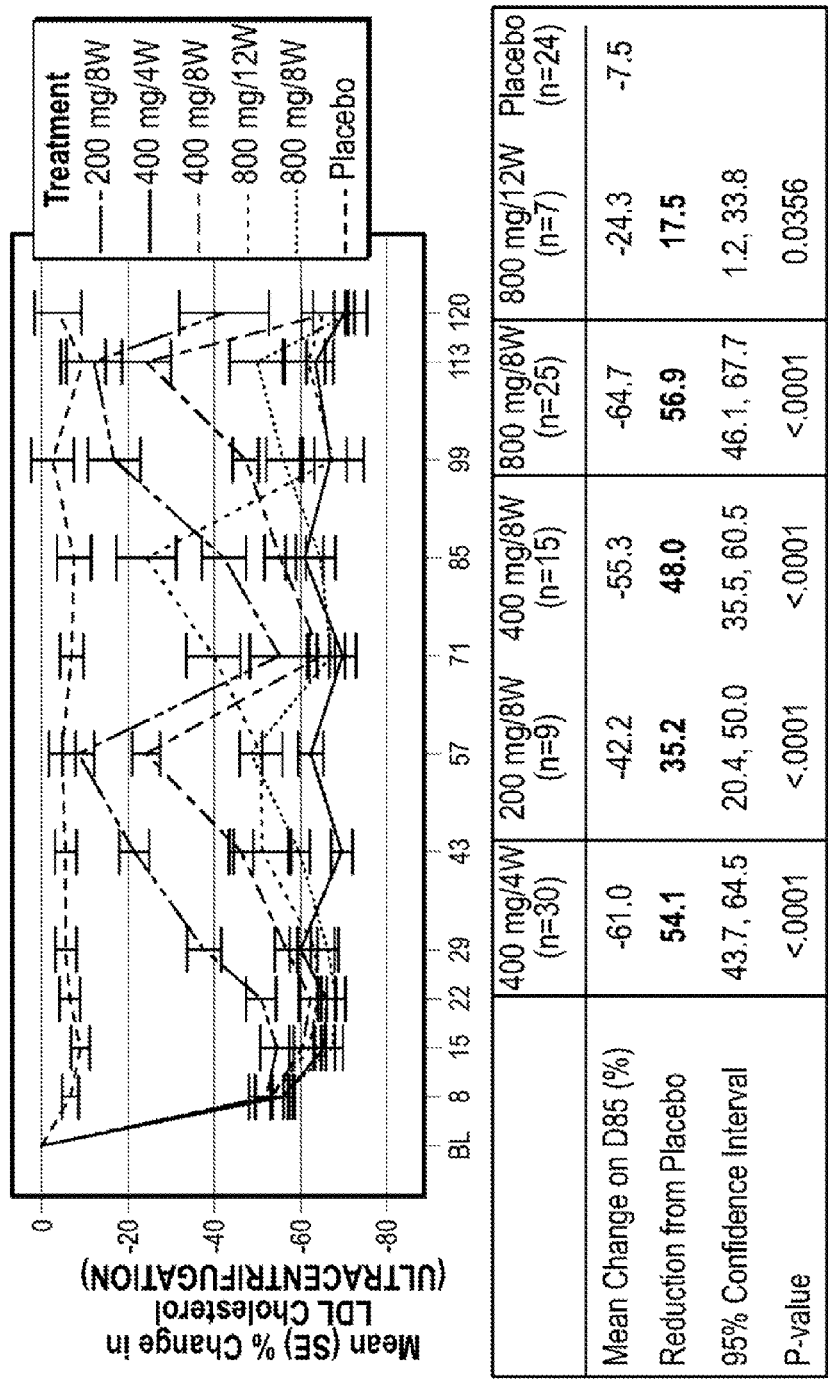
FIG. 30 shows the relative change from baseline in direct LDL cholesterol observed in patients receiving anti-PCSK9 antibody or placebo.

FIG. 29 shows the absolute change from baseline in direct LDL cholesterol observed in patients receiving anti-PCSK9 antibody or placebo. FIG. 30 shows the relative change from baseline in direct LDL cholesterol observed in patients receiving anti-PCSK9 antibody or placebo. Patients receiving 400 mg of anti-PCSK9 antibody every 4 weeks and patients receiving 800 mg of anti-PCSK9 antibody every 8 weeks exhibited the highest reduction in direct LDL-c. This effect was observed within a week of treatment. Patients receiving 800 mg of anti-PCSK9 antibody every 12 weeks exhibited the lowest reduction in direct LDL-c.

Figure 31:
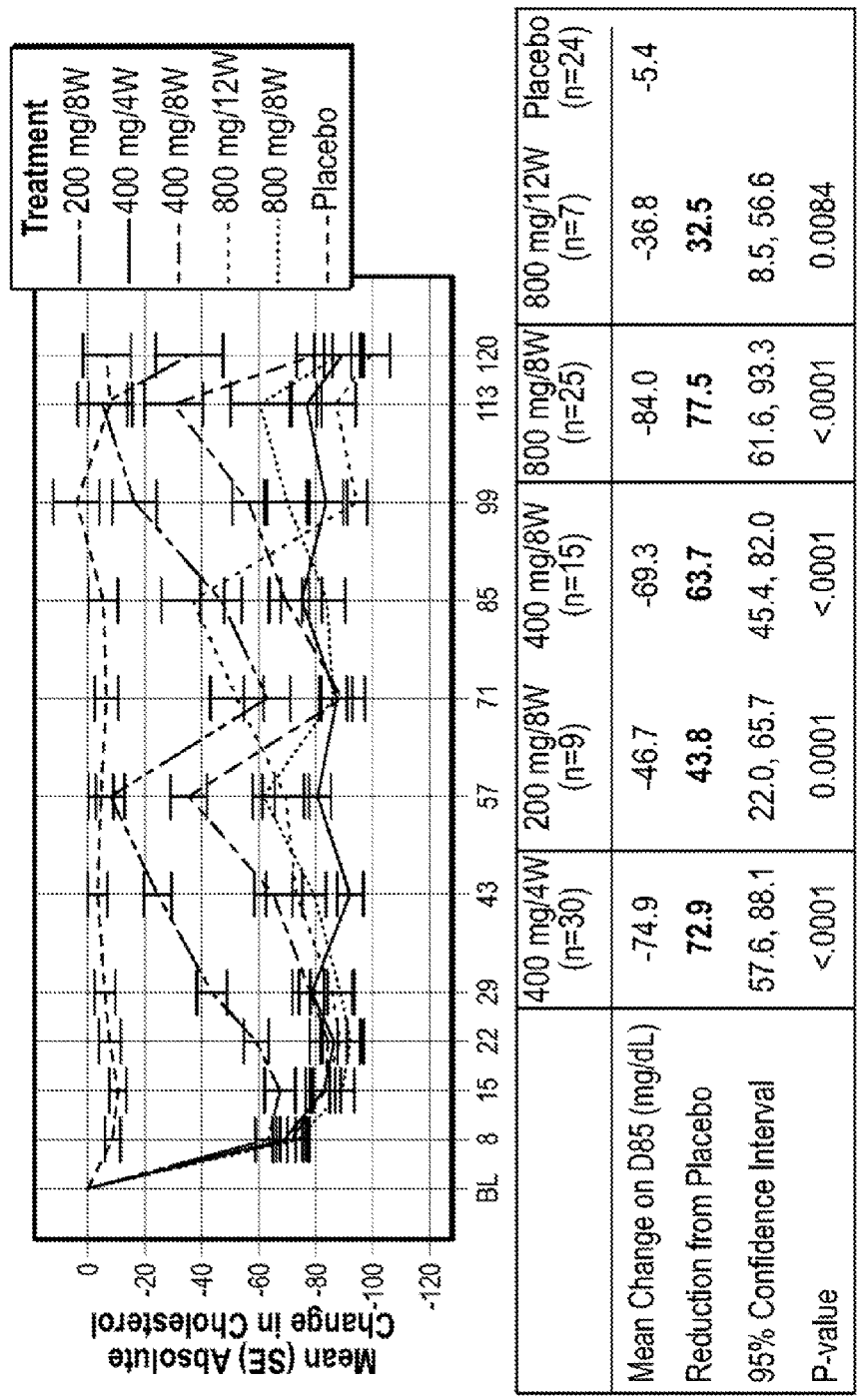
FIG. 31 shows the absolute change from baseline in total cholesterol observed in patients receiving anti-PCSK9 antibody or placebo.
Figure 32:
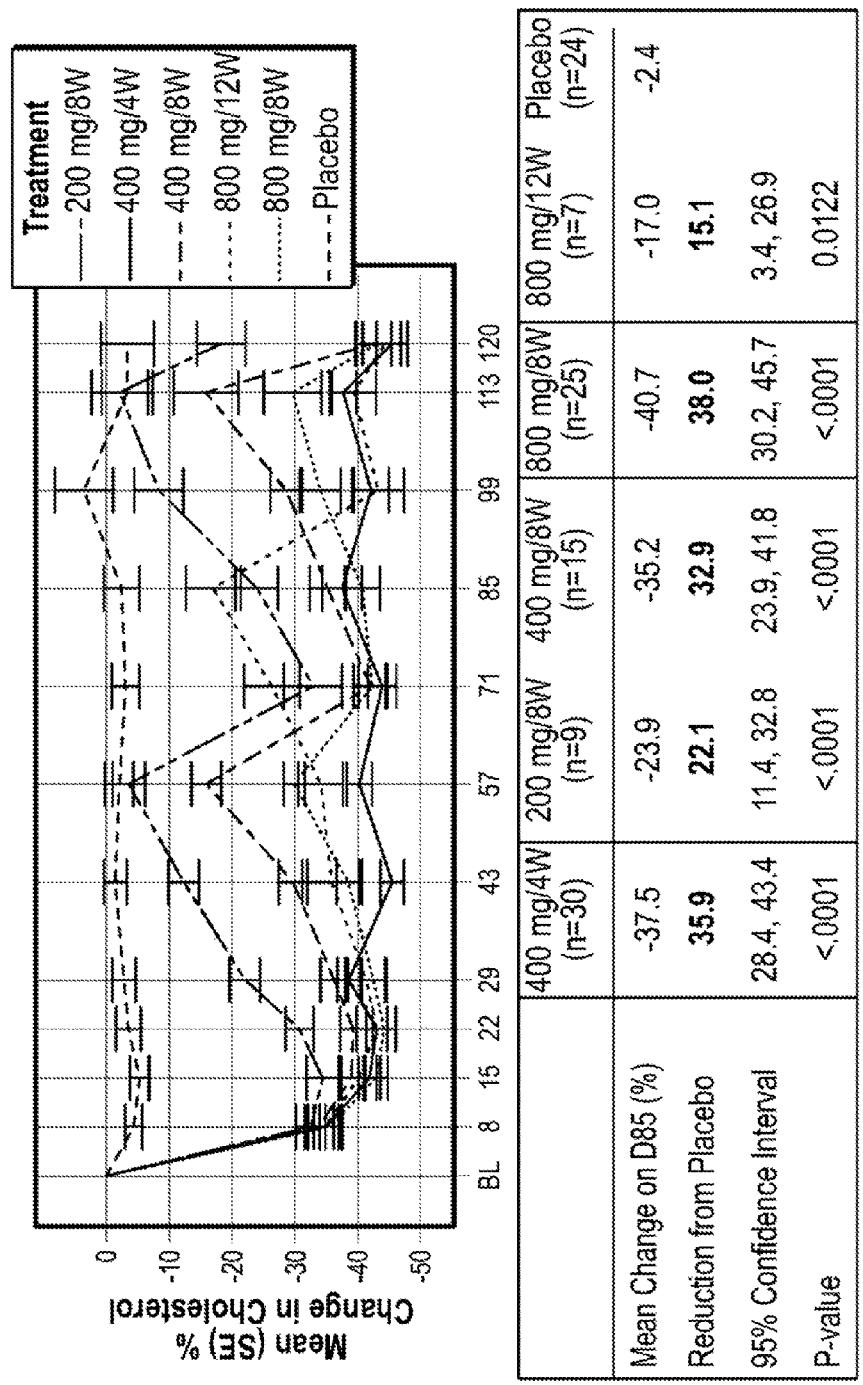
FIG. 32 shows the relative change from baseline in total cholesterol observed in patients receiving anti-PCSK9 antibody or placebo.

FIG. 31 shows the absolute change from baseline in total cholesterol observed in patients participating in this study. FIG. 32 shows the relative change from baseline in total cholesterol observed in patients receiving anti-PCSK9 antibody or placebo. Patients receiving 400 mg of anti-PCSK9 antibody every 4 weeks and patients receiving 800 mg of anti-PCSK9 antibody every 8 weeks exhibited the highest reduction in total cholesterol. This effect was observed within a week of treatment. Patients receiving 800 mg of anti-PCSK9 antibody every 12 weeks exhibited the lowest reduction in total cholesterol.

Figure 33:
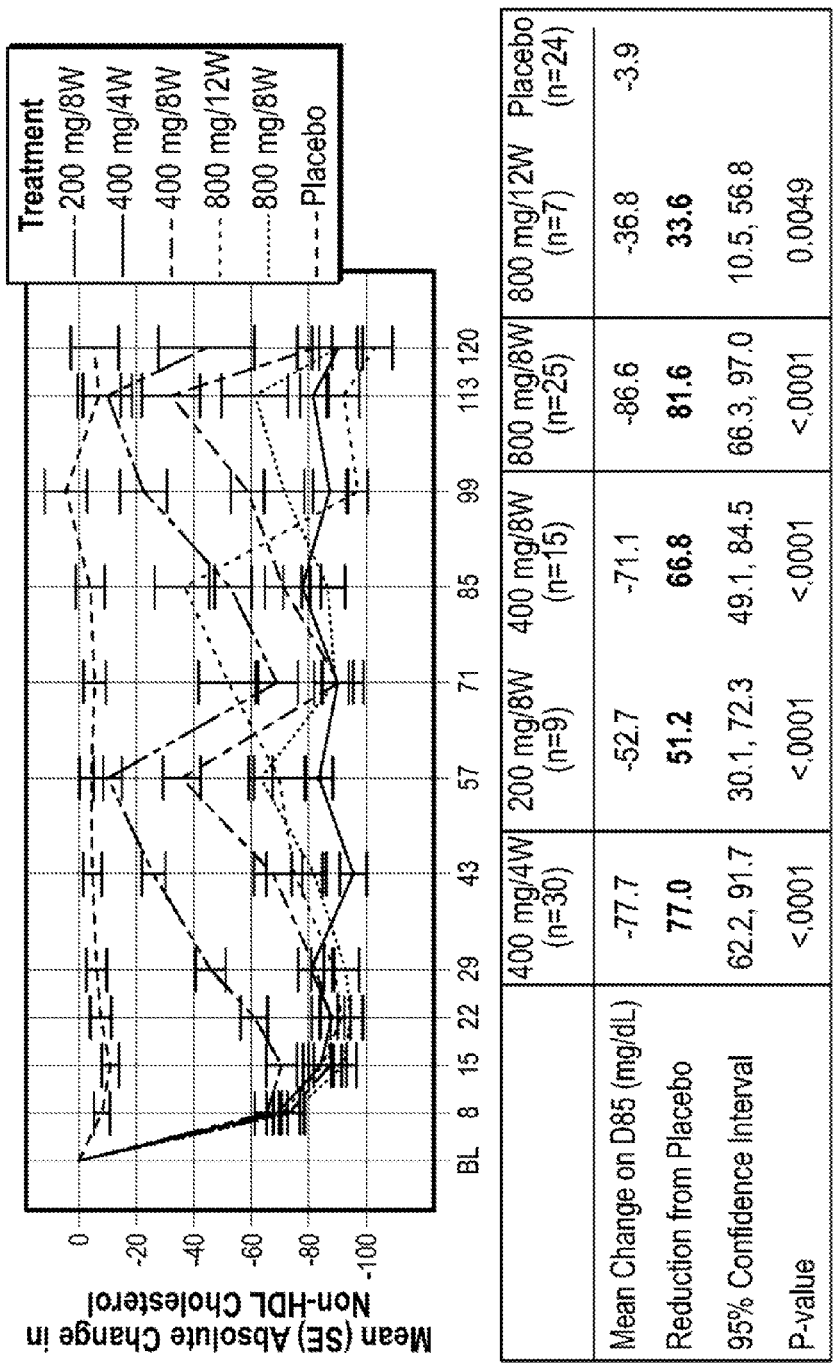
FIG. 33 shows the absolute change from baseline in non-HDL cholesterol in patients receiving anti-PCSK9 antibody or placebo.
Figure 34:
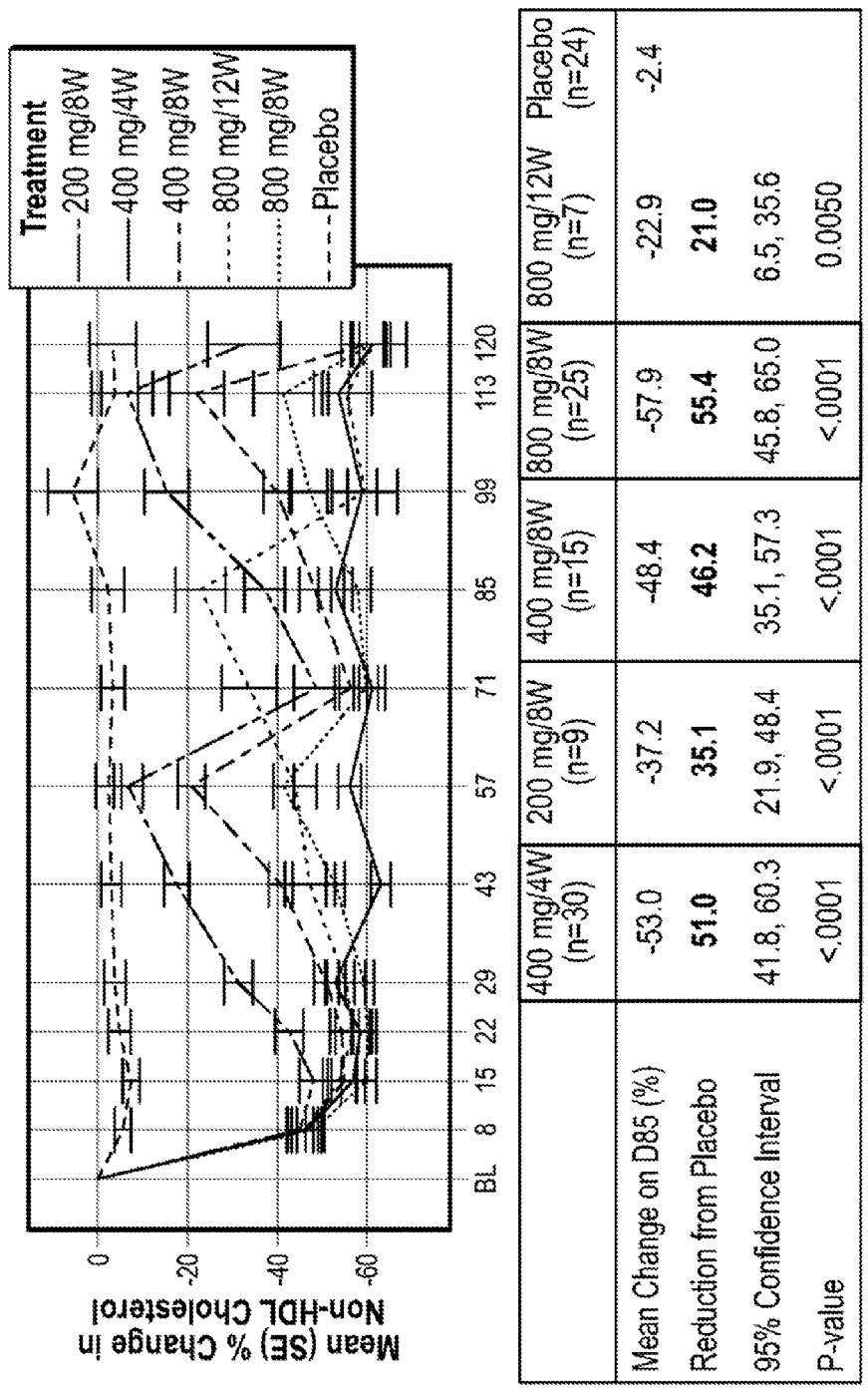
FIG. 34 shows the relative change from baseline in non-HDL cholesterol in patients receiving anti-PCSK9 antibody or placebo.

FIG. 33 shows the absolute change from baseline in non-HDL cholesterol in patients participating in this study. FIG. 34 shows the relative change from baseline in non-HDL cholesterol in patients participating in this study. Patients receiving 400 mg of anti-PCSK9 antibody every 4 weeks and patients receiving 800 mg of anti-PCSK9 antibody every 8 weeks exhibited the highest reduction in non-HDL cholesterol. This effect was observed within a week of treatment. Patients receiving 800 mg of anti-PCSK9 antibody every 12 weeks exhibited the lowest reduction in non-HDL cholesterol.

Figure 35:
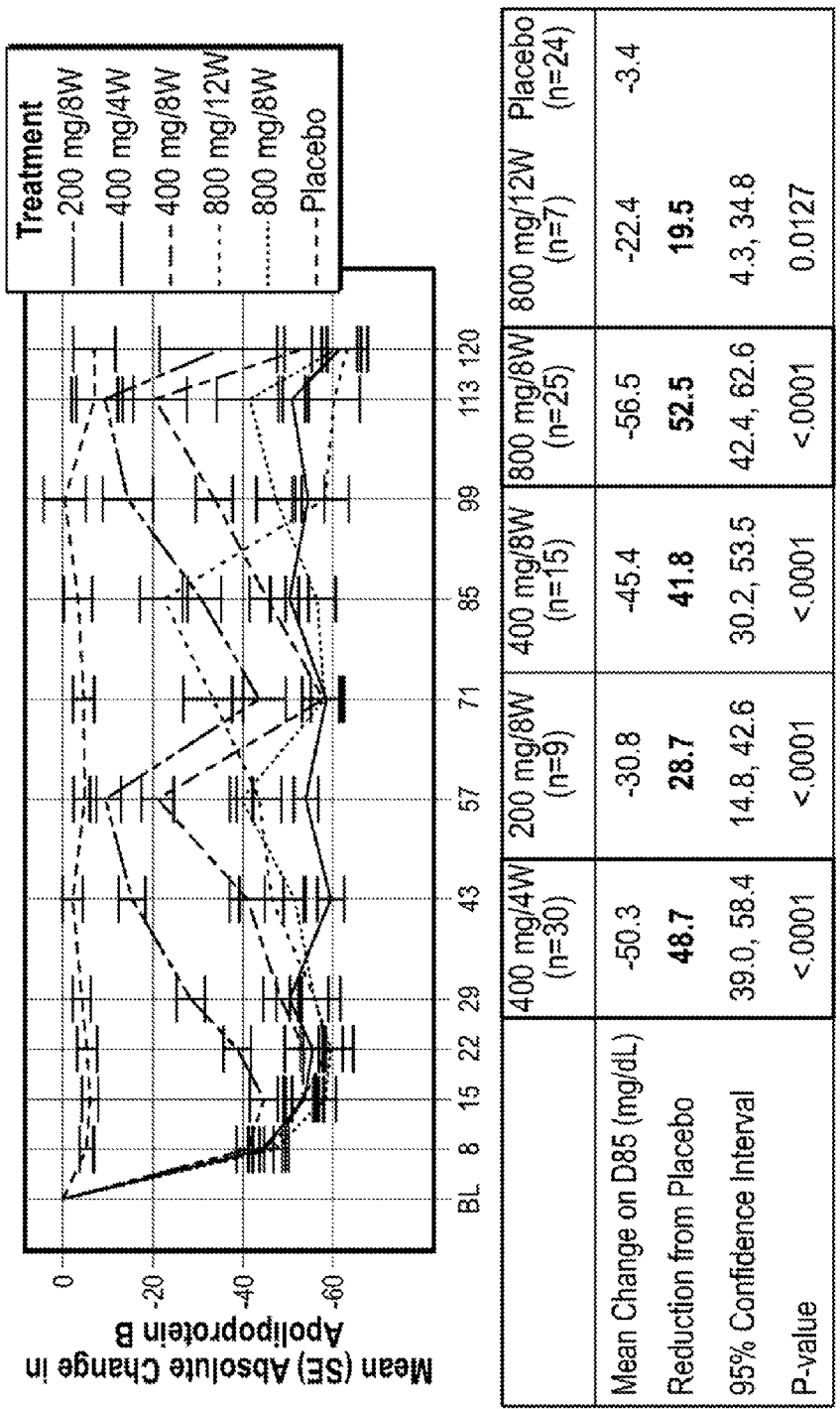
FIG. 35 shows the absolute change from baseline in apolipoprotein B in patients receiving anti-PCSK9 antibody or placebo.
Figure 36:
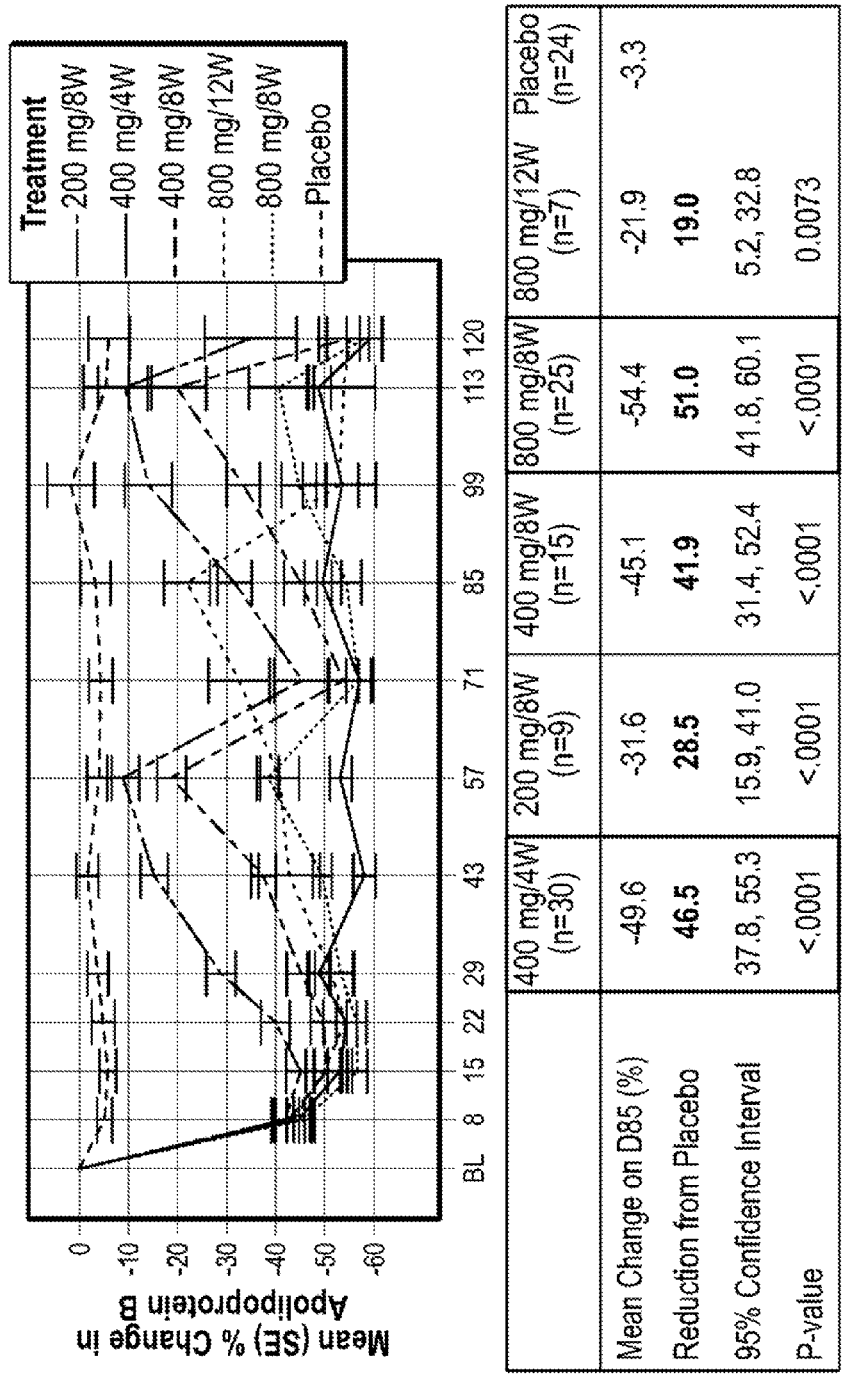
FIG. 36 shows the relative change from baseline in apolipoprotein B in patients receiving anti-PCSK9 antibody or placebo.

FIG. 35 shows the absolute change from baseline in apolipoprotein B in patients participating in this study. FIG. 36 shows the relative change from baseline in apolipoprotein B in patients participating in this study. Patients receiving 400 mg of anti-PCSK9 antibody every 4 weeks and patients receiving 800 mg of anti-PCSK9 antibody every 8 weeks exhibited the highest reduction in apolipoprotein B. This effect was observed within a week of treatment. Patients receiving 800 mg of anti-PCSK9 antibody every 12 weeks exhibited the lowest reduction in apolipoprotein B.

Conclusions regarding the efficacy of study drug are summarized here. The highest dose-dependent reduction in LDL-c on Day 85, at nadir, and AUC was observed in patients receiving 400 mg of anti-PCSK9 antibody every 4 weeks and in patients receiving 800 mg of anti-PCSK9 antibody every 8 weeks. The smallest dose-dependent reduction in LDL-c based on Day 85 analyses was observed in patients receiving 800 mg of anti-PCSK9 antibody every 12 weeks. The smallest dose-dependent reduction in LDL-c based on nadir and AUC analyses was observed in patients receiving 200 mg of anti-PCSK9 antibody every 8 weeks. The reduction was evident within a week of treatment. Dose-dependent reduction in total cholesterol, non-HDL-c, and apolipoprotein-B was observed on Day 85 and at nadir, and the reduction was also evident within a week of treatment.

Finally, patients were also monitored for safety including incidence, nature, and severity of adverse events; incidence and nature of changes in vital signs, physical findings, and clinical laboratory results during and following study drug administration; and incidence of anti-therapeutic antibodies directed against study drug.

Figures 37A, 37B:
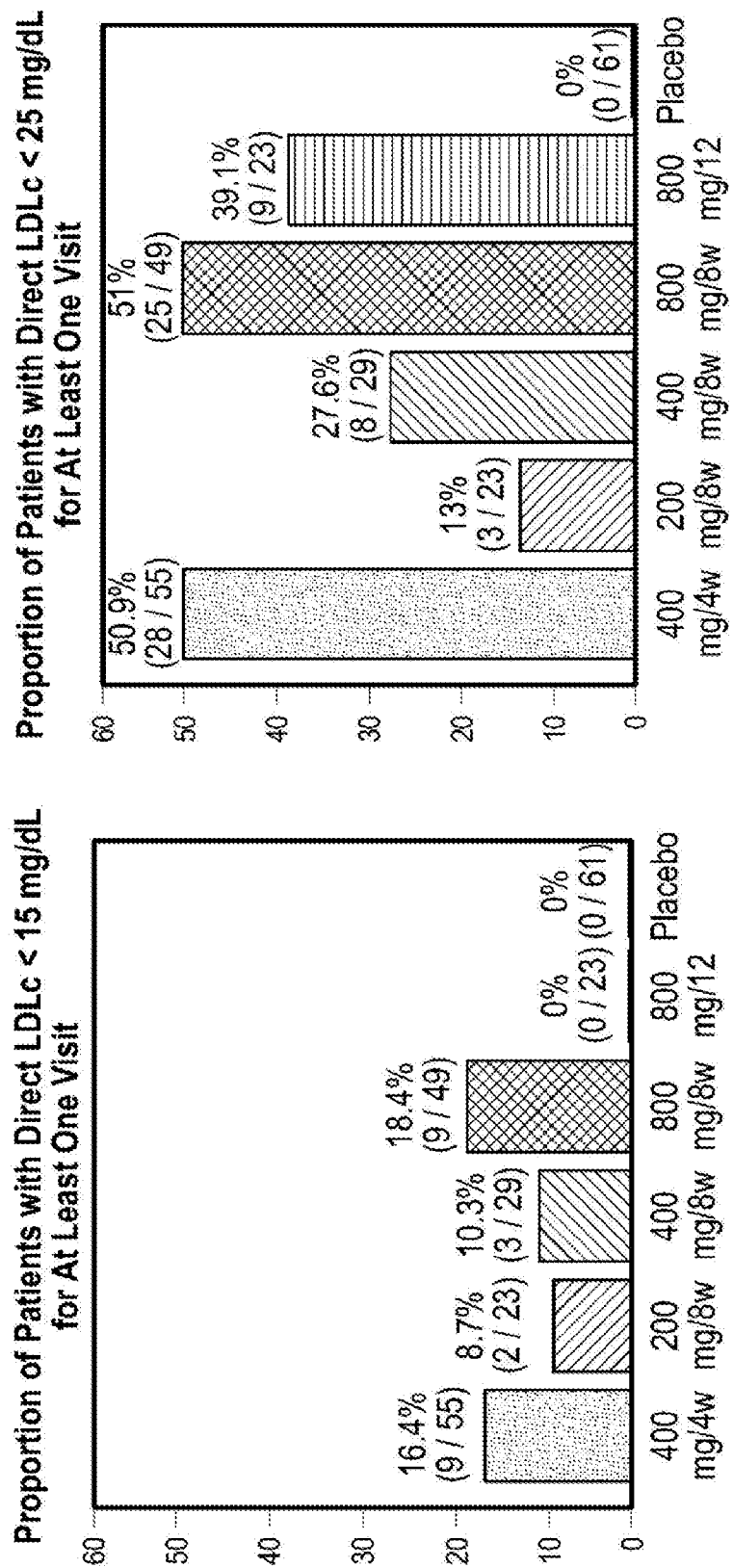
FIG. 37A shows the proportion of patients with direct LDL-c values less than or equal to 15 mg/dL for at least one visit after receiving anti-PCSK9 antibody or placebo.
FIG. 37B shows the results of experiments performed to determine the proportion of patients with direct LDL-c values less than or equal to 25 mg/dL for at least one visit after receiving anti-PCSK9 antibody or placebo.

The safety of low LDL-c values was assessed regularly in a blinded, exploratory manner. FIG. 37A shows the proportion of patients with direct LDL-c values less than or equal to 15 mg/dL for at least one visit after receiving anti-PCSK9 antibody or placebo, and FIG. 37B shows the proportion of patients with direct LDL-c values less than or equal to 25 mg/dL for at least one visit after receiving anti-PCSK9 antibody or placebo. The highest percentage of patients with LDL-c≤15 mg/dL or LDL-c≤25 mg/dL were receiving either 400 mg of drug every four weeks or 800 mg of drug every 8 weeks. The lowest percent of patients with LDL-c≤25 mg/dL were receiving 200 mg of drug every 8 weeks. Study drug was withheld from patients with two consecutive LDL-c values of <15 mg/dL. This was not considered an adverse event. Such patients were treated with placebo instead, in blinded fashion, until LDL-c increased to ≥50 mg/dL, after which these patients were switched to the lowest dosage (200 mg every 8 weeks).

Conclusions regarding the safety of study drug are summarized here. Briefly, anti-PCSK9 antibody was well tolerated in patients aged 37-80 with elevated baseline LDL-c (90-250 mg/dL), diagnosed with CHD or a CHD risk equivalent, and who were taking stable doses of statins or were statin-intolerant. Injection-site reactions were more common among patients receiving study drug (25%) vs. placebo (9%). Only 2 injection-site reactions were moderate (1 placebo, 1 study drug), and the rest were mild in severity. No other clinically significant imbalances of treatment-emergent events were observed between study drug-treated and placebo-treated patients. No clinically relevant imbalances in laboratory abnormalities were observed. No safety signals were determined. No deaths were reported, and no new safety concerns were observed. No patterns were detected in safety laboratory results.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An anti-proprotein convertase subtilisin/kexin type 9 (PCSK9) antibody comprising a heavy chain and light chain variable domain comprising six hypervariable region (HVR) sequences:
   (i) HVR-H1 comprising GFTFX$_1$X$_2$X$_3$X$_4$IH (SEQ ID NO:28), wherein X$_1$ is S or T; X$_2$ is G, R or S; X$_3$ is H, T or Y; X$_4$ is A or T;
   (ii) HVR-H2 comprising RISPANGNTNYADSVKG (SEQ ID NO:4);
   (iii) HVR-H3 comprising WIGSRELYIMDY (SEQ ID NO:5);
   (iv) HVR-L1 comprising RASQDVSX$_1$AVA (SEQ ID NO:29), wherein X$_1$ is S or T;
   (v) HVR-L2 comprising SASX$_1$LYS (SEQ ID NO:30), wherein X$_1$ is F or S; and
   (vi) HVR-L3 comprising QQAYX$_1$X$_2$X$_3$X$_4$T (SEQ ID NO:37), wherein X$_1$ is P, R or T;
   X$_2$ is A, I, S or T; X$_3$ is L, P or Q; X$_4$ is A, H, P or S.

2. The antibody of claim 1, wherein the antibody comprises (a) HVR-H1 comprising the amino acid sequence of SEQ ID NO:1, SEQ ID NO:2 or SEQ ID NO:3, (b) HVR-H2 comprising the amino acid sequence of SEQ ID NO:4, and (c) HVR-H3 comprising the amino acid sequence of SEQ ID NO:5.

3. The antibody of claim 2, further comprising (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO:33.

4. The antibody of claim 1, comprising (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO:33.

5. The antibody of claim 1, wherein the antibody comprises:
   (1) an HVR-H1 comprising the amino acid sequence of SEQ ID NO:3;
   (2) an HVR-H2 comprising the amino acid sequence of SEQ ID NO:4;
   (3) an HVR-H3 comprising the amino acid sequence of SEQ ID NO:5;
   (4) an HVR-L1 comprising the amino acid sequence of SEQ ID NO:7;
   (5) an HVR-L2 comprising the amino acid sequence of SEQ ID NO:8; and
   (6) an HVR-L3 comprising the amino acid sequence of SEQ ID NO:33.

6. The antibody of claim 1, comprising a VH sequence of SEQ ID NO:17.

7. The antibody of claim 1, comprising a VL sequence of SEQ ID NO:34.

8. The antibody of claim 1, comprising a VH sequence of SEQ ID NO:17 and a VL sequence of SEQ ID NO:34.

9. The antibody of claim 1, wherein the antibody is a monoclonal antibody.

10. The antibody of claim 1, wherein the antibody is humanized.

11. The antibody of claim 1, wherein the antibody is a human antibody.

12. The antibody of claim 1, wherein the antibody is an antibody fragment selected from a Fab, Fab'-SH, Fv, scFv or (Fab')$_2$ fragment.

13. The antibody of claim 1, wherein at least a portion of the framework sequence is a human consensus framework sequence.

14. The antibody of claim 1, comprising (i) a heavy chain comprising the amino acid sequence of SEQ ID NO:35 and a light chain comprising the amino acid sequence of SEQ ID NO:36, (ii) a heavy chain comprising amino acids 1-450 of SEQ ID NO:35 and a light chain comprising the amino acid sequence of SEQ ID NO:36, (iii) a heavy chain comprising amino acids 1-449 of SEQ ID NO:35 and a light chain comprising the amino acid sequence of SEQ ID NO:36, or (iv) the heavy and light chain of any one of (i), (ii), or (iii) wherein the proline at amino acid position 449 of SEQ ID NO:35 is amidated.

15. An anti-proprotein convertase subtilisin/kexin type 9 (PCSK9) antibody comprising (a) HVR-H3 comprising the amino acid sequence of SEQ ID NO:5, (b) HVR-L3 comprising the amino acid sequence of SEQ ID NO:33, and (c) HVR-H2 comprising the amino acid sequence of SEQ ID NO:4.

16. An anti-proprotein convertase subtilisin/kexin type 9 (PCSK9) antibody comprising a light chain variable domain comprising the amino acid sequence of SEQ ID NO:34.

17. An anti-preprotein convertase kexin type 9 (PCSK9) antibody produced by a method comprising culturing a host cell comprising a nucleic acid encoding the anti-PCSK9 antibody of claim 1 under conditions suitable for expression of the nucleic acid encoding the anti-PCSK9 antibody, and recovering the anti-PCSK9 antibody produced by the host cell.

18. A pharmaceutical composition comprising the anti-PCSK9 antibody of claim 1 and a pharmaceutically acceptable carrier.

19. A pharmaceutical composition comprising an anti-proprotein convertase subtilisin/kexin type 9 (PCSK9) antibody at 150 to 225 mg/mL, histidine acetate at 10 to 30 mM, arginine acetate at 150 to 170 mM, polysorbate at 0.01% to 0.03%, and pH at 5.8 to 6.2.

20. The composition of claim 19, wherein the anti-PCSK9 antibody comprises a variable domain comprising one, two, three, four, five, or six hypervariable region (HVR) sequences selected from the group consisting of:
  (i) HVR-H1 comprising GFTFX$_1$X$_2$X$_3$X$_4$IH (SEQ ID NO:28), wherein X$_1$ is S or T; X$_2$ is G, R or S; X$_3$ is H, T or Y; X$_4$ is A or T;
  (ii) HVR-H2 comprising RISPANGNTNYADSVKG (SEQ ID NO:4);
  (iii) HVR-H3 comprising WIGSRELYIMDY (SEQ ID NO:5);
  (iv) HVR-L1 comprising RASQDVSX$_1$AVA (SEQ ID NO:29), wherein X$_1$ is S or T;
  (v) HVR-L2 comprising SASX$_1$LYS (SEQ ID NO:30), wherein X$_1$ is F or S; and
  (vi) HVR-L3 comprising QQSYX$_1$X$_2$X$_3$X$_4$T (SEQ ID NO:31) or QQAYX$_1$X$_2$X$_3$X$_4$T (SEQ ID NO:37), wherein X$_1$ is P, R or T; X$_2$ is A, I, S or T; X$_3$ is L, P or Q; X$_4$ is A, H, P or S.

21. The composition of claim 19, wherein the anti-PCSK9 antibody or antibody fragment in the composition is at 200 mg/mL, histidine acetate in the composition is at 20 mM, arginine acetate in the composition is at 160 mM, and polysorbate 20 in the composition is 0.02%, and pH at 6.0.

22. The composition of claim 19, wherein the composition is suitable for subcutaneous administration.

23. The composition of claim 19, wherein the viscosity of the composition is less than 10 cP at 25° C.

24. The composition of claim 19, wherein the anti-PCSK9 antibody comprises a heavy chain and light chain variable domain comprising the following six hypervariable region (HVR) sequences:
  (i) HVR-H1 comprising GFTFX$_1$X$_2$X$_3$X$_4$IH (SEQ ID NO:28), wherein X$_1$ is S or T; X$_2$ is G, R or S; X$_3$ is H, T or Y; X$_4$ is A or T;
  (ii) HVR-H2 comprising RISPANGNTNYADSVKG (SEQ ID NO:4);
  (iii) HVR-H3 comprising WIGSRELYIMDY (SEQ ID NO:5);
  (iv) HVR-L1 comprising RASQDVSX$_1$AVA (SEQ ID NO:29), wherein X$_1$ is S or T;
  (v) HVR-L2 comprising SASX$_1$LYS (SEQ ID NO:30), wherein X$_1$ is F or S; and
  (vi) HVR-L3 comprising QQSYX$_1$X$_2$X$_3$X$_4$T (SEQ ID NO:31) or QQAYX1X2X3X4T (SEQ ID NO:37), wherein X$_1$ is P, R or T; X$_2$ is A, I, S or T; X$_3$ is L, P or Q; X$_4$ is A, H, P or S.

25. The composition of claim 24, wherein the antibody comprises (a) HVR-H1 comprising the amino acid sequence of SEQ ID NO:1, SEQ ID NO:2 or SEQ ID NO:3, (b) HVR-H2 comprising the amino acid sequence of SEQ ID NO:4, and (c) HVR-H3 comprising the amino acid sequence of SEQ ID NO:5.

26. The composition of claim 25, wherein the antibody further comprises (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33.

27. The composition of claim 24, wherein the antibody comprises (a) HVR-L1 comprising the amino acid sequence of SEQ ID NO:6 or SEQ ID NO:7; (b) HVR-L2 comprising the amino acid sequence of SEQ ID NO:8 or SEQ ID NO:26; and (c) HVR-L3 comprising the amino acid sequence of SEQ ID NO:9, SEQ ID NO:10, SEQ ID NO:11, SEQ ID NO:12, SEQ ID NO:13, SEQ ID NO:14, or SEQ ID NO:33.

28. The composition of claim 24, wherein the antibody comprises:
  (1) an HVR-H1 comprising the amino acid sequence of SEQ ID NO:1;
  (2) an HVR-H2 comprising the amino acid sequence of SEQ ID NO:4;
  (3) an HVR-H3 comprising the amino acid sequence of SEQ ID NO:5;
  (4) an HVR-L1 comprising the amino acid sequence of SEQ ID NO:7;
  (5) an HVR-L2 comprising the amino acid sequence of SEQ ID NO:8; and
  (6) an HVR-L3 comprising the amino acid sequence of SEQ ID NO:10.

29. The composition of claim 24, wherein the antibody comprises:
  (1) an HVR-H1 comprising the amino acid sequence of SEQ ID NO:1;
  (2) an HVR-H2 comprising the amino acid sequence of SEQ ID NO:4;
  (3) an HVR-H3 comprising the amino acid sequence of SEQ ID NO:5;
  (4) an HVR-L1 comprising the amino acid sequence of SEQ ID NO:7;
  (5) an HVR-L2 comprising the amino acid sequence of SEQ ID NO:8; and
  (6) an HVR-L3 comprising the amino acid sequence of SEQ ID NO:11.

30. The composition of claim 24, wherein the antibody comprises:
  (1) an HVR-H1 comprising the amino acid sequence of SEQ ID NO:2;
  (2) an HVR-H2 comprising the amino acid sequence of SEQ ID NO:4;
  (3) an HVR-H3 comprising the amino acid sequence of SEQ ID NO:5;
  (4) an HVR-L1 comprising the amino acid sequence of SEQ ID NO:7;
  (5) an HVR-L2 comprising the amino acid sequence of SEQ ID NO:8; and
  (6) an HVR-L3 comprising the amino acid sequence of SEQ ID NO:12.

31. The composition of claim 24, wherein the antibody comprises:
(1) an HVR-H1 comprising the amino acid sequence of SEQ ID NO:3;
(2) an HVR-H2 comprising the amino acid sequence of SEQ ID NO:4;
(3) an HVR-H3 comprising the amino acid sequence of SEQ ID NO:5;
(4) an HVR-L1 comprising the amino acid sequence of SEQ ID NO:7;
(5) an HVR-L2 comprising the amino acid sequence of SEQ ID NO:8; and
(6) an HVR-L3 comprising the amino acid sequence of SEQ ID NO:13.

32. The composition of claim 24, wherein the antibody comprises:
(1) an HVR-H1 comprising the amino acid sequence of SEQ ID NO:1;
(2) an HVR-H2 comprising the amino acid sequence of SEQ ID NO:4;
(3) an HVR-H3 comprising the amino acid sequence of SEQ ID NO:5;
(4) an HVR-L1 comprising the amino acid sequence of SEQ ID NO:7;
(5) an HVR-L2 comprising the amino acid sequence of SEQ ID NO:8; and
(6) an HVR-L3 comprising the amino acid sequence of SEQ ID NO:14.

33. The composition of claim 24, wherein the antibody comprises:
(1) an HVR-H1 comprising the amino acid sequence of SEQ ID NO:3;
(2) an HVR-H2 comprising the amino acid sequence of SEQ ID NO:4;
(3) an HVR-H3 comprising the amino acid sequence of SEQ ID NO:5;
(4) an HVR-L1 comprising the amino acid sequence of SEQ ID NO:7;
(5) an HVR-L2 comprising the amino acid sequence of SEQ ID NO:8; and
(6) an HVR-L3 comprising the amino acid sequence of SEQ ID NO:33.

34. The composition of claim 24, wherein the antibody comprises a VH sequence of SEQ ID NO:15, SEQ ID NO:27, SEQ ID NO:16, or SEQ ID NO:17.

35. The composition of claim 24, wherein the antibody comprises a VL sequence of SEQ ID NO:18, SEQ ID NO:19, SEQ ID NO:20, SEQ ID NO:21, SEQ ID NO:22, or SEQ ID NO:34.

36. The composition of claim 24, wherein the antibody comprises a VH sequence of SEQ ID NO:15 and a VL sequence of SEQ ID NO:18.

37. The composition of claim 24, wherein the antibody comprises a VH sequence of SEQ ID NO:15 and a VL sequence of SEQ ID NO:19.

38. The composition of claim 24, wherein the antibody comprises a VH sequence of SEQ ID NO:27 and a VL sequence of SEQ ID NO:20.

39. The composition of claim 24, wherein the antibody comprises a VH sequence of SEQ ID NO:16 and a VL sequence of SEQ ID NO:21.

40. The composition of claim 24, wherein the antibody comprises a VH sequence of SEQ ID NO:17 and a VL sequence of SEQ ID NO:22.

41. The composition of claim 24, wherein the antibody comprises a VH sequence of SEQ ID NO:17 and a VL sequence of SEQ ID NO:34.

42. The composition of claim 24, wherein the antibody comprises (i) a heavy chain comprising the amino acid sequence of SEQ ID NO:35 and a light chain comprising the amino acid sequence of SEQ ID NO:36, (ii) a heavy chain comprising amino acids 1-450 of SEQ ID NO:35 and a light chain comprising the amino acid sequence of SEQ ID NO:36, (iii) a heavy chain comprising amino acids 1-449 of SEQ ID NO:35 and a light chain comprising the amino acid sequence of SEQ ID NO:36, or (iv) the heavy and light chain of any one of (i), (ii), or (iii) wherein the proline at amino acid position 449 of SEQ ID NO:35 is amidated.

* * * * *

UNITED STATES PATENT AND TRADEMARK OFFICE
CERTIFICATE OF CORRECTION

PATENT NO.       : 9,266,961 B2                                Page 1 of 1
APPLICATION NO.  : 13/918755
DATED            : February 23, 2016
INVENTOR(S)      : Yan Wu et al.

It is certified that error appears in the above-identified patent and that said Letters Patent is hereby corrected as shown below:

Claims

In column 125, line 7, claim 17, delete "kexin" and insert -- subtilisin/kexin --, therefor.

In column 126, line 2, claim 24, delete "QQAYX1X2X3X4T" and insert -- QQAYX$_1$X$_2$X$_3$X$_4$T --, therefor.

Signed and Sealed this
Second Day of August, 2016

Michelle K. Lee
*Director of the United States Patent and Trademark Office*

```
                        SEQUENCE LISTING

<160> NUMBER OF SEQ ID NOS: 45

<210> SEQ ID NO 1
<211> LENGTH: 10
<212> TYPE: PRT
<213> ORGANISM: Artificial Sequence
<220> FEATURE:
<223> OTHER INFORMATION: Synthetic construct

<400> SEQUENCE: 1

Gly Phe Thr Phe Thr Gly Tyr Ala Ile His
 1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Gly Phe Thr Phe Thr Arg His Thr Ile His
 1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Gly Phe Thr Phe Ser Ser Thr Ala Ile His
 1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic construct

<400> SEQUENCE: 4

Arg Ile Ser Pro Ala Asn Gly Asn Thr Asn Tyr Ala Asp Ser Val Lys
 1               5                   10                  15

Gly
```

```
<210> SEQ ID NO 5
<211> LENGTH: 12
<212> TYPE: PRT
<213> ORGANISM: Artificial Sequence
<220> FEATURE:
<223> OTHER INFORMATION: Synthetic construct

<400> SEQUENCE: 5

Trp Ile Gly Ser Arg Glu Leu Tyr Ile Met Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic construct

<400> SEQUENCE: 6

Arg Ala Ser Gln Asp Val Ser Ser Ala Val Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic construct

<400> SEQUENCE: 7

Arg Ala Ser Gln Asp Val Ser Thr Ala Val Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic construct

<400> SEQUENCE: 8

Ser Ala Ser Phe Leu Tyr Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic construct

<400> SEQUENCE: 9

Gln Gln Ser Tyr Thr Thr Pro Pro Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic construct

<400> SEQUENCE: 10

Gln Gln Ser Tyr Pro Ala Pro Ala Thr
1               5
```

```
<210> SEQ ID NO 11
<211> LENGTH: 9
<212> TYPE: PRT
<213> ORGANISM: Artificial Sequence
<220> FEATURE:
<223> OTHER INFORMATION: Synthetic construct

<400> SEQUENCE: 11

Gln Gln Ser Tyr Pro Ser Pro Ala Thr
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic construct

<400> SEQUENCE: 12

Gln Gln Ser Tyr Arg Ile Gln Pro Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic construct

<400> SEQUENCE: 13

Gln Gln Ser Tyr Pro Ala Leu His Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic construct

<400> SEQUENCE: 14

Gln Gln Ser Tyr Pro Ala Pro Ser Thr
 1               5

<210> SEQ ID NO 15
<211> LENGTH: 121
<212> TYPE: PRT
<213> ORGANISM: Artificial Sequence
<220> FEATURE:
<223> OTHER INFORMATION: Synthetic construct

<400> SEQUENCE: 15

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Gly Tyr
            20                  25                  30

Ala Ile His Trp Val Arg Gln Ala Pro Gly Lys Gly Leu Glu Trp Val
        35                  40                  45

Gly Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ala Arg Trp Ile Gly Ser Arg Glu Leu Tyr Ile Met Asp Tyr Trp Gly
                100                 105                 110

Gln Gly Thr Leu Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: Synthetic construct

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Arg His
                20                  25                  30

Thr Ile His Trp Val Arg Gln Ala Pro Gly Lys Gly Leu Glu Trp Val
            35                  40                  45

Ala Arg Ile Ser Pro Ala Asn Gly Asn Thr Asn Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
                100                 105                 110

Gln Gly Thr Leu Val Thr Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: Synthetic construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
                20                  25                  30

Ala Ile His Trp Val Arg Gln Ala Pro Gly Lys Gly Leu Glu Trp Val
            35                  40                  45

Ala Arg Ile Ser Pro Ala Asn Gly Asn Thr Asn Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
                100                 105                 110

Gln Gly Thr Leu Val Thr Val Ser Ser
        115                 120

<210> SEQ ID NO 18
<211> LENGTH: 107
<212> TYPE: PRT
<213> ORGANISM: Artificial Sequence
```

<220> FEATURE:
<223> OTHER INFORMATION: Synthetic construct

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Synthetic construct

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ala Pro Ala
                85                  90                  95

Thr Phe Gly Gln Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Synthetic construct

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Pro Ser Pro Ala
                 85                  90                  95

Thr Phe Gly Gln Gly Thr Lys Val Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: Synthetic construct

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Arg Ile Gln Pro
                 85                  90                  95

Thr Phe Gly Gln Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Synthetic construct

<400> SEQUENCE: 22

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Pro Ala Leu His
                 85                  90                  95

Thr Phe Gly Gln Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Synthetic construct
```

-continued

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ala Pro Ser
                85                  90                  95

Thr Phe Gly Gln Gly Thr Lys Val Glu Ile Lys
            100                 105

<210> SEQ ID NO 24
<211> LENGTH: 692
<212> TYPE: PRT
<213> ORGANISM: Homo sapiens

<400> SEQUENCE: 24

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

```
Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670
```

Thr Ala Val Ala Ile Cys Cys Arg Ser Arg His Leu Ala Gln Ala Ser
    675                 680                 685

Gln Glu Leu Gln
    690

<210> SEQ ID NO 25
<211> LENGTH: 3636
<212> TYPE: DNA
<213> ORGANISM: Homo sapiens

<400> SEQUENCE: 25

| | | | | | |
|---|---|---|---|---|---|
| cagcgacgtc | gaggcgctca | tggttgcagg | cgggcgccgc | cgttcagttc | agggtctgag | 60 |
| cctggaggag | tgagccaggc | agtgagactg | gctcgggcgg | gccgggacgc | gtcgttgcag | 120 |
| cagcggctcc | cagctcccag | ccaggattcc | gcgcgcccct | tcacgcgccc | tgctcctgaa | 180 |
| cttcagctcc | tgcacagtcc | tccccaccgc | aaggctcaag | gcgccgccgg | cgtggaccgc | 240 |
| gcacggcctc | taggtctcct | cgccaggaca | gcaacctctc | ccctggccct | catgggcacc | 300 |
| gtcagctcca | ggcggtcctg | gtggccgctg | ccactgctgc | tgctgctgct | gctgctcctg | 360 |
| ggtcccgcgg | gcgcccgtgc | gcaggaggac | gaggacggcg | actacgagga | gctggtgcta | 420 |
| gccttgcgtt | ccgaggagga | cggcctggcc | gaagcacccg | agcacggaac | cacagccacc | 480 |
| ttccaccgct | gcgccaagga | tccgtggagg | ttgcctggca | cctacgtggt | ggtgctgaag | 540 |
| gaggagaccc | acctctcgca | gtcagagcgc | actgcccgcc | gctgcaggc | caggctgcc | 600 |
| cgccggggat | acctcaccaa | gatcctgcat | gtcttccatg | gccttcttcc | tggcttcctg | 660 |
| gtgaagatga | gtggcgacct | gctggagctg | gccttgaagt | tgcccatgt | cgactacatc | 720 |
| gaggaggact | cctctgtctt | tgcccagagc | atcccgtgga | acctggagcg | gattacccct | 780 |
| ccacggtacc | gggcggatga | ataccagccc | cccgacggag | cagcctggt | ggaggtgtat | 840 |
| ctcctagaca | ccagcataca | gagtgaccac | cgggaaatcg | agggcagggt | catggtcacc | 900 |
| gacttcgaga | atgtgcccga | ggaggacggg | acccgcttcc | acagacaggc | cagcaagtgt | 960 |
| gacagtcatg | gcacccacct | ggcaggggtg | gtcagcggcc | gggatgccgg | cgtggccaag | 1020 |
| ggtgccagca | tgcgcagcct | gcgcgtgctc | aactgccaag | ggaagggcac | ggttagcggc | 1080 |
| accctcatag | gcctggagtt | tattcggaaa | agccagctgg | tccagcctgt | ggggccactg | 1140 |
| gtggtgctgc | tgcccctggc | gggtgggtac | agccgcgtcc | tcaacgccgc | tgccagcgc | 1200 |
| ctggcgaggg | ctggggtcgt | gctggtcacc | gctgccggca | acttccggga | cgatgcctgc | 1260 |
| ctctactccc | cagcctcagc | tcccgaggtc | atcacagttg | ggccaccaa | tgcccaagac | 1320 |
| cagccggtga | ccctggggac | tttggggacc | aactttggcc | gctgtgtgga | cctctttgcc | 1380 |
| ccaggggagg | acatcattgg | tgcctccagc | gactgcagca | cctgctttgt | gtcacagagt | 1440 |
| gggacatcac | aggctgctgc | ccacgtggct | ggcattgcag | ccatgatgct | gtctgccgag | 1500 |
| ccggagctca | ccctgccga | gttgaggcag | agactgatcc | acttctctgc | caaagatgtc | 1560 |
| atcaatgagg | cctggttccc | tgaggaccag | cgggtactga | ccccaacct | ggtggccgcc | 1620 |
| ctgcccccca | gcacccatgg | ggcaggttgg | cagctgtttt | gcaggactgt | atggtcagca | 1680 |
| cactcggggc | ctacacggat | ggccacagcc | gtcgcccgct | cgcgccccaga | tgaggagctg | 1740 |
| ctgagctgct | ccagtttctc | caggagtggg | aagcggcggg | gcgagcgcat | ggaggcccaa | 1800 |
| gggggcaagc | tggtctgccg | ggccacaaac | gctttggggg | gtgagggtgt | ctacgccatt | 1860 |
| gccaggtgct | gcctgctacc | ccaggccaac | tgcagcgtcc | acacagctcc | accagctgag | 1920 |
| gccagcatgg | ggacccgtgt | ccactgccac | caacagggcc | acgtcctcac | aggctgcagc | 1980 |

```
tcccactggg aggtggagga ccttggcacc cacaagccgc ctgtgctgag gccacgaggt    2040
cagcccaacc agtgcgtggg ccacagggag gccagcatcc acgcttcctg ctgccatgcc    2100
ccaggtctgg aatgcaaagt caaggagcat ggaatcccgg cccctcagga gcaggtgacc    2160
gtggcctgcg aggagggctg gaccctgact ggctgcagtg ccctccctgg gacctcccac    2220
gtcctggggg cctacgccgt agacaacacg tgtgtagtca ggagccggga cgtcagcact    2280
acaggcagca ccagcgaagg ggccgtgaca gccgttgcca tctgctgccg gagccggcac    2340
ctggcgcagg cctcccagga gctccagtga cagccccatc ccaggatggg tgtctgggga    2400
gggtcaaggg ctggggctga gctttaaaat ggttccgact tgtccctctc tcagccctcc    2460
atggcctggc acgaggggat ggggatgctt ccgccttcc ggggctgctg gcctggccct     2520 tgagtgggc agcctccttg cctggaactc actcactctg ggtgcctcct ccccaggtgg     2580
aggtgccagg aagctccctc cctcactgtg gggcatttca ccattcaaac aggtcgagct    2640
gtgctcgggt gctgccagct gctcccaatg tgccgatgtc cgtgggcaga atgactttta    2700
ttgagctctt gttccgtgcc aggcattcaa tcctcaggtc tccaccaagg aggcaggatt    2760
cttcccatgg ataggggagg gggcggtagg ggctgcaggg acaaacatcg ttgggggtg     2820 agtgtgaaag gtgctgatgg ccctcatctc cagctaactg tggagaagcc cctgggggct    2880
ccctgattaa tggaggctta gctttctgga tggcatctag ccagaggctg gagacaggtg    2940
cgcccctggt ggtcacaggc tgtgccttgg tttcctgagc cacctttact ctgctctatg    3000
ccaggctgtg ctagcaacac ccaaaggtgg cctgcgggga ccatcacct aggactgact     3060 cggcagtgtg cagtggtgca tgcactgtct cagccaaccc gctccactac ccggcagggt    3120
acacattcgc acccctactt cacagaggaa gaaacctgga accagagggg gcgtgcctgc    3180
caagctcaca cagcaggaac tgagccgaaa acgcagattg ggctggctct gaagccaagc    3240
ctcttcttac ttcacccggc tgggctcctc attttttacgg gtaacagtga ggctgggaag    3300
gggaacacag accaggaagc tcggtgagtg atggcagaac gatgcctgca ggcatggaac    3360
tttttccgtt atcacccagg cctgattcac tggcctggcg gagatgcttc taaggcatgg    3420
tcgggggaga gggccaacaa ctgtccctcc ttgagcacca gccccaccca agcaagcaga    3480
catttatctt tgggtctgt cctctctgtt gccttttac agccaacttt tctagacctg      3540
ttttgctttt gtaacttgaa gatatttatt ctgggttttg tagcatttt attaatatgg     3600 tgacttttta aaataaaaac aaacaaacgt tgtcct                              3636
```

<210> SEQ ID NO 26
<211> LENGTH: 7
<212> TYPE: PRT
<213> ORGANISM: Artificial Sequence
<220> FEATURE:
<223> OTHER INFORMATION: Synthetic construct

<400> SEQUENCE: 26

Ser Ala Ser Ser Leu Tyr Ser
 1               5

<210> SEQ ID NO 27
<211> LENGTH: 121
<212> TYPE: PRT
<213> ORGANISM: Artificial Sequence
<220> FEATURE:
<223> OTHER INFORMATION: Synthetic construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Ala Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 28
<211> LENGTH: 10
<212> TYPE: PRT
<213> ORGANISM: Artificial Sequence
<220> FEATURE:
<223> OTHER INFORMATION: Synthetic construct
<221> NAME/KEY: VARIANT
<222> LOCATION: 5
<223> OTHER INFORMATION: Xaa = Ser or Thr
<221> NAME/KEY: VARIANT
<222> LOCATION: 6
<223> OTHER INFORMATION: Xaa = Gly, Arg or Ser
<221> NAME/KEY: VARIANT
<222> LOCATION: 7
<223> OTHER INFORMATION: Xaa = His, Thr or Tyr
<221> NAME/KEY: VARIANT
<222> LOCATION: 8
<223> OTHER INFORMATION: Xaa = Ala or Thr

<400> SEQUENCE: 28

Gly Phe Thr Phe Xaa Xaa Xaa Xaa Ile His
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic construct
<221> NAME/KEY: VARIANT
<222> LOCATION: 8
<223> OTHER INFORMATION: Xaa = Ser or Thr

<400> SEQUENCE: 29

Arg Ala Ser Gln Asp Val Ser Xaa Ala Val Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic construct
<221> NAME/KEY: VARIANT
<222> LOCATION: 4
<223> OTHER INFORMATION: Xaa = Phe or Ser

```
<400> SEQUENCE: 30

Ser Ala Ser Xaa Leu Tyr Ser
 1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic construct
<221> NAME/KEY: VARIANT
<222> LOCATION: 5
<223> OTHER INFORMATION: Xaa = Pro, Arg or Thr
<221> NAME/KEY: VARIANT
<222> LOCATION: 6
<223> OTHER INFORMATION: Xaa = Ala, Ile, Ser or Thr
<221> NAME/KEY: VARIANT
<222> LOCATION: 7
<223> OTHER INFORMATION: Xaa = Leu, Pro or Gln
<221> NAME/KEY: VARIANT
<222> LOCATION: 8
<223> OTHER INFORMATION: Xaa = Ala, His, Pro or Ser

<400> SEQUENCE: 31

Gln Gln Ser Tyr Xaa Xaa Xaa Xaa Thr
 1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic construct

<400> SEQUENCE: 32

His His His His His His His His
 1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic construct

<400> SEQUENCE: 33

Gln Gln Ala Tyr Pro Ala Leu His Thr
 1               5

<210> SEQ ID NO 34
<211> LENGTH: 107
<212> TYPE: PRT
<213> ORGANISM: Artificial Sequence
<220> FEATURE:
<223> OTHER INFORMATION: Synthetic construct

<400> SEQUENCE: 34

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Pro Ala Leu His
                 85                  90                  95

Thr Phe Gly Gln Gly Thr Lys Val Glu Ile Lys
            100                 105
```

<210> SEQ ID NO 35
<211> LENGTH: 451
<212> TYPE: PRT
<213> ORGANISM: Artificial Sequence
<220> FEATURE:
<223> OTHER INFORMATION: Synthetic construct

<400> SEQUENCE: 35

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Thr
                 20                  25                  30

Ala Ile His Trp Val Arg Gln Ala Pro Gly Lys Gly Leu Glu Trp Val
             35                  40                  45

Ala Arg Ile Ser Pro Ala Asn Gly Asn Thr Asn Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320
```

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 36
<211> LENGTH: 214
<212> TYPE: PRT
<213> ORGANISM: Artificial Sequence
<220> FEATURE:
<223> OTHER INFORMATION: Synthetic construct

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Pro Ala Leu His
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

```
<210> SEQ ID NO 37
<211> LENGTH: 9
<212> TYPE: PRT
<213> ORGANISM: Artificial Sequence
<220> FEATURE:
<223> OTHER INFORMATION: Synthetic construct
<221> NAME/KEY: VARIANT
<222> LOCATION: 5
<223> OTHER INFORMATION: Xaa = Pro, Arg or Thr
<221> NAME/KEY: VARIANT
<222> LOCATION: 6
<223> OTHER INFORMATION: Xaa = Ala, Ile, Ser or Thr
<221> NAME/KEY: VARIANT
<222> LOCATION: 7
<223> OTHER INFORMATION: Xaa = Leu, Pro or Gln
<221> NAME/KEY: VARIANT
<222> LOCATION: 8
<223> OTHER INFORMATION: Xaa = Ala, His, Pro or Ser

<400> SEQUENCE: 37

Gln Gln Ala Tyr Xaa Xaa Xaa Xaa Thr
 1               5

<210> SEQ ID NO 38
<211> LENGTH: 1353
<212> TYPE: DNA
<213> ORGANISM: Artificial Sequence
<220> FEATURE:
<223> OTHER INFORMATION: Synthetic construct

<400> SEQUENCE: 38
gaagttcagc tggtggagtc tggcggtggc ctggtgcagc caggggggctc actccgtttg      60 tcctgtgcag cttctggctt caccttctct agtactgcta ttcactgggt gcgtcaggcc     120
ccgggtaagg gcctggaatg ggttgctagg atttctcctg ctaacggtaa tactaactat     180
gccgatagcg tcaagggccg tttcactata agcgcagaca catccaaaaa cacagcctac     240
ctacaaatga acagcttaag agctgaggac actgccgtct attattgtgc tcgttggatc     300
gggtcccggg agctgtacat tatggactac tggggtcaag aaccctggt caccgtctcc     360 tcggcctcca ccaagggccc atcggtcttc cccctggcac cctcctccaa gagcacctct     420
gggggcacag cggccctggg ctgcctggtc aaggactact ccccgaacc ggtgacggtg     480 tcgtggaact caggcgccct gaccagcggc gtgcacacct tcccggctgt cctacagtcc     540
tcaggactct actccctcag cagcgtggtg actgtgccct ctagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc     780 cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca agggcagccc cgagaaccca ggtgtacac ccctgccccc atcccgggaa    1080
gagatgacca gaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353
```

```
<210> SEQ ID NO 39
<211> LENGTH: 363
<212> TYPE: DNA
<213> ORGANISM: Artificial Sequence
<220> FEATURE:
<223> OTHER INFORMATION: Synthetic construct

<400> SEQUENCE: 39
gaagttcagc tggtggagtc tggcggtggc ctggtgcagc caggggctc actccgtttg      60 tcctgtgcag cttctggctt caccttctct agtactgcta ttcactgggt gcgtcaggcc    120
ccgggtaagg gcctggaatg ggttgctagg atttctcctg ctaacggtaa tactaactat    180
gccgatagcg tcaagggccg tttcactata agcgcagaca catccaaaaa cacagcctac    240
ctacaaatga acagcttaag agctgaggac actgccgtct attattgtgc tcgttggatc    300
gggtcccggg agctgtacat tatggactac tggggtcaag aaccctggt caccgtctcc     360 tcg                                                                  363

<210> SEQ ID NO 40
<211> LENGTH: 642
<212> TYPE: DNA
<213> ORGANISM: Artificial Sequence
<220> FEATURE:
<223> OTHER INFORMATION: Synthetic construct

<400> SEQUENCE: 40
gatatccaga tgacccagtc cccgagctcc ctgtccgcct ctgtgggcga tagggtcacc     60
atcacctgcc gtgccagtca ggatgtgtcc actgctgtag cctggtatca acagaaacca   120
ggaaaagctc cgaagcttct gatttactcg gcatccttcc tctactctgg agtcccttct   180
cgcttctctg gtagcggttc cgggacggat ttcactctga ccatcagcag tctgcagccg   240
gaagacttcg caacttatta ctgtcagcaa gcctatccgg ccctacacac gttcggacag   300
ggtaccaagg tggagatcaa acgaactgtg gctgcaccat ctgtcttcat cttcccgcca   360
tctgatgagc agttgaaatc tggaactgct tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642

<210> SEQ ID NO 41
<211> LENGTH: 324
<212> TYPE: DNA
<213> ORGANISM: Artificial Sequence
<220> FEATURE:
<223> OTHER INFORMATION: Synthetic construct

<400> SEQUENCE: 41
gatatccaga tgacccagtc cccgagctcc ctgtccgcct ctgtgggcga tagggtcacc     60
atcacctgcc gtgccagtca ggatgtgtcc actgctgtag cctggtatca acagaaacca   120
ggaaaagctc cgaagcttct gatttactcg gcatccttcc tctactctgg agtcccttct   180
cgcttctctg gtagcggttc cgggacggat ttcactctga ccatcagcag tctgcagccg   240
gaagacttcg caacttatta ctgtcagcaa gcctatccgg ccctacacac gttcggacag   300
ggtaccaagg tggagatcaa acga                                           324
```

<210> SEQ ID NO 42
<211> LENGTH: 10
<212> TYPE: PRT
<213> ORGANISM: Artificial Sequence
<220> FEATURE:
<223> OTHER INFORMATION: Synthetic construct

<400> SEQUENCE: 42

```
Gly Phe Thr Phe Thr Arg His Thr Ile Asn
1               5                   10
```

<210> SEQ ID NO 43
<211> LENGTH: 121
<212> TYPE: PRT
<213> ORGANISM: Artificial Sequence
<220> FEATURE:
<223> OTHER INFORMATION: Synthetic construct

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Arg His
            20                  25                  30

Thr Ile Asn Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120
```

<210> SEQ ID NO 44
<211> LENGTH: 107
<212> TYPE: PRT
<213> ORGANISM: Artificial Sequence
<220> FEATURE:
<223> OTHER INFORMATION: Synthetic construct

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105
```

```
<210> SEQ ID NO 45
<211> LENGTH: 10
<212> TYPE: PRT
<213> ORGANISM: Artificial Sequence
<220> FEATURE:
<223> OTHER INFORMATION: Synthetic construct
<221> NAME/KEY: VARIANT
<222> LOCATION: 5
<223> OTHER INFORMATION: Xaa = Ser or Thr
<221> NAME/KEY: VARIANT
<222> LOCATION: 6
<223> OTHER INFORMATION: Xaa = Gly, Arg or Ser
<221> NAME/KEY: VARIANT
<222> LOCATION: 7
<223> OTHER INFORMATION: Xaa = His, Thr or Tyr
<221> NAME/KEY: VARIANT
<222> LOCATION: 8
<223> OTHER INFORMATION: Xaa = Ala or Thr
<221> NAME/KEY: VARIANT
<222> LOCATION: 10
<223> OTHER INFORMATION: Xaa = His or Asn

<400> SEQUENCE: 45

Gly Phe Thr Phe Xaa Xaa Xaa Xaa Ile Xaa
 1               5                  10
```